United States Patent
Karren et al.

(10) Patent No.: US 11,629,076 B2
(45) Date of Patent: *Apr. 18, 2023

(54) SYSTEMS AND METHODS FOR PROVIDING AN ELECTROLYTIC CELL THAT PRODUCES CONDITIONED ELECTROLYZED WATER

(71) Applicant: Z Intellectual Property Holding Company, LLC, Pleasant Grove, UT (US)

(72) Inventors: Gaylord M. Karren, Draper, UT (US); James K. Stone, Draper, UT (US); John M. Hopkins, Draper, UT (US); William R. Shupe, Draper, UT (US)

(73) Assignee: Z Intellectual Property Holding Company, LLC, Pleasant Grove, UT (US)

( * ) Notice: Subject to any disclaimer, the term of this patent is extended or adjusted under 35 U.S.C. 154(b) by 959 days.

This patent is subject to a terminal disclaimer.

(21) Appl. No.: 16/286,493

(22) Filed: Feb. 26, 2019

(65) Prior Publication Data
US 2019/0276340 A1 Sep. 12, 2019

Related U.S. Application Data

(60) Provisional application No. 62/635,380, filed on Feb. 26, 2018.

(51) Int. Cl.
*C02F 1/461* (2006.01)
*C02F 1/48* (2006.01)
(Continued)

(52) U.S. Cl.
CPC ............. *C02F 1/4618* (2013.01); *A61L 2/18* (2013.01); *B08B 3/04* (2013.01); *B08B 3/08* (2013.01);
(Continued)

(58) Field of Classification Search
CPC ............ C02F 1/4618; C02F 2201/4614; C02F 2209/05; C02F 2301/026; C25B 15/033; C25B 15/02; A61L 2/18
See application file for complete search history.

(56) References Cited

U.S. PATENT DOCUMENTS

| 2,825,926 A | 3/1958 | Ripple |
| 3,808,631 A | 5/1974 | Shibata et al. |

(Continued)

FOREIGN PATENT DOCUMENTS

| CN | 204049531 U | 12/2014 |
| DE | 29805105 U1 | 5/1998 |

(Continued)

*Primary Examiner* — Nicholas A Smith
(74) *Attorney, Agent, or Firm* — David B. Tingey; Bryant J. Keller; Kirton McConkie

(57) ABSTRACT

The present invention relates to systems and methods for cleaning materials, such as flooring and upholstery. In some cases, the systems and methods use an electrolytic cell to electrolyze a solution comprising sodium carbonate, sodium bicarbonate, sodium acetate, sodium percarbonate, potassium carbonate, potassium bicarbonate, and/or any other suitable chemical to generate electrolyzed alkaline water and/or electrolyzed oxidizing water. In some cases, the cell comprises a recirculation loop that recirculates anolyte through an anode compartment of the cell. In some cases, the cell further comprises a senor and a processor, where the processor is configured to automatically change an operation of the cell, based on a reading from the sensor. In some cases, a fluid flows past a magnet before entering the cell. In some additional cases, fluid from the cell is conditioned by being split into multiple conduits that run in proximity to each other. Additional implementations are described.

20 Claims, 41 Drawing Sheets

(51) Int. Cl.
  *B08B 3/08* (2006.01)
  *C02F 1/00* (2006.01)
  *A61L 2/18* (2006.01)
  *B08B 3/10* (2006.01)
  *B08B 3/04* (2006.01)
  *A47L 11/40* (2006.01)
  *A47L 11/34* (2006.01)
  *C02F 103/02* (2006.01)

(52) U.S. Cl.
  CPC .............. *B08B 3/10* (2013.01); *C02F 1/008* (2013.01); *C02F 1/46109* (2013.01); *C02F 1/48* (2013.01); *C02F 1/481* (2013.01); *A47L 11/34* (2013.01); *A47L 11/4005* (2013.01); *A47L 11/4044* (2013.01); *A47L 11/4075* (2013.01); *A47L 11/4086* (2013.01); *A61L 2202/11* (2013.01); *C02F 1/005* (2013.01); *C02F 2001/4619* (2013.01); *C02F 2001/46185* (2013.01); *C02F 2103/026* (2013.01); *C02F 2201/008* (2013.01); *C02F 2201/4611* (2013.01); *C02F 2201/4612* (2013.01); *C02F 2201/4614* (2013.01); *C02F 2201/4619* (2013.01); *C02F 2201/46115* (2013.01); *C02F 2201/46125* (2013.01); *C02F 2201/46135* (2013.01); *C02F 2201/46145* (2013.01); *C02F 2201/46185* (2013.01); *C02F 2201/48* (2013.01); *C02F 2209/003* (2013.01); *C02F 2209/05* (2013.01); *C02F 2209/40* (2013.01); *C02F 2209/42* (2013.01); *C02F 2301/026* (2013.01); *C02F 2301/046* (2013.01); *C02F 2303/04* (2013.01); *C02F 2303/22* (2013.01)

(56) References Cited

U.S. PATENT DOCUMENTS

| | | |
|---|---|---|
| 3,828,390 A | 8/1974 | Cater |
| 3,909,197 A | 9/1975 | Cremers |
| 4,019,218 A | 4/1977 | Cyphert |
| 4,168,563 A | 9/1979 | O'Bryan |
| 4,329,756 A | 5/1982 | Chicoine et al. |
| 4,335,486 A | 6/1982 | Kochte |
| 4,385,413 A | 5/1983 | Goldsmith |
| 4,392,270 A | 7/1983 | Magee |
| 4,408,366 A | 10/1983 | Goldsmith |
| 4,466,155 A | 8/1984 | Grave |
| 4,729,409 A | 3/1988 | Paul |
| 4,879,784 A | 11/1989 | Shero |
| 4,906,496 A | 3/1990 | Hosono |
| 5,113,547 A | 5/1992 | Mayhew |
| 5,423,353 A | 6/1995 | Sorensen |
| 5,445,722 A | 8/1995 | Yamaguti et al. |
| 5,543,030 A | 8/1996 | Shiramizu et al. |
| 5,555,598 A | 9/1996 | Grave et al. |
| 5,815,869 A | 10/1998 | Hopkins |
| 5,891,198 A | 4/1999 | Pearlstein |
| 5,942,098 A | 8/1999 | Sekissov |
| 6,149,780 A | 11/2000 | Miyake |
| 6,263,539 B1 | 7/2001 | Baig |
| 6,560,818 B1 | 5/2003 | Hasko |
| 6,638,364 B2 | 10/2003 | Harkins et al. |
| 6,735,812 B2 | 5/2004 | Hekman et al. |
| 6,942,767 B1 | 9/2005 | Fazzina et al. |
| 7,836,543 B2 | 11/2010 | Field et al. |
| 8,025,786 B2 | 9/2011 | Field et al. |
| 8,025,787 B2 | 9/2011 | Field et al. |
| 8,123,954 B2 | 2/2012 | Lopes |
| 8,214,967 B2 | 7/2012 | Knox et al. |
| 8,425,756 B2 | 4/2013 | Kindred |
| 8,514,967 B2 | 8/2013 | Wu |
| 8,603,320 B2 | 12/2013 | Field |
| 9,162,904 B2 | 10/2015 | Guastella et al. |
| 9,468,351 B2 | 10/2016 | Meissner et al. |
| 10,041,177 B2 | 8/2018 | Nourbakhsh et al. |
| 10,413,147 B2 | 9/2019 | Hopkins et al. |
| 11,344,572 B2 | 5/2022 | Bishop et al. |
| 11,383,993 B2 * | 7/2022 | Karren ............... C02F 1/4618 |
| 2002/0116784 A1 | 8/2002 | Sumner |
| 2002/0158018 A1 | 10/2002 | Abramowitz et al. |
| 2003/0024066 A1 | 2/2003 | Kennedy |
| 2003/0159231 A1 | 8/2003 | Oh |
| 2003/0213503 A1 | 11/2003 | Price et al. |
| 2003/0213704 A1 | 11/2003 | Scheper et al. |
| 2004/0020835 A1 | 2/2004 | Chang |
| 2004/0060815 A1 | 4/2004 | Buckley et al. |
| 2004/0094406 A1 | 5/2004 | Sawada |
| 2004/0200007 A1 | 10/2004 | Heim |
| 2006/0076064 A1 | 4/2006 | Carter et al. |
| 2006/0144711 A1 | 7/2006 | Kobata et al. |
| 2006/0248677 A1 | 11/2006 | Cho |
| 2006/0272989 A1 | 12/2006 | Bagley |
| 2006/0272993 A1 | 12/2006 | Bagley |
| 2006/0273020 A1 | 12/2006 | Bagley |
| 2006/0275474 A1 | 12/2006 | Bagley |
| 2007/0023273 A1 | 2/2007 | Kitaori et al. |
| 2007/0028412 A1 | 2/2007 | Carter et al. |
| 2007/0051640 A1 | 3/2007 | Bellamy |
| 2007/0187261 A1 | 8/2007 | Field et al. |
| 2007/0187263 A1 | 8/2007 | Field et al. |
| 2008/0264781 A1 | 10/2008 | Iltsenko et al. |
| 2009/0100632 A1 | 4/2009 | Oh et al. |
| 2009/0120460 A1 | 5/2009 | Hekman et al. |
| 2010/0084274 A1 | 4/2010 | Uemori |
| 2011/0042202 A1 | 2/2011 | Pettee et al. |
| 2011/0155191 A1 | 6/2011 | Studebaker |
| 2011/0189302 A1 | 8/2011 | Van Niekerk et al. |
| 2011/0290650 A1 | 12/2011 | Bang |
| 2012/0042909 A1 | 2/2012 | Studebaker |
| 2012/0097550 A1 | 4/2012 | Lockhart |
| 2012/0121731 A1 | 5/2012 | Peters et al. |
| 2012/0160329 A1 | 6/2012 | MacKenzie et al. |
| 2012/0228145 A1 | 9/2012 | Guastella et al. |
| 2012/0267256 A1 | 10/2012 | Kindred |
| 2013/0072415 A1 | 3/2013 | Scheibel et al. |
| 2014/0124377 A1 * | 5/2014 | Joynt ............... C25B 15/02 205/335 |
| 2014/0367247 A1 | 12/2014 | Croke |
| 2015/0026914 A1 | 1/2015 | Meissner et al. |
| 2015/0051135 A1 | 2/2015 | Hermann et al. |
| 2016/0236954 A1 | 8/2016 | Liang |
| 2017/0008780 A1 | 1/2017 | Hong |
| 2017/0251896 A1 | 9/2017 | Hopkins et al. |
| 2017/0267553 A1 | 9/2017 | Gardner |
| 2018/0216895 A1 | 8/2018 | Koda |
| 2019/0263686 A1 | 8/2019 | Karren et al. |
| 2019/0263687 A1 | 8/2019 | Karren et al. |
| 2019/0263688 A1 | 8/2019 | Karren et al. |
| 2019/0263689 A1 | 8/2019 | Karren et al. |
| 2019/0263690 A1 | 8/2019 | Karren et al. |
| 2019/0263691 A1 | 8/2019 | Karren et al. |
| 2019/0284065 A1 | 9/2019 | Karren et al. |
| 2020/0008640 A1 | 1/2020 | Hopkins et al. |
| 2020/0176167 A1 | 6/2020 | Chen |
| 2022/0233045 A1 | 7/2022 | Karren et al. |

FOREIGN PATENT DOCUMENTS

| | | | |
|---|---|---|---|
| EP | 0642824 A1 | 3/1995 | |
| EP | 1508292 A2 | 2/2005 | |
| EP | 2225991 A2 | 9/2010 | |
| EP | 2233441 A1 * | 9/2010 | ............ C02F 1/4618 |
| EP | 2239231 A1 * | 10/2010 | ............ C02F 1/4618 |
| EP | 3759207 | 8/2019 | |
| EP | 3653586 A1 | 5/2020 | |
| JP | 11035472 A | 2/1999 | |
| JP | 2000-126778 A | 5/2000 | |
| RU | 2620385 C2 | 5/2017 | |
| WO | 9746489 A1 | 12/1997 | |
| WO | 142143 A2 | 6/2001 | |
| WO | 2014053865 A1 | 4/2014 | |

(56) References Cited

FOREIGN PATENT DOCUMENTS

| WO | 2014114806 A1 | 7/2014 |
|----|---------------|--------|
| WO | 2017151976 A1 | 9/2017 |
| WO | 2019165474 A1 | 8/2019 |

* cited by examiner

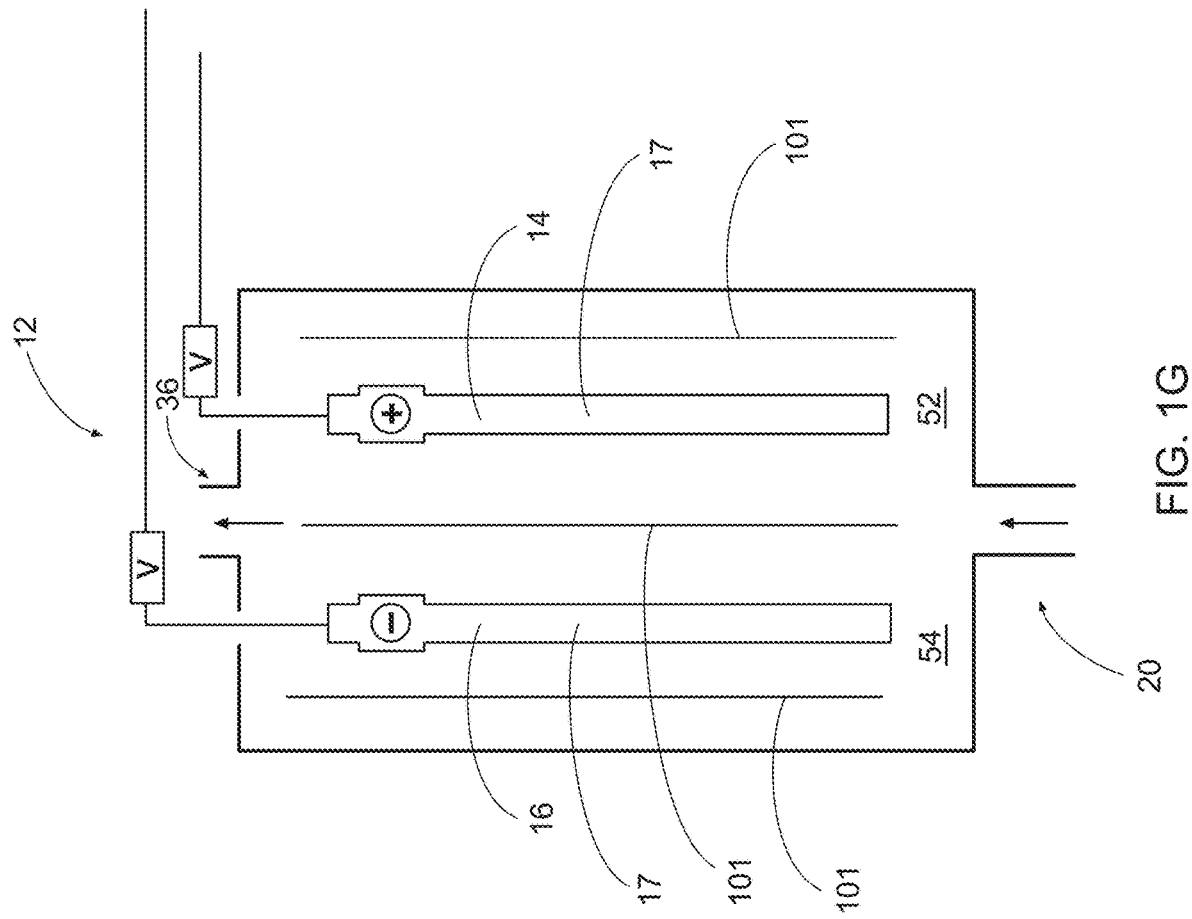

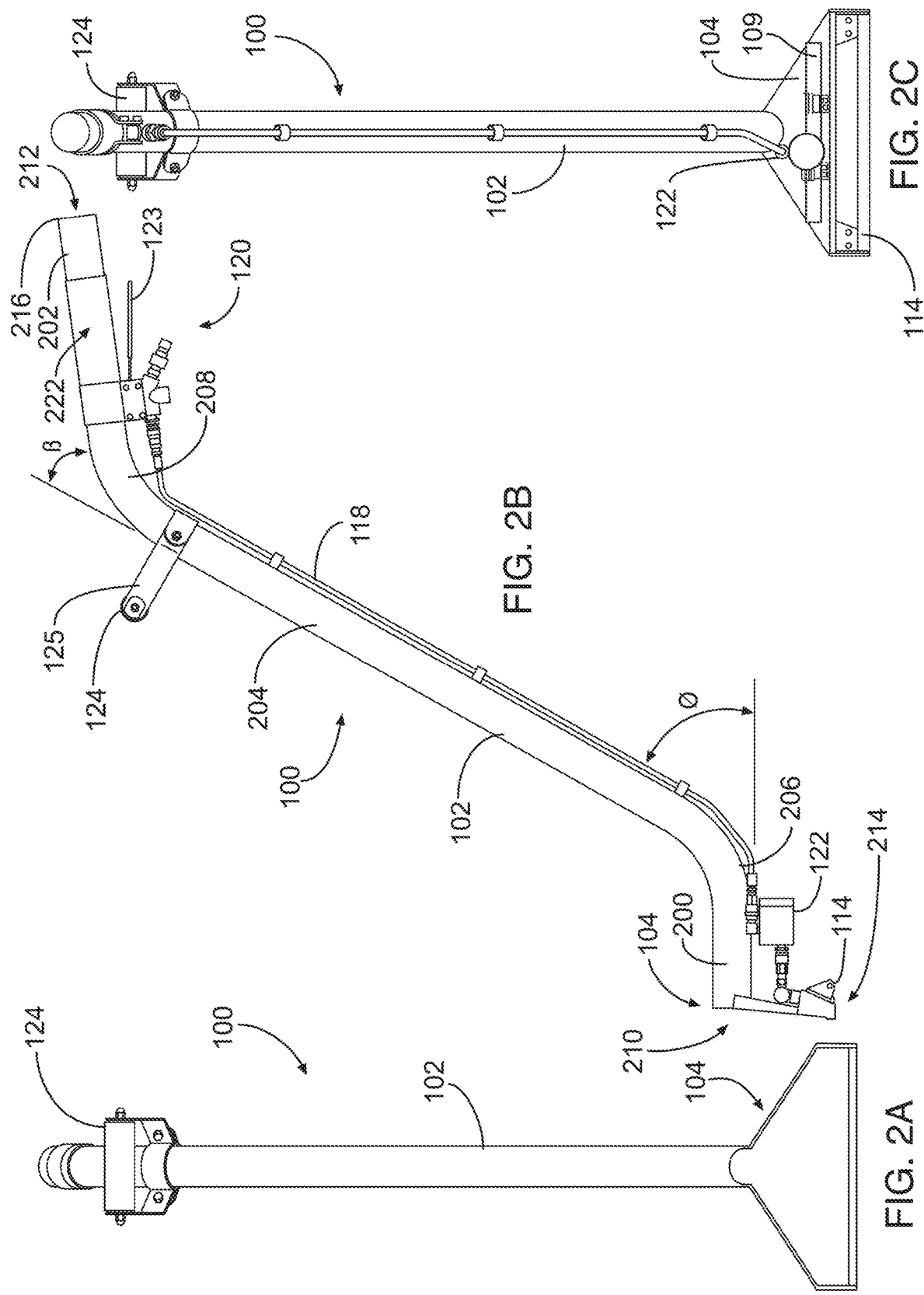

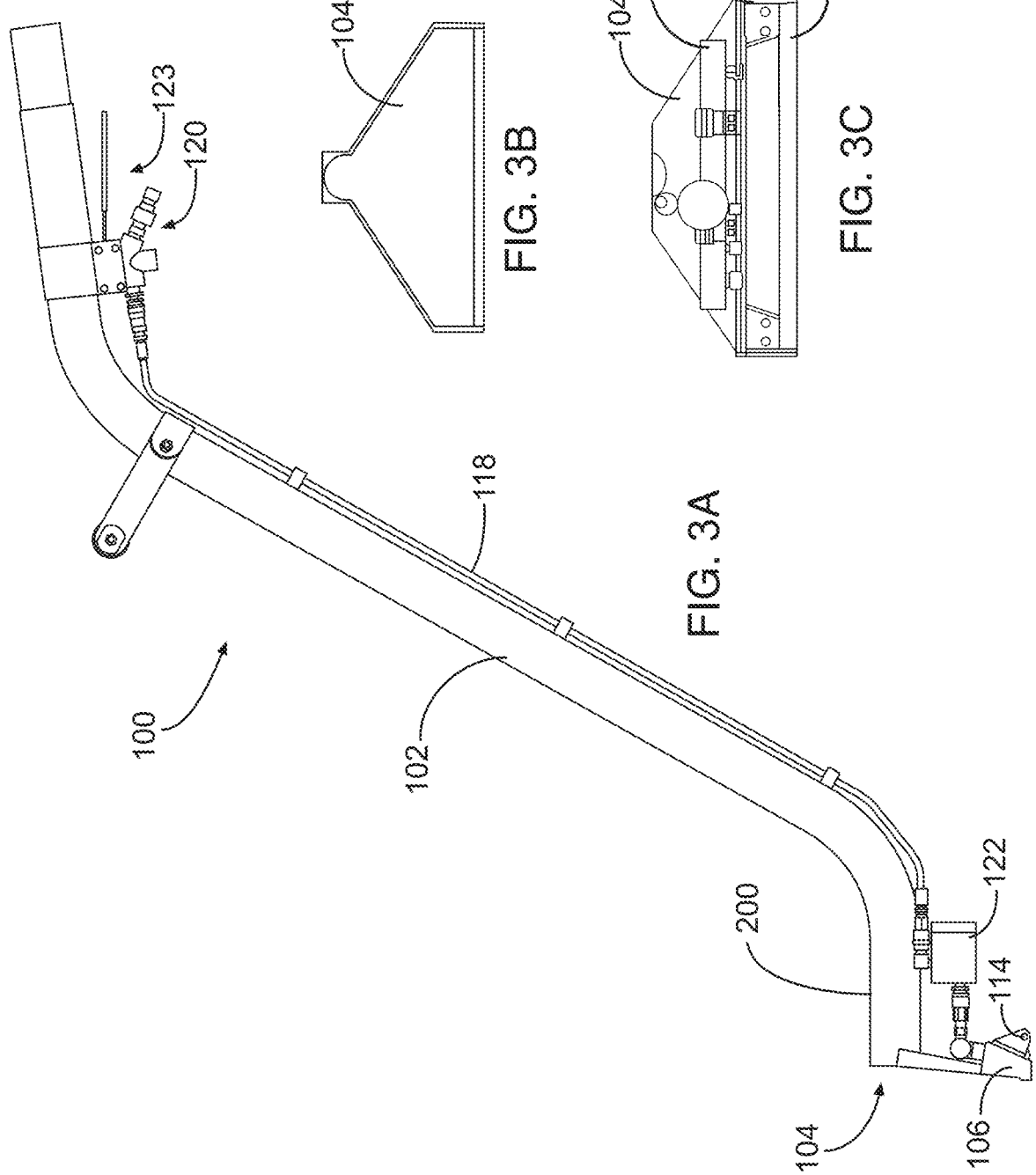

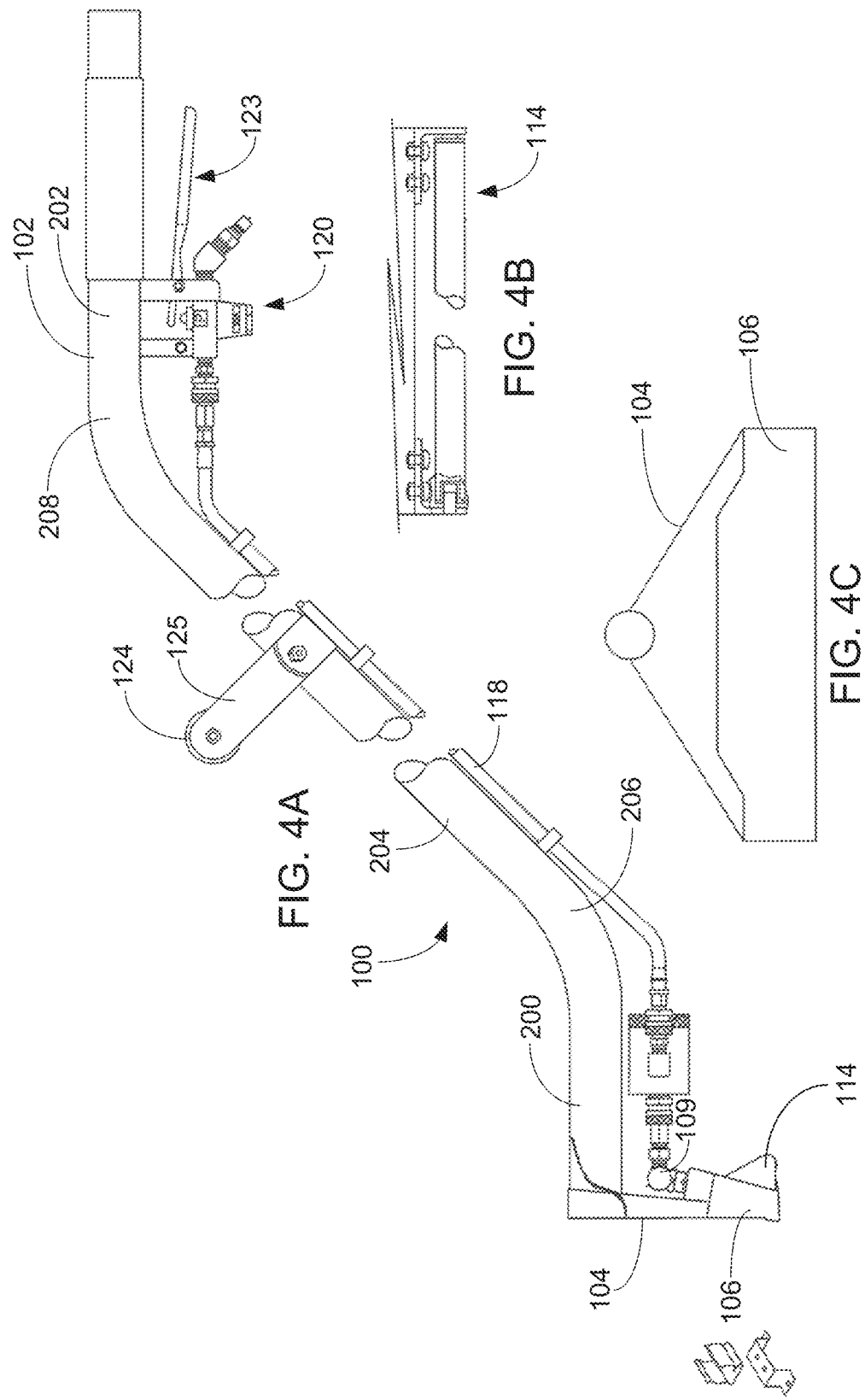

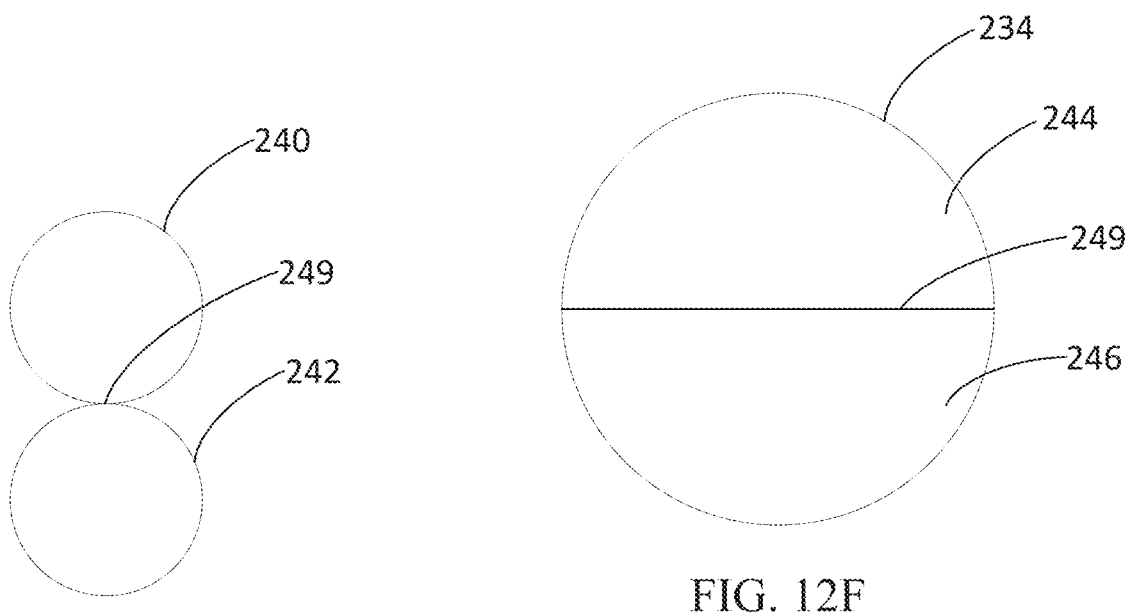
FIG. 12E
FIG. 12F
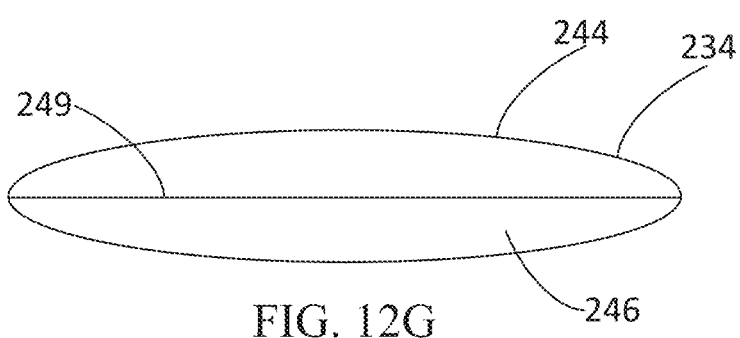
FIG. 12G
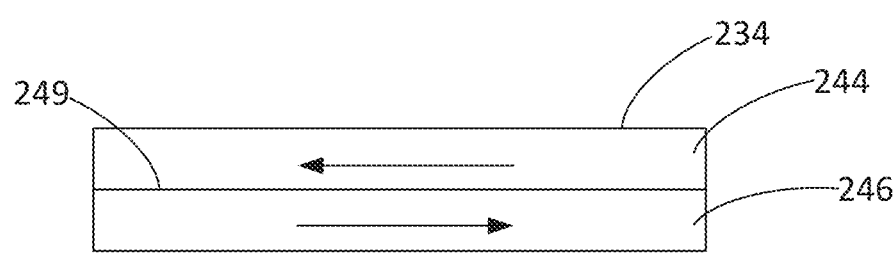
FIG. 12H

WATER ANALYSYS REPORT

ANALYSYS
1. Ph                             11.230
2. Specific Gravity 60/60 F.  @ 80F   1.027   0.912   Moderate
3. CAO3 Saturation Index     @140F            1.612   Severe

Dissolved Gasses
4. Hydrogen Sulfide      Not Determined
5. Carbon Dioxide        Not Determined
6. Dissolved Oxygen      Not Determined

|  | | MG/L | | EQ. WT. | | *MEQ/L |
|---|---|---|---|---|---|---|
| Cations | | | | | | |
| 7. Calcium | ($Ca^{++}$) | 20 | / | 20.1 | = | 1.00 |
| 8. Magnesium | ($Mg^{++}$) | 2 | / | 12.2 | = | 0.16 |
| 9. Sodium | ($Na^+$) (Calculated) | 372 | / | 23.0 | = | 16.17 |
| 10. Barium | ($Ba^{++}$) | 5 | / | 68.7 | = | 0.07 |
| Anions | | | | | | |
| 11. Hydroxyl | ($OH^-$) | 50 | / | 17.0 | = | 2.94 |
| 12. Carbonate | ($CO_3^=$) | -41 | / | 30.0 | = | 1.67 |
| 13. Bicarbonate | ($HCO_3^-$) | 0 | / | 61.1 | = | 0.00 |
| 14. Sulfate | ($SO_4^=$) | 51 | / | 48.8 | = | 1.05 |
| 15. Chloride | ($Cl^-$) | 578 | / | 35.5 | = | 16.28 |
| 16. Total Dissolved Solids | | 1,028 | | | | |
| 17. Total Iron | (Fe) | 0.02 | / | 18.2 | = | 0.00 |
| 18. Manganese | ($Mn^{++}$) | 0.20 | / | 27.5 | = | 0.01 |
| 19. Total Hardness as CaCO3 | | 58 | | | | |
| 20. Resistivity @ 75 F. (Calculated) | | 2.976 Ohm · meters | | | | |

LOGARITHMIC WATER PATTERN        PROBABLE MINERAL COMPOSITION
*meg / L.                         COMPOUND   *meg/L  X  EQ. WT.  =  mg/L.

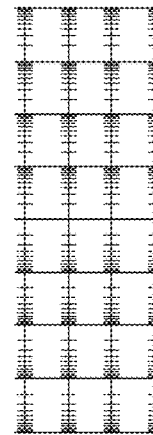

FIG. 12R

SYSTEMS AND METHODS FOR PROVIDING AN ELECTROLYTIC CELL THAT PRODUCES CONDITIONED ELECTROLYZED WATER

CROSS-REFERENCE TO RELATED APPLICATION

This application claims priority to U.S. Provisional Application No. 62/635,380, which was filed on Feb. 26, 2018, and which is entitled SYSTEMS AND METHODS FOR PRODUCING ELECTROLYZED ALKALINE WATER AND/OR ELECTROLYZED OXIDIZING WATER; the entire disclosure of which is hereby incorporated herein.

BACKGROUND OF THE INVENTION

1. Field of the Invention

The present invention relates to systems and methods for cleaning materials and surfaces, such as flooring, furniture, drapery, upholstery, and any other suitable materials and surfaces. In particular, some implementations of the present invention relate to systems and methods for using an electrolytic cell to generate electrolyzed alkaline water and/or electrolyzed oxidizing water by electrolyzing a solution comprising sodium carbonate, soda ash, sodium bicarbonate, washing soda, soda crystals, crystal carbonate, sodium acetate, sodium percarbonate, potassium carbonate, potassium bicarbonate, sodium chloride, potassium chloride, and/or any other suitable salt and/or other electrolyte (e.g., any suitable electrolyte comprising one or more alkali ions). In some cases, the cell comprises a recirculation loop that recirculates anolyte through an anode compartment of the cell. In some cases, the cell further comprises a senor and/or a processor, where the processor is configured to automatically change an operation of the cell, based on a reading from the sensor. In some cases, a fluid flows past a magnet before entering the cell. In some additional cases, fluid from the cell is conditioned by being split into multiple conduits that run in proximity to each other. While the electrolyzed alkaline and/or electrolyzed oxidizing water can be used for any suitable purpose, in some implementations, they are used to clean and/or disinfect carpets, rugs, tile, stone, linoleum, flooring surfaces, furniture, walls, drywall, plaster, countertops, blinds, appliances, woods, metals, vehicles, upholstery, drapes, fabrics, clothing, cloth, bedding, beds, laminates, surfaces which are touched by humans (e.g., door knobs, handrails, chairs, tables, light switches, remote controls, windows, etc.), wounds, and/or any other suitable surface, object, or material.

2. Background and Related Art

In accordance with many conventional carpet cleaning techniques, one or more soaps and/or detergents are applied to a carpet, either alone or with water and/or steam. In some cases, the soaps and/or detergents are then agitated into the carpet to allow them to act as emulsifiers; to form micelles around oils, grease, dirt, and other debris; and/or to otherwise capture and/or loosen up debris in the carpets. In some cases, the carpet is then rinsed and/or vacuumed to remove the soaps, detergents, water, and/or debris from the carpets.

While such carpet cleaning techniques can be quite effective at cleaning carpets, such techniques are not necessarily without their shortcomings. Indeed, in some such techniques, it can often be very difficult to remove all of the soaps and/or detergents from the carpet. In some such cases, as soap and/or detergents are left in the carpet, such cleaning agents continue to capture dirt, oil, and/or other debris. As result, carpets that still contain soap and/or detergent residue after being cleaned can actually become and look dirtier faster than similar carpets that are free from soap and/or detergent residue. As an additional shortcoming, some conventional carpet cleaning techniques employ soaps and/or detergents that are, in and of themselves, somewhat ineffective at removing stains and other debris from carpets. As a result, much effort can be spent in attempting to clean a carpet with such soaps and/or detergents, without the carpet ever truly becoming clean.

Thus, while techniques currently exist that are used to clean carpets and other materials, challenges still exist, including those listed above. Accordingly, it would be an improvement in the art to augment or even replace current techniques with other techniques.

SUMMARY OF THE INVENTION

The present invention relates to systems and methods for cleaning materials and surfaces, such as flooring, furniture, drapery, upholstery, and any other suitable materials and surfaces. In particular, some implementations of the present invention relate to systems and methods for using an electrolytic cell to generate electrolyzed alkaline water and/or electrolyzed oxidizing water by electrolyzing a solution comprising sodium carbonate, soda ash, sodium bicarbonate, washing soda, soda crystals, crystal carbonate, sodium acetate, sodium percarbonate, potassium carbonate, potassium bicarbonate, sodium chloride, potassium chloride, and/or any other suitable salt and/or other electrolyte (e.g., any suitable electrolyte comprising one or more alkali ions). In some cases, the cell comprises a recirculation loop that recirculates anolyte through an anode compartment of the cell. In some cases, the cell further comprises a senor and/or a processor, where the processor is configured to automatically change an operation of the cell, based on a reading from the sensor. In some cases, a fluid flows past a magnet before entering the cell. In some additional cases, fluid from the cell is conditioned by being split into multiple conduits that run in proximity to each other. While the electrolyzed alkaline and/or electrolyzed oxidizing water can be used for any suitable purpose, in some implementations, they are used to clean and/or disinfect carpets, rugs, tile, stone, linoleum, flooring surfaces, furniture, walls, drywall, plaster, countertops, blinds, appliances, woods, metals, vehicles, upholstery, drapes, fabrics, clothing, cloth, bedding, beds, laminates, surfaces which are touched by humans (e.g., door knobs, handrails, chairs, tables, light switches, remote controls, windows, etc.), wounds, and/or any other suitable surface, object, or material While the described systems can comprise any suitable component, in some implementations, the described system includes a water source, an electrolyte, an electrolytic cell, one or more pieces of cleaning equipment (e.g., one or more sprayers, heaters, wands, carpet agitators, suction devices, pieces of tubing, pieces of hosing, reservoirs, counter rotating brush devices, water softeners, and/or any other suitable piece of cleaning equipment), water conditioners, magnets, modified electrolyzed waters, wipes and/or other cleaning implements comprising an electrolyzed water, and/or any other suitable element or feature.

With respect to the water source, the water source can comprise any suitable water source, including, without limitation, potable water, non-potable water, reverse osmosis water, deionized water, distilled water, water from a tank, water from a tap, softened water (i.e., water that has been treated with a salt-based ion exchange water softener, a salt-free water softener, a dual-tank water softener, a magnetic water softener or descaler, and/or any other water softener), and/or any other suitable type of water from any other suitable water source.

With regards to the electrolyte source, the electrolyte can comprise any suitable electrolyte, including, without limitation, sodium carbonate ($Na_2CO_3$), soda ash, sodium bicarbonate ($NaHCO_3$), potash, potassium carbonate, potassium bicarbonate, sodium chloride, potassium chloride, sodium phosphate, and/or any other suitable electrolyte (e.g., any suitable electrolyte comprising sodium, potassium, and/or lithium). In some implementations, however, the electrolyte comprises sodium carbonate and/or sodium bicarbonate.

In some cases, prior to (and/or during) electrolysis, the electrolyte is added to water at any suitable concentration that allows the resultant electrolyte solution to be electrolyzed to form electrolyzed oxidizing water (acidic) and/or electrolyzed alkaline water (basic). In some implementations, the electrolyte (e.g., sodium carbonate and/or any other suitable electrolyte) is added to water at a concentration of between about 0.1% and about 60% by weight (or within any subrange thereof). Indeed, in some implementations, the electrolyte (e.g., sodium carbonate) is added to water at a concentration of between about 10% and about 30% by weight (e.g., at a concentration of about 20%±5%).

With regards to the electrolytic cell, the electrolyte (and its resultant electrolyte solution or solutions) can be electrolyzed in any suitable manner, including, without limitation, by being added to and/or being electrolyzed in an anode compartment and/or a cathode compartment of an electrolytic cell. Indeed, in some implementations, an electrolyte solution is added to both the anode compartment and the cathode compartment. In some other implementations, however, the electrolyte solution is added to the anode compartment, while water (and/or any other suitable material) is added to the cathode compartment, with the two compartments being separated by an ion permeable membrane (e.g., an alkali ion permeable membrane). In some such implementations, as the electrolytic cell is operated, sodium ions (and/or any other suitable alkali cations) from the electrolyzed electrolyte in the anode compartment (or the anolyte) are transferred through the membrane to combine with hydroxide ions in the solution in the cathode compartment (or the catholyte) to form sodium hydroxide (NaOH) (or electrolyzed alkaline water), which can then be used as a cleaning agent. Indeed, in some such implementations, the electrolyte in the anode compartment (or the anolyte) is selectively recycled through the anode compartment, released for use as a sanitizing agent, and/or otherwise used or discarded. In some cases, however, the anolyte is recycled through the anode compartment such that the described system can selectively produce a relatively large amount of cleaning solution (e.g., electrolyzed alkaline water) from the cathode compartment, while producing relatively little solution from the anode compartment (e.g., electrolyzed oxidizing water). Thus, in some cases, the described system can significantly reduce water consumption, without necessarily reducing the amount of electrolyzed alkaline water that it produces.

In some implementations, the described electrolytic cell comprises one or more sensors, control units, and/or processors that are used to gather information regarding cell operation and to vary the cell's operation based on the gathered data. In this regard, the cell can comprise (and/or otherwise be associated with) any suitable type of sensor, including, without limitation, one or more pH sensors, pressure sensors, flowrate sensors, conductivity sensors, current sensors, amperage sensors, voltage sensors, thermometers, oxidation-reduction potential ("ORP") sensors, water quality sensors, magnesium and/or calcium sensors, electrolyte concentration sensors, and/or any other suitable sensor or sensors that can be used to gather information on the cell and/or its operation.

Indeed, in some implementations, the cell comprises one or more conductivity sensors amperage sensors, concentration sensors, and/or flowrate sensors. In some such implementations, when the cell determines that conductivity of the electrolyte solution in the cell (e.g., in the anode compartment, the cathode compartment, an anolyte recirculation line, a storage tank, a fluid outlet, and/or any other suitable portion of the system) is below a desired threshold (e.g., because the solution does not have enough electrolyte, the amperage is too low, and/or for any other suitable reason), the cell (e.g., via one or more variable amperage power supplies, variable speed pumps, valves, dosing mechanisms, and/or any other suitable component) is configured to: increase the operating amperage of the electrodes (e.g., via the variable amperage power supply, to increase ion formation); slow the flowrate of electrolyte solution through the cell (e.g., through the anode compartment and/or any other suitable portion of the cell, so as to give the electrolyte more time to react and/or ionize); stabilize fluid pressures between the two flow channels (e.g., compartments) in the cell to allow the electrolyte to ionize and/or otherwise react more efficiently and maintain separation of the polarity of the ionic solutions; have more electrolyte introduced (e.g., into the anode compartment and/or the cathode compartment, as applicable) through the use of one or more pumps, variable pumps, valves, variable valves, droppers, dosing mechanisms, and/or any other suitable mechanism; and/or to otherwise vary operation of the cell to compensate for (and/or to otherwise attempt to correct) the low conductivity measurement.

In some cases, when one or more sensors determine that: the conductivity level of the electrolyte solution going through the cell (e.g., in the anode compartment, the cathode compartment, an anolyte recirculation line, a storage tank, a fluid outlet, and/or any other suitable portion of the system) is above a desired level; amperage is in the cell is too high; a flowrate is too low; an electrolyte concentration in the cell is too high; and/or that another parameter of the cell's operation is outside of a set ranges, some implementations of the cell are configured to: decrease the operating amperage of the electrodes (e.g., via a variable amperage power supply and/or in any other suitable manner to decrease ion formation); increase the flowrate of electrolyte solution through the cell (e.g., through the anode compartment and/or any other suitable portion of the cell, so as to give the electrolyte the optimal time and opportunity to ionize and/or otherwise react); increase flowrate through either side of the cell to maintain equal internal cell fluid pressure in the cell to reduce cross mixing between the catholyte and anolyte (and/or to perform any other suitable purpose); stop or have less electrolyte introduced (e.g., into the anode compartment and/or the cathode compartment) through the use of one or more pumps, variable pumps, valves, variable valves, droppers, dosing mechanisms, and/or any other suitable mechanism; and/or to otherwise vary operation of the cell to compensate for (and/or to otherwise attempt to correct) the high and/or other undesirable conductivity measurement.

In still other implementations, the cell is configured to (in near real time or otherwise): monitor amperage with the anode compartment and/or the cathode compartment and to automatically raise, lower, and/or to otherwise vary such amperage; monitor pressure within the anode compartment and/or the cathode compartment and to raise, lower, and/or to otherwise vary such pressure (e.g., by modifying variable pump speed, by varying a valve opening, by controlling a dropper and/or other electrolyte delivery device, and/or in any other suitable manner) to keep pressure within the cell at desired levels; monitor pH within the cell and to vary electrolyte levels, amperage, flowrates, introduction of a base and/or acid, and/or to otherwise modify cell operation to maintain a desired pH level in one or more portions of the cell; monitor flowrate and to increase, decrease, and/or otherwise vary flowrate to keep flowrate in the cell within a desired range; monitor temperature and to heat, cool, introduce cool fluid into, introduce hot fluid into, and/or to otherwise control temperature within the cell; monitor ORP of one or more solutions produced within the cell (e.g., the electrolyzed alkaline and/or electrolyzed oxidizing water) and to change cell operating amperage, increase and/or decrease an amount of electrolyte that is added to the cell, vary a flowrate of the electrolyte solution through the cell, and/or to otherwise vary cell operation; monitor electrolyte concentration in the anode compartment, the cathode compartment, and/or any other suitable portion of the system and to vary such concentration (e.g., via introduction of additional electrolyte through a dosing mechanism, a feeder, a valve, and/or in any other suitable manner; introduction of water and/or any other suitable diluent through a dosing mechanism, a feeder, a valve, and/or any in other suitable manner); and/or to otherwise monitor one or more characteristics of the cell and/or its contents and to vary cell operation and/or such contents based on the monitored readings.

Thus, in some implementations, the described electrolytic cell is configured to provide high-quality cleaning reagents under a wide variety of circumstances. For instance, some implementations of the cell are configured to automatically (and/or otherwise) modify cell operating conditions to account for: influent water with different characteristics (e.g., mineral content, temperature, pH, conductivity, and/or any other suitable characteristics); differing humidity levels, air pressures, temperatures, vibration levels, and/or other characteristics in places of the cell's operation; and/or any other suitable characteristic that can affect the cell's function and the quality of the product or products it produces.

Although in some cases, the cell is configured to provide information about its operating conditions to one or more users (e.g., via a display; lights; audible sounds; visual communications; wireless communications to a phone, tablet, computer, and/or any other suitable device; and/or in any other suitable manner), in some other cases, the system is configured to automatically and/or dynamically make adjustments to its operation parameters to produce desired products with desired characteristics. In some cases, the system is also configured to receive input regarding a desired product and to then automatically vary its operating parameters to produce the desired product. For instance, when a user indicates that a user would like an electrolyzed alkaline water and/or an electrolyzed oxidizing water to have a desired pH (or a pH in a desired range), the cell is configured to automatically modify its operating parameters (e.g., amperage, electrolyte dosing, electrolyte solution flowrate, and/or any other suitable parameter) to produce the desired product.

Some implementations of the described electrolytic cells are configured to automatically adjust their operating parameters to produce one or more products (e.g., electrolyzed alkaline water, electrolyzed oxidizing water, bleach, and/or any other suitable product) to have a wide range of characteristics. Indeed, in some cases, the described cells are configured to be able to automatically and selectively use one stream of feed water to produce electrolyzed alkaline waters (and/or electrolyzed oxidizing waters) having pHs that vary by more than about 0.25, 1, 2, 3, 4, 5, 6, or more pH units. In some cases, the described cells are configured to be able to automatically and selectively use one stream of feed water to produce electrolyzed alkaline waters (and/or electrolyzed oxidizing waters) having pHs that vary by more than 3 pH units (e.g., by more than 3.5 pH units).

The electrolytic cell can be any suitable size and can be configured to be used in any suitable location. Indeed, in some embodiments, the cell is configured to: fit within a vehicle (e.g., a van, truck, car, bus, tractor, forklift, trailer, and/or any other suitable vehicle), be placed on a skid, be worn as a backpack, roll around on a cart or with wheels, be located in one location and be used to fill containers with cleaning agents that are taken to various locations for use, and/or to be used in any other suitable manner.

Although in some implementations, the cathode compartment and the anode compartment are separated by one or more membranes, in some other implementations, the cell lacks a membrane between the two compartments. While such a cell can function in any suitable manner, in some cases, the cell is configured to move anolyte and catholyte past the corresponding electrodes at a relatively high rate of speed (e.g., at a rate that is variable based on: a strength of the solution or solutions being produced by the cell, the amperage of the cell, and/or any other suitable feature). Additionally, in some such embodiments, the cell comprises one or more spacer frames that are at least partially disposed between the anode and cathode compartments. In some such embodiments, the spacer frames comprise one or more channels and/or other topographic features that are configured to help mix and direct electrolytes past the corresponding electrodes.

Indeed, in accordance with some implementations, the electrolytic cell comprises an anode compartment comprising an anode; a cathode compartment comprising a cathode; a first spacer that is disposed between the anode compartment and the cathode compartment; a fluid inlet that is configured to channel an electrolyte solution to both the anode compartment and the cathode compartment; and a fluid outlet that is configured to combine and channel product from both the anode compartment and the cathode compartment. In some such implementations, the cell lacks an ion selective membrane that is disposed between the anode and cathode compartments. In some such cases, however, the anode and cathode compartments are at least partially separated by the spacer. Additionally, in some cases, the cell comprises a single fluid inlet, at one end of the cell, and a single fluid outlet, at an opposite side of the cell. Thus, in some embodiments, fluid (e.g., an electrolyte solution) flows through the inlet, into the cell, and into the two compartments, with the spacer serving (in some cases) to direct the fluid into the two compartments and/or across the corresponding electrode.

In some implementations, the cell is configured in such a manner that gas bubbles are configured to be removed from the anode and/or cathode to increase the effectiveness of such electrodes. In this regard, such gas bubbles can be removed in any suitable manner. Indeed, in some cases, the cell comprises one or more spacer frames that contact and/or that are otherwise in close proximity to a corresponding electrode, with the spacer frames each comprising a topography (e.g., raised features, lowered features, holes, channels, pores, and/or other topographical features) that is configured to churn and otherwise mix such fluids and to direct such fluids across the electrodes to help force gas bubbles off the electrodes and/or to constantly expose new portions of such fluids to the electrodes.

In some additional cases, the electrodes are directly in the flow path of the electrolyte solution into the anolyte and/or catholyte compartments. For instance, in some cases, one or more fluid inlets to the cell are disposed at a bottom end of the cell and one or more fluid outlets from the cell are disposed at a top of the cell. In some such cases, as fluids flow from the bottom end to the top end of the cell, the fluids help push gas bubbles off of the electrodes. In some cases, to further help off gassing from the electrodes and/or to ensure that most (if not all of the fluid is exposed to a surface of one of the electrodes, one or more electrodes is disposed directly in the flow path of one or more fluid inlets and/or outlets to the cell. As gas bubbles on the electrodes can (in some cases) make the electrodes less effective at forming ions, some embodiments of the described cell are configured to increase electrode productivity by aiding in cell off gassing.

In accordance with some implementations, the cell is further used with one or more sensors that are configured to determine a quality of water (and/or electrolyte solution) that is being added to the cell. In this regard, such sensors can identify magnesium, calcium, and/or other mineral levels; debris; bacteria; pathogens; and/or other undesirable materials in the water. In some such cases, the system is further configured such that when the sensors determine that influent's quality falls outside of one or more set parameters, the system is configured to stop the flow of water and/or the electrolyte solution into the cell (e.g., by closing a valve, diverting the fluids from flowing into the cell, and/or in any other suitable manner) and/or to stop the cell from functioning (e.g., by stopping or reducing the charge that is passed between the electrodes and/or in any other suitable manner). Thus, in some implementations, the described systems and methods are configured to prevent low quality water and/or electrolyte solution from causing undue damage to the electrodes (e.g., via scaling, pitting, etc.).

In some implementations, the described systems and methods comprise a wand (which can be used with the described systems and methods and/or with any other suitable systems and methods). In this regard, the described wand can comprise any suitable component or characteristic that allows it to be used to clean flooring (and/or any other suitable surface). Indeed, in some implementations, the wand includes a wand head and a vacuum tube.

With respect to the wand head, the wand head can comprise any suitable component that allows it to apply a fluid (e.g., electrolyzed water and/or any other suitable fluid) to a flooring surface and that allows the fluid to be sucked from the surface. Indeed, in some implementations, the wand head comprises a shroud that houses at least a portion of one or more jets, jet streams, and/or vacuum ports. While the jets and vacuum ports can be disposed in any suitable location, in at least some cases, the jets are disposed behind the vacuum port (e.g., closer to a user), such that the wand is configured to spray fluids and to suck up such fluids as the wand is pulled towards the user.

Additionally, in some cases, one or more of the vacuum ports include a breaker bar that is recessed within the shroud such that a portion of the shroud extends down past the breaker bar. Thus, in at least some implementations, the shroud is configured to form at least a partial seal with the flooring surface on which the shroud rests, and the shroud allows water and/or a cleaning agent that is sprayed from the jets to contact the flooring and to flow past the breaker bar and into the vacuum port.

In some implementations, the breaker bar's position is optionally adjustable within the shroud such that the breaker bar can be adjusted for flooring of a variety of textures and/or for any other suitable purpose. In such implementations, the breaker bar can be adjusted in any suitable manner, including, without limitation, via one or more threaded fasteners that are configured to be selectively tightened and loosened to respectively lock and release the breaker bar to and from a desired location.

In some implementations, the wand head comprises one or more air inlets that are configured to allow air to enter into the shroud when the shroud is forming a seal (or at least a partial seal) with a flooring surface (and/or any other suitable surface). While such inlets can perform any suitable function, in some embodiments, the inlets are sized, shaped, and placed to allow air to flow into the inlets to improve a spray pattern of the jets. Additionally, in some cases, the air inlets allow air to flow through the air inlets, across a surface being cleaned, then up into the vacuum tube while the shroud head is forming a seal with a surface that is being cleaned. As a result, in some such embodiments, the inlets allow the wand to provide high level of suction when the bottom surface of the shroud is in contact with a surface that is being cleaned.

In some implementations, the wand head is optionally coupled to one or more rollers that are configured to facilitate movement of the wand head across flooring and/or any other suitable surface. In such implementations, the roller is optionally adjustable such that the roller can be raised or lowered on the wand head to allow the wand to be adjusted for users of various heights while still allowing the shroud and/or wand head to make a partial (and/or complete) seal with the flooring (or other surface) that is being cleaned. As an additional feature, in some implementations, the roller (and/or a plurality of rollers coupled side to side) extends across a substantial width of the wand head. While such a roller (or rollers) can perform any suitable function, in some cases, they act to lay down a portion of carpet and/or other material that is being cleaned such that a larger portion of the strands of carpet (or other material) can be exposed to the spray and/or vacuum forces provided through the wand head.

With respect to the vacuum tube, the vacuum tube can comprise any suitable component or characteristic that allows a user to use the vacuum tube to direct the wand head and to allow liquids and/or debris sucked from the surface being cleaned to pass through the tube to a container, drain, and/or any other suitable depository.

In some implementations, the vacuum tube is shaped such that a user can easily slide the wand head across flooring (e.g., back and forth, side to side, and/or in any other suitable manner). In some implementations, however, the vacuum tube includes a first section that couples to the wand head, a second section that is configured to couple with a vacuum (e.g., via a hose or otherwise), and/or a third, elongated section that is disposed between the first section and the second section. Although, in some cases, the various sections are discrete sections that are joined together (e.g., via frictional engagement, mechanical engagement, threaded engagement, and/or in any other suitable manner), in other cases, the various sections are integrally formed together as a monolithic piece. In any case, while the various sections of the vacuum tube can have any suitable relation with respect to each other, in some implementations, a longitudinal axis of the first section runs at an angle between about 35 degrees and about 70 degrees (or within any subrange thereof, such as between about 40 degrees and about 44 degrees) with respect to a longitudinal axis of the third, elongated section, and the longitudinal axis of the third, elongated section runs at an angle between about 35 degrees and about 60 degrees (or within any subrange thereof, such as between about 41 degrees and about 45 degrees) with respect to a longitudinal axis of the second section.

The vacuum tube can also have any suitable inner diameter. Indeed, in some cases, the vacuum tube has an inner diameter that is between about 2 cm and about 8 cm (or any subrange thereof). For instance, some implementations of the tube have an inner diameter between about 4 cm and about 5 cm (e.g., about 4.445 cm). Accordingly, in some embodiments, the vacuum tube is easy to hold (e.g., fitting well within a user's hand) while being able to move relatively large amounts of air, fluids, and other materials through it.

In some cases, the wand head (or shroud) is swept forward with respect to the vacuum tube, such that a face and/or a longitudinal axis of the wand head runs at an angle that is not perpendicular with respect to a longitudinal axis of the first section. Indeed, in some cases, the front face and/or longitudinal axis of the shroud runs at an angle that is between about 89 degrees and about 60 degrees (or within any subrange thereof) with respect to the longitudinal axis of the first section.

In some implementations, in addition to and/or in place of the rollers, the wand head (e.g., the shroud) includes one or more skis, glides, or other lips that are configured to make it easier for a user to move the wand head across a flooring surface. While such a lip can be disposed in any suitable location (including, without limitation, at a lower front, rear, side, and/or any other suitable portion of the shroud), in some implementations, the lip is disposed at (and extends from) a lower back side of the shroud (e.g., a side of the shroud facing a user operating the wand) so as to allow a front side (and/or right or left sides) of the shroud to be pushed close to objects (e.g., a wall, furniture, and/or other objects) that are adjacent to and/or placed on the flooring. Additionally, while some implementations of the wand head comprise a lip but do not include any additional wheels or rollers, in some other implementations, the lower back side of the wand head comprise both a lip and one or more rollers.

In some implementations, the described wand further includes one or more filters. While such filters can be disposed in any suitable location, in some implementations, a filter is disposed on the wand adjacent to the wand head. In some other implementations, however, a filter is disposed on the vacuum tube closer to a trigger assembly than to the head. Accordingly, in some embodiments, the wand head is able to remain relatively light in weight (e.g., to help the head to easily slide across flooring surfaces).

In some implementations, the described systems and methods (and/or any other suitable systems and methods that produce or use electrolyzed water) comprise one or more magnets that are configured to improve the effectiveness of the cell and/or electrolyzed alkaline water and/or electrolyzed oxidizing water produced by the cell (e.g., by affecting minerals and/or their charge to help prevent the minerals in the water from plating out and/or precipitating and leaving residue on the electrolytic cell's electrodes, spacers, and/or ion permeable membrane (which can damage the membrane and/or reduce its effectiveness); by affecting minerals and/or their charge to help prevent the minerals from leaving residue on the surface being cleaned; by improving the ability of the electrolyzed water to penetrate cleaning surfaces and/or to dissolve dirt and/or other debris; and/or by otherwise improving the effectiveness of the system and/or its products). In this regard, the system can comprise any suitable type of magnet, including, without limitation, one or more neodymium magnets; neodymium iron boron magnets; aluminum nickel cobalt alloy magnets; samarium cobalt magnets; electromagnets; ceramic magnets; ferrite magnets; barium ferrite magnets; sintered composite magnets comprising powdered iron oxide and barium or strontium carbonate; magnetite magnets; lodestone magnets; magnets comprising gadolinium and/or dysprosium; iron alloy magnets; steel magnets; rare earth metal magnets; sintered magnets, cast magnets; plastic bonded magnets; isotropic magnets; anisotropic magnets; electronic de-scalers; magnets having a variable magnetic pole; and/or any other suitable type of materials or devices that have (or that are configured to have) magnetic properties (e.g., to produce a magnetic field). Indeed, in some cases, the described systems and methods comprise one or more rare-earth magnets.

Where the described system comprises one or more magnets, the magnets can be used in any suitable location that allows them to protect the cell and/or to improve the shelf life, the cleaning properties, and/or the effectiveness of the electrolyzed alkaline water and/or electrolyzed oxidizing water produced by the system. Indeed, in some implementations, the described systems comprise one or more magnets that are coupled to or that are otherwise associated with one or more: fluid inlets into an electrolytic cell (e.g., the described cell and/or any other suitable cell), compartments of the electrolytic cell, fluid outlets from the electrolytic cell, hoses to the wand (and/or a sprayer or other cleaning tool) and/or storage tank, the wand (and/or any other suitable wand), the wand head, the rollers, hosing to the wand, a storage tank, and/or any other suitable component of the described system. Indeed, in some embodiments, the described systems comprise one or more magnets (e.g., two opposing magnets) disposed at (and/or prior to) the fluid inlet into the electrolytic cell. In this regard, the magnets can be any suitable length, width, thickness, and/or diameter, including, without limitation, having one or more such measurements that are between about 0.001 cm and about 10 m (or any subrange thereof). Indeed, in some implementations, the magnets are between about 4 cm and about 40 cm (or any subrange thereof) in diameter. In some cases, the magnets are between about 3 mm and about 2 cm thick. In some additional cases, the described systems include multiple magnets that are disposed at different places along and/or within the inlet line.

In accordance with some implementations, the described systems and methods (and/or any other suitable system and/or methods) are configured to allow one or more fluids (e.g., electrolyzed alkaline water and/or electrolyzed oxidizing water) to flow past each other (and/or themselves) and/or to obtain a vortex flow to improve the shelf life, cleaning effectiveness, binding strength, chemical reactivity, the emulsifying characteristics, and/or any other suitable characteristic of the electrolyzed alkaline water and/or electrolyzed oxidizing water. In this regard, it is theorized that as one or more fluids (e.g., electrolyzed alkaline water, electrolyzed oxidizing water, and/or mixtures thereof) flow past each other and/or themselves, energy is passed (e.g., via electrons or otherwise) between the fluids; molecules in the fluids are caused to reorient as a result of interacting charges; and/or the fluids are otherwise modified to help them penetrate deeper into cleaning surfaces, to release dirt from cleaning surfaces, to hold on to debris, and/or to otherwise perform their cleaning and/or disinfecting functions more effectively.

Where one or more fluids (e.g., electrolyzed water) flow past each other or themselves (e.g., in the described system 10, in a conventional or novel electrolytic system, in a floor cleaning system, and/or in any other suitable location), the fluids can flow past each other in any suitable manner, including, without limitation, by flowing through tubing and/or any other suitable conduit that: is wrapped in a helix, is wrapped in a double helix, is wrapped in a triple helix, is coiled upon itself, includes multiple channels, twisted, has a portion of a fluid separated from another portion of the fluid by a single wall or membrane of the conduit, comprises internal features that cause the fluids to swirl and/or mix, comprises one or more inserts, and/or by otherwise running one portion of a conduit in proximity to another portion of the conduit (and/or another conduit) that comprises a fluid.

Indeed, in some implementations, the described systems and methods include conditioning electrolyzed water (e.g., electrolyzed alkaline water, electrolyzed oxidizing water, and/or mixtures thereof) by splitting the electrolyzed water solution into two streams; running a first stream of the electrolyzed water solution through a first conduit; running a second stream of the electrolyzed water solution through a second conduit (wherein a length of the first conduit and a length of the second conduit run in close proximity to each other); mixing the first and second streams of the electrolyzed water together to form a mixture; then applying the mixture to a material that is to be cleaned; and/or vacuuming up the mixture and debris from the material that is being cleaned. In some such implementations, the first and second conduits are twisted together.

In accordance with some other implementations, the described systems and methods relate to one or more cleaning agents that are configured to help improve cleaning processes. While the cleaning agent can comprise any suitable ingredient, in some cases, it includes sodium carbonate, sodium percarbonate, orange oil, orange peel terpene, citrus terpene, water, limonene, D-limonene, soy-based surfactants, soybean protein, and/or one or more: natural oil extracts, petroleum additives, bio organic materials, enzymes, synthetic materials, and/or any other suitable ingredient and/or ingredients.

The various ingredients in the cleaning agent can be present in the cleaning agent in any suitable concentration that allows the cleaning agent to be used to clean, pre-treat, and/or otherwise help remove stains, residue, and/or debris from any suitable surface or object. Indeed, in some cases, the various active ingredients in the cleaning agent (e.g., sodium carbonate, sodium percarbonate, orange peel terpene, soybean protein, etc.) are each present in the cleaning agent at concentration between about 0.1 and about 99% by molecular weight. In some embodiments, each of the active ingredients in the cleaning agent is present at between about 0.1% and about 60% by molecular weight (or within any subrange thereof). Indeed, in some implementations, an active ingredient is added to the cleaning agent at a concentration of between about 5% and about 30% by weight (e.g., at a concentration of about 20%±5%).

The cleaning agent can be used in any suitable manner, including, without limitation, by being sprayed on a surface (e.g., as a pre-spray for application of the electrolyzed water, being sprayed with the electrolyzed water, being applied to a surface after application of the electrolyzed water, and/or at any other suitable time), misted on a surface, wiped on a surface, painted on a surface, and/or otherwise applied to a surface or material. Indeed, in some implementations, the described cleaning agent is applied to a surface (e.g., flooring and/or any other suitable material) as a pre-spray (e.g., via a motorized sprayer, a hand pump sprayer, and/or in any other suitable manner). In some cases, after the cleaning agent has been applied (e.g., as a pre-spray), electrolyzed water, water, and/or a vacuum is used to rinse and/or otherwise remove the cleaning agent from the material that is being cleaned.

Some implementations of the described systems and methods relate to the addition of one or more chemicals to the electrolyzed alkaline water, the electrolyzed oxidizing water, and/or mixtures thereof. Indeed, in some cases, a natural agent is added to the electrolyzed alkaline and/or electrolyzed oxidizing water. In this regard, some non-limiting examples of materials that can be added to the electrolyzed alkaline water and/or electrolyzed oxidizing water include sodium carbonate, sodium percarbonate, orange peel terpene, soybean protein, and/or any other suitable natural agent.

In addition to (or in place of) the aforementioned ingredients, any other suitable ingredient can be added to the electrolyzed alkaline water and/or electrolyzed oxidizing water that is produced in accordance with the described systems and methods. In this regard, some non-limiting examples of such materials include, without limitation, one or more: natural oil extracts, petroleum additives, bio organic materials, enzymes, synthetic materials, and/or any other suitable ingredient and/or ingredients.

In accordance with some implementations, the described systems and methods include one or more disposable and/or reusable cloths, towels, towelettes, rags, swabs, mops, sponges, scrubbers, microfiber cloths, scouring pads, pieces of steel wool, pads, bandages, and/or other forms of cleaning implements or wipes that comprise electrolyzed alkaline water and/or electrolyzed oxidizing water. Indeed, in some cases, the wipes comprise cloth-like wipes that are partially wetted or saturated with electrolyzed water (e.g., electrolyzed alkaline water).

In some implementations, the described systems and methods include a package of cleaning implements, the package comprising multiple cleaning implements that each comprise an absorptive material; and an electrolyzed water solution, wherein the electrolyzed water solution is disposed within the absorptive material. In some such implementations, the cleaning implements are selected from wet wipes, sponges, cloths, brushes, towelettes, rags, swabs, mops, sponges, scrubbers, microfiber cloths, scouring pads, pieces of steel wool, and combinations thereof.

In addition to comprising electrolyzed alkaline water (and/or electrolyzed oxidizing water), the described wipes (or other cleaning implements) can comprise any other suitable ingredient that allows them to be used for any suitable cleaning purpose. Some non-limiting examples of such ingredients include one or more diluents, carriers, moisturizing agents, fragrances, surfactants (e.g., sodium diamphoacetate, coco phosphatidyl PG-dimonium chloride, and/or any other suitable surfactants), humectants (e.g., propylene glycol, glycerine, and/or any other suitable humectants that are capable of helping to prevent the wipes from drying out too quickly), coloring agents, alcohols, water, sterile water, deionized water, distilled water, reverse osmosis water, softened water, and/or other suitable ingredients.

Some implementations of the described systems and methods further relate to an agitator comprising two or more rug beaters, brushes, and/or other agitators that are configured to pull hair, dust, and other debris from surfaces being cleaned. Indeed, in some cases, the agitator comprises at least two brushes having relatively soft and/or stiff bristles, where the two brushes are substantially cylindrically shaped, and are configured to spin about an axis that runs substantially horizontally to a surface (e.g., flooring surface) being cleaned. In some such implementations, the brushes counter rotate. Indeed, in some cases, while a first brush can move clockwise, it can be selectively caused to rotate counterclockwise, with the second brushes' direction of rotation also being changed such that the brushes are counter rotating.

While the described systems and methods can be used in any suitable manner, in some embodiments, as a surface is cleaned: the surface is treated with a counter rotating brush device (e.g., to pull up debris from the surface being cleaned); a pre-treatment chemical (e.g., the cleaning agent discussed above) is applied to the surface (e.g., to loosen, break-up, sequester, emulsify, and/or otherwise treat debris on the surface), and/or an electrolyzed water solution (e.g., electrolyzed oxidizing water (or in some cases, electrolyzed alkaline water) that is made in accordance with the described systems and methods, including, without limitation by using a non-sodium chloride electrolyte like soda ash) is applied to and sucked from the material (e.g., via the described wand head).

While the devices, systems, and methods of the present invention may be particularly useful in the area of cleaning flooring, such as carpets, rugs, tile, stone, cement, brick, linoleum, wood, laminate, vinyl, rubber, mosaic, terracotta, glass, cork, and/or any other suitable type of flooring, those skilled in the art will appreciate that the described devices, systems, and methods can be used to clean any other suitable surface, including, without limitation, upholstery, furniture, draperies, blinds, walls, clothing, vehicle surfaces, operating room surfaces, bedding, and/or any other suitable surface.

These and other features and advantages of the present invention will be set forth or will become more fully apparent in the description that follows and in the appended claims. The features and advantages may be realized and obtained by means of the instruments and combinations particularly pointed out in the appended claims. Furthermore, the features and advantages of implementations of the invention may be learned by the practice of such implementations or will be obvious from the description, as set forth hereinafter.

BRIEF DESCRIPTION OF THE DRAWINGS

In order that the manner in which the above recited and other features and advantages of the present invention are obtained, a more particular description of the invention will be rendered by reference to specific embodiments thereof, which are illustrated in the appended drawings. Understanding that the drawings depict only representative embodiments of the present invention and are not, therefore, to be considered as limiting the scope of the invention, the present invention will be described and explained with additional specificity and detail through the use of the accompanying drawings in which:

FIG. 1G illustrates a schematic view of a concentrate cell chamber in accordance with a representative embodiment;

FIGS. 2A, 2B, and 2C respectively illustrate a front, side, and rear elevation view of a representative embodiment of a wand;

FIG. 3A illustrates a side elevation view of a representative embodiment of the wand;

FIG. 3B illustrates a front elevation view of a representative embodiment of a wand head;

FIG. 3C illustrates a back elevation view of a representative embodiment of the wand head;

FIG. 4A illustrates a side schematic view of a representative embodiment of the wand;

FIG. 4B illustrates a plan view of a representative embodiment of a roller;

FIG. 4C illustrates a back elevation view of a representative embodiment of the wand head;

FIGS. 12A-12E illustrate a different view hosing having two or more portions that are closely associated with each other in accordance with some embodiments;

FIGS. 12F-12H depict cross-section views of a conduit having an internal separator in accordance with some embodiments;

FIGS. 12Q-12R provide some experimental results obtained from conditioned electrolyzed water, in accordance with some embodiments;

DETAILED DESCRIPTION OF THE INVENTION

Figure 1A:
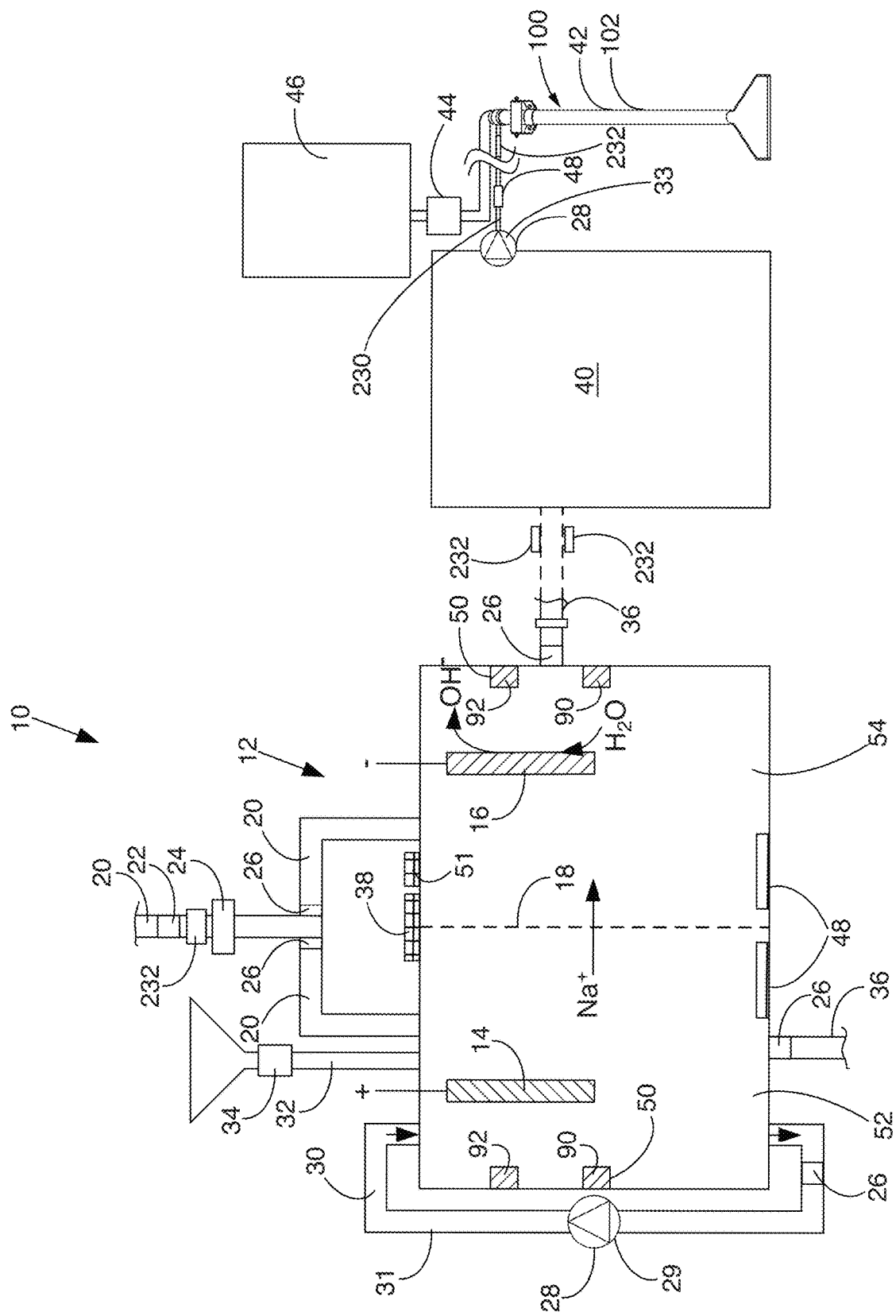
FIGS. 1A-1D each illustrate a schematic view of a different representative embodiment of a cleaning system that is configured to produce electrolyzed alkaline water and/or electrolyzed oxidizing water.

The present invention relates to systems and methods for cleaning materials and surfaces, such as flooring, furniture, drapery, upholstery, and any other suitable materials and surfaces. In particular, some implementations of the present invention relate to systems and methods for using an electrolytic cell to generate electrolyzed alkaline water and/or electrolyzed oxidizing water by electrolyzing a solution comprising sodium carbonate, soda ash, sodium bicarbonate, washing soda, soda crystals, crystal carbonate, sodium acetate, sodium percarbonate, potassium carbonate, potassium bicarbonate, sodium chloride, potassium chloride, and/or any other suitable salt and/or other electrolyte (e.g., any suitable electrolyte comprising one or more alkali ions). In some cases, the cell comprises a recirculation loop that recirculates anolyte through an anode compartment of the cell. In some cases, the cell further comprises a senor and/or a processor, where the processor is configured to automatically change an operation of the cell, based on a reading from the sensor. In some cases, a fluid flows past a magnet before entering the cell. In some additional cases, fluid from the cell is conditioned by being split into multiple conduits that run in proximity to each other. While the electrolyzed alkaline and/or electrolyzed oxidizing water can be used for any suitable purpose, in some implementations, they are used to clean and/or disinfect carpets, rugs, tile, stone, linoleum, flooring surfaces, furniture, walls, drywall, plaster, countertops, blinds, appliances, woods, metals, vehicles, upholstery, drapes, fabrics, clothing, cloth, bedding, beds, laminates, surfaces which are touched by humans (e.g., door knobs, handrails, chairs, tables, light switches, remote controls, windows, etc.), wounds, and/or any other suitable surface, object, or material In the disclosure and in the claims the terms surface, flooring, floor, flooring surface, and variations thereof, may refer to any suitable form of flooring, walls, carpet, rug, tile, stone, wood, slate, cement, laminate, vinyl, vinyl asbestos, plaster, metal, wood, mosaic, terracotta, terrazzo, ceramic, unglazed ceramic, brick, paver, porcelain, glass, cork, linoleum, rubber, grout, composite, synthetic, natural, cultured, and/or other floor surface, upholstery, furniture, draperies, blinds, walls, clothing, object, and/or material that can be cleaned and/or otherwise treated by the described electrolyzed water, wand, and/or other systems and methods.

The following disclosure of the present invention is grouped into seven subheadings, namely "Electrolytic System", "Electrolytes", "Wand", "Magnets", "Electrolyzed Water Conditioning", "Cleaning Agent", "Modified Electrolyzed Water", "Wipes and Cleaning Implements", "Counter Rotating Device", and "Representative Methods and Operating Environment". The utilization of the subheadings is for convenience of the reader only and is not to be construed as limiting in any sense.

Electrolytic System

In accordance with some embodiments, the described systems and methods comprise one or more electrolytic systems that are configured to produce an electrolyzed alkaline solution (e.g., electrolyzed alkaline water comprising NaOH and/or any other suitable base), an electrolyzed oxidizing solution (e.g., electrolyzed oxidizing water comprising HOCl and/or any other suitable acid), bleach, and/or any other suitable chemical that can be used for any suitable purpose, including, without limitation, for: cleaning and/or disinfecting floors, walls, countertops, living surfaces, ventilation systems, and/or any other suitable surface or material; washing clothes, textiles, and/or fabrics; washing furniture, drapes, and/or any other suitable object; sterilizing healthcare facilities; and/or for any other suitable purpose. In some embodiments, the described electrolytic system is configured to produce electrolyzed alkaline water (or alkaline water) for cleaning, electrolyzed oxidizing water (or oxidizing water) for disinfecting, bleach, and/or a variety of other chemicals. In some cases, as the electrolyzed alkaline water is used more than electrolyzed oxidizing water, the system is configured to produce more alkaline water than oxidizing water. Indeed, in some embodiments, the system is configured to produce relatively large amounts of alkaline water, while recirculating oxidizing water (and/or anolyte)

through the system to dramatically reduce the amount of oxidizing water that is produced (e.g., as compared to some competing devices).

While the described electrolytic system can comprise any suitable component that allows it to produce an electrolyzed alkaline solution, an electrolyzed oxidizing solution, and/or any other suitable product, FIG. 1A shows that in at least some embodiments, the electrolytic system 10 comprises one or more electrolytic cells 12, anodes 14, cathodes 16, ion exchange membranes 18, water inlets 20, filters 22, water softeners and/or other water treatment systems 24, valves 26, pumps 28, fluid mixers 30, electrolyte inlets 32, electrolyte feeders 34, fluid outlets 36, control systems 38, containers 40, dispensing tools 42, vacuums 44, waste tanks/drains 46, heaters 48, sensors 50, power supplies 51, and/or other suitable components.

In this regard, while the electrolytic system 10 can function in any suitable manner, in some embodiments, water and/or any other suitable solution ((e.g., a brine solution, a NaCl solution, and/or a non-NaCl solution), and/or any other suitable solution that allows for an electrolytic reaction to occur in the electrolytic cell 12) is added to an anode (or anolyte) compartment 52 and/or to a cathode (or catholyte) compartment 54. Indeed, although in some embodiments, water and an electrolyte (e.g., NaCl, $Na_2CO_3$, $NaHCO_3$, and/or any other suitable ionic substance) are added to both the anode and cathode compartments, in some other embodiments, water and one or more electrolytes (e.g., $Na_2CO_3$) are added to the anode compartment, while water is added to the cathode compartment. In some cases, current is then passed between the anode 14 and the cathode 16, such that the electrolyte is ionized to release alkali cations (e.g., $Na^+$, $K^+$, $Li^+$, and/or any other suitable cation), which are passed from the anode compartment 52, through the membrane 18, and to the cathode compartment 46. Additionally, as the as the cell operates, water is electrolyzed to create OH– and H+ ions. Thus, as cations (e.g., $Na^+$) leave the anode compartment, the solution in the anode compartment becomes acidic (e.g., forming an electrolyzed oxidizing solution comprising HOCl, and/or any other suitable chemical) and the solution in the cathode compartment becomes basic (e.g., forming an electrolyzed alkaline solution comprising sodium hydroxide (NaOH), and/or any other suitable chemical).

In some embodiments, the solution in the anode compartment 52 (or the anolyte) is optionally recirculated through the anode compartment (and/or in any other suitable manner) with additional electrolyte (e.g., soda ash and/or any other suitable electrolyte) being added as appropriate (e.g., as needed to produce a suitable amount (and/or desired concentration) of an electrolyzed alkaline solution in the cathode compartment). In some cases, however, a portion of the solution in the cathode compartment (e.g., the electrolyzed alkaline solution) is drained, pumped, and/or otherwise removed from the cathode compartment (e.g., for use in cleaning surfaces and/or any other suitable objects). By way of non-limiting illustration, FIG. 1A shows that, in some embodiments, electrolyzed alkaline water (not shown) is released from the cathode compartment 54 into a container 40 to then be applied to an object (e.g., carpet and/or any other suitable material) via one or more dispensing tools 42 (e.g., wands, sprayers, agitators, and/or other suitable dispensers). Indeed, in some embodiments, the electrolyzed alkaline solution is sprayed through a wand 100 to a desired object (e.g., flooring, walls, etc.) with the solution and debris then being sucked up through the wand (e.g., via the vacuum 48) to a waste tank 46 and/or a drain. To provide a better understanding of the described electrolytic system 10, some of the various optional elements of the system are described below in more detail.

With respect to the electrolytic cell 12, the electrolytic cell can have any suitable characteristic that allows it to function as described herein. For instance, the cell 12 and its various compartments (e.g., 52 and 54) and components can be any suitable size that allows the cell to function as described herein. By way of example, some embodiments of the cell have a footprint that is less than about 4 m by about 4 m (or within any subrange thereof). Indeed, some embodiments of the cell have a footprint that is less than about 1 m by about 1 m. For instance, some implementations of the cell have a footprint that is about 2 cm by about 0.76 m. Thus, while some embodiments of the cell are configured to be stationary, some other embodiments are configured to be mobile (e.g., carried by a truck, trailer, van, skid, cart, dolly, backpack, sling, and/or in any other suitable manner). Additionally, in some embodiments, the cell is easily configured to be used in homes, in vehicles, slings, backpacks, carts, wheeled structures, and/or in any other suitable manners and/or locations.

Additionally, the cell 12 can comprise any suitable material that allows it to function as described herein. Some non-limiting examples of such materials include one or more: metals or alloys (e.g., stainless steel, steel, carbon steel, titanium, and/or any other suitable metal), types of glass, plastics, polymers, ceramics, synthetic materials, and/or other suitable materials. In some embodiments, however, the cell comprises stainless steel.

With respect to the anodes 14 and cathodes 16, such electrodes 17 can comprise any suitable material that allows them to function as described herein to form electrolyzed alkaline, electrolyzed oxidizing water, and/or any other suitable chemical. In this regard, some examples of suitable electrode materials include, but are not limited to, one or more of the following: stainless steel; dimensionally stable anode materials; ruthenium coated on a conductive material; ruthenium oxide coated titanium, lead, tungsten, tungsten carbide, titanium diboride, nickel, cobalt, nickel tungstate, nickel titanate, graphite, ceramic electrode material, platinum, silver, titanium carbide, a porous electrode material, a foamed electrode material, and/or other suitable materials; and/or any other suitable electrode materials. Indeed, in some embodiments, the anode and/or cathode comprise stainless steel (e.g., stainless steel having one or more electrode coatings).

The anode 14 and cathode 15 can also have any suitable shape that allows them to function as described herein. Indeed, in some embodiments, the electrodes comprise one or more wires, plates, rods, meshes, blocks, screens, and/or any other suitable shape and configuration. By way of non-limiting illustration, FIGS. 1A and 1C show some embodiments in which the anode 14 and cathode 16 comprise a rod and/or block. In contrast, FIG. 1D shows an embodiment in which the anode 14 and cathode 16 each comprise a plate that has a relatively large amount of surface are on which electrolytic reactions can take place. Additionally, FIG. 1H shows an embodiment in which the electrode 17 (e.g., cathode and/or anode) comprises a coated object having a substantially flat surface. While such plates (and/or coated objects) can perform any suitable purpose, in some embodiments, the plates are configured to help hold the membrane 18 in place, while allowing for a continuous flow of fluid through the cell 12. Moreover, while such electrodes can perform any suitable function, including, without limitation, ionizing ionic materials in the electrolytes, FIG. 1K shows that, in some embodiments, the electrodes (not shown in FIG. 1K) form hexamer water clusters from normal water clusters (e.g., shown in 1J).

With respect to the ion exchange membrane 18, the cell 12 can comprise any known or novel ion exchange membrane and/or diaphragm that is suitable for use in the described system 10 and that is configured to allow alkali ions (e.g., $Na^+$ and/or any other suitable alkali ion) to be transferred from the anode compartment 52, through the membrane 18, and to the cathode compartment 54, while helping to separate the solutions in the anode and cathode compartments. In this regard, some non-limiting examples of suitable membranes comprise one or more porous membranes, non-porous membranes, NaSICON™ membranes, sodium ion and proton selective membranes, cation-permeable membranes, sodium phosphotungstate membranes, soda glass membranes, and/or other suitable cation permeable membranes. In some embodiments, however, the membrane comprises a non-porous, sodium selective membrane. With reference to the water inlets 20, the electrolytic cell 12 can receive water from any suitable source (including, without limitation, from one or more water tanks, potable water sources, non-potable water sources, irrigation water sources, distilled water, and/or other water sources) and can allow such water to be added to the anode compartment 52 and/or the cathode compartment 54 through one or more conduits, pipes, openings, spouts, valves, variable valves, variable speed pumps, and/or other inlets. Indeed, in some embodiments, potable water is added to the electrolytic cell through one or more inlets (e.g., an inlet for the anode compartment and an inlet for the cathode compartment). In some other embodiments, however, (e.g., as illustrated in FIG. 1G) a single fluid inlet 20 is configured to provided fluid (e.g., electrolyte) to both the anode compartment 52 and the cathode compartment 54.

Although, in some embodiments, water is added to the anode 52 and/or cathode 54 compartments manually, in some embodiments, water is added to the various compartments when a valve 26 is opened (e.g., manually and/or automatically, completely and/or partially), when a pump 28 is actuated (e.g., one or more desired pumping rates), and/or in any other suitable manner. Indeed, in some embodiments, the system 10 is configured to activate one or more valves and/or pumps (e.g., via the control system 38 and/or otherwise) to add more water (and/or electrolyte solution) to one or more compartments of the cell as needed. In this regard, as some embodiments of the cell are configured to recycle fluids through (and/or within) the anode compartment while fluids from the cathode compartment are used as cleaning agents, the described system is configured to selectively add water (and/or to allow water and/or an electrolyte solution to be selectively added) to the cathode compartment at a faster rate than an electrolytic solution (or the electrolyte and/or water) is added to the anode compartment.

With respect to the filters 22, the system 10 can comprise any suitable type and number of filters that allow debris, chemicals, and/or minerals to be removed from the water that is added into the cell 12. In this regard, some non-limiting examples of suitable filters include one or more screen filters, carbon filters, activated carbon filters, reverse osmosis filters, membrane filters, mechanical filters, ultra-violet light filters, deionization filters, paper filters, and/or any other suitable type of filter.

With respect to the water softeners and/or other water treatment systems 24, the system 10 can be used with any suitable system that is capable of softening and/or otherwise treating water that is introduced into the cell 12. Indeed, in some embodiments, the described system comprises one or more ion-exchange polymer systems; salt, water softeners; magnets (e.g., permanent magnets, electromagnets, temporary magnets, etc.); reverse osmosis systems; water distillation systems; and/or other suitable water treatment systems. In some embodiments, however, the system comprises a water softening system. Where the water treatment system 24 is configured to soften the water, the water can be softened to have any suitable water hardness measurement. Indeed, in some embodiments, the water treatment system is configured to cause water that is supplied to the cell 12 to have less than about a 15 grain hardness (or any lower level). In some cases, for instance, the water treatment system is configured to provide the water introduced into the cell to have less than a 2.0 grain hardness (e.g., less than a 1.0 grain hardness).

In accordance with some embodiments, the cell 12 is used with one or more sensors 50 that are configured to determine a quality of water (and/or electrolyte solution) that is being added to the cell. In this regard, such sensors can identify magnesium, calcium, and/or other mineral levels; debris; bacteria; pathogens; grain hardness; and/or other undesirable materials in, or characteristics of, the water. In some such cases, the system 10 is configured such that when the sensors determine that influent's quality falls outside of one or more set parameters (e.g., it is too hard), the system is configured to stop the flow of water and/or the electrolyte solution into the cell (e.g., by closing a valve, diverting the fluids from flowing into the cell, and/or in any other suitable manner) and/or to stop the cell from functioning (e.g., by stopping or reducing the charge that is passed between the electrodes and/or in any other suitable manner). Thus, in some embodiments, the described systems and methods are configured to prevent low quality water and/or electrolyte solution from causing undue damage to the electrodes 17 (e.g., via scaling, precipitation, hard water build up, pitting, etc.).

Turning now to the valves 26, the system 10 can comprise any suitable type and number of valves that allows the system to selectively: add water and/or electrolyte solution to the anode 52 and/or cathode 54 compartments; add electrolyte to the anode 52 and/or cathode 54 compartments; allow fluid to flow from the anode and/or cathode compartments; allow fluid to be recirculated through the anode compartment; allow fluid from the anode compartment to be used outside of the cell (e.g., for sanitization, to be sent to a drain, to be sent to a tank, and/or to be sent to any other suitable location); allow fluid from the cathode compartment to flow to the container 40, a drain, and/or any other desired location; allow the system to switch between sending water and sending an electrolytic solution (e.g., an NaCl solution and/or any other electrolyte) to the cathode compartment; allow the system to switch from sending a first electrolyte solution (e.g., an aqueous solution comprising $Na_2CO_3$) to sending a second electrolyte solution (e.g., an aqueous solution comprising NaCl) to the anode compartment; to vary a speed at which fluids (e.g., anolyte, catholyte, electrolyte, products, etc. pass through and/or are added to the anode and/or cathode compartments; vary pressure within one or more compartments of the cell; increase and decrease pressures in the anode and cathode compartments, while keeping such pressures substantially equal; slow and/or prevent fluids and/or gases from moving through (and/or out of) the system; venting one or more portions of the system; and/or to otherwise allow the system to function as described herein.

Indeed, in some embodiments, the valves 26 allow electrolyzed alkaline water to be selectively released from the system 10. In some other embodiments, the valves are configured to be selectively switched to stop the release of electrolyzed alkaline water while allowing the flow of electrolyzed oxidizing water (e.g., for sanitization and/or any other suitable purposes). In still other embodiments, the valves are configured to be selectively controlled to simultaneously release electrolyzed alkaline water and electrolyzed oxidizing water in any suitable amounts or any suitable volume ratios with respect to each other. In still other embodiments, one or more valves, pumps, dosing mechanisms, and/or other suitable mechanisms are configured to selectively and/or automatically add additional electrolyte to one or more compartments of the cell (e.g., the anolyte compartment).

Where the system 10 comprises one or more valves 26, the valves can be disposed in any suitable location or locations that allow the system to function as described herein. By way of non-limiting illustration, FIG. 1A shows that in at least some embodiments, the system 10 comprises one or more valves 26 on: the fluid inlets 20 to the anode and cathode compartments (52 and 54), the fluid outlets 36 from such compartments, the recirculation line 31 (discussed below) of the anode compartment 52, and/or in any other suitable location. Additionally, while FIG. 1A shows that in some embodiments (as discussed below) the system 10 comprises one or more electrolyte feeders 34, in some embodiments, such feeders (or feed mechanisms) comprise a valve, a pump, auger, conveyor, dosing mechanisms, and/or any other suitable mechanism that is configured to deliver electrolyte and/or an electrolyte solution to the cell.

Figure 1B:
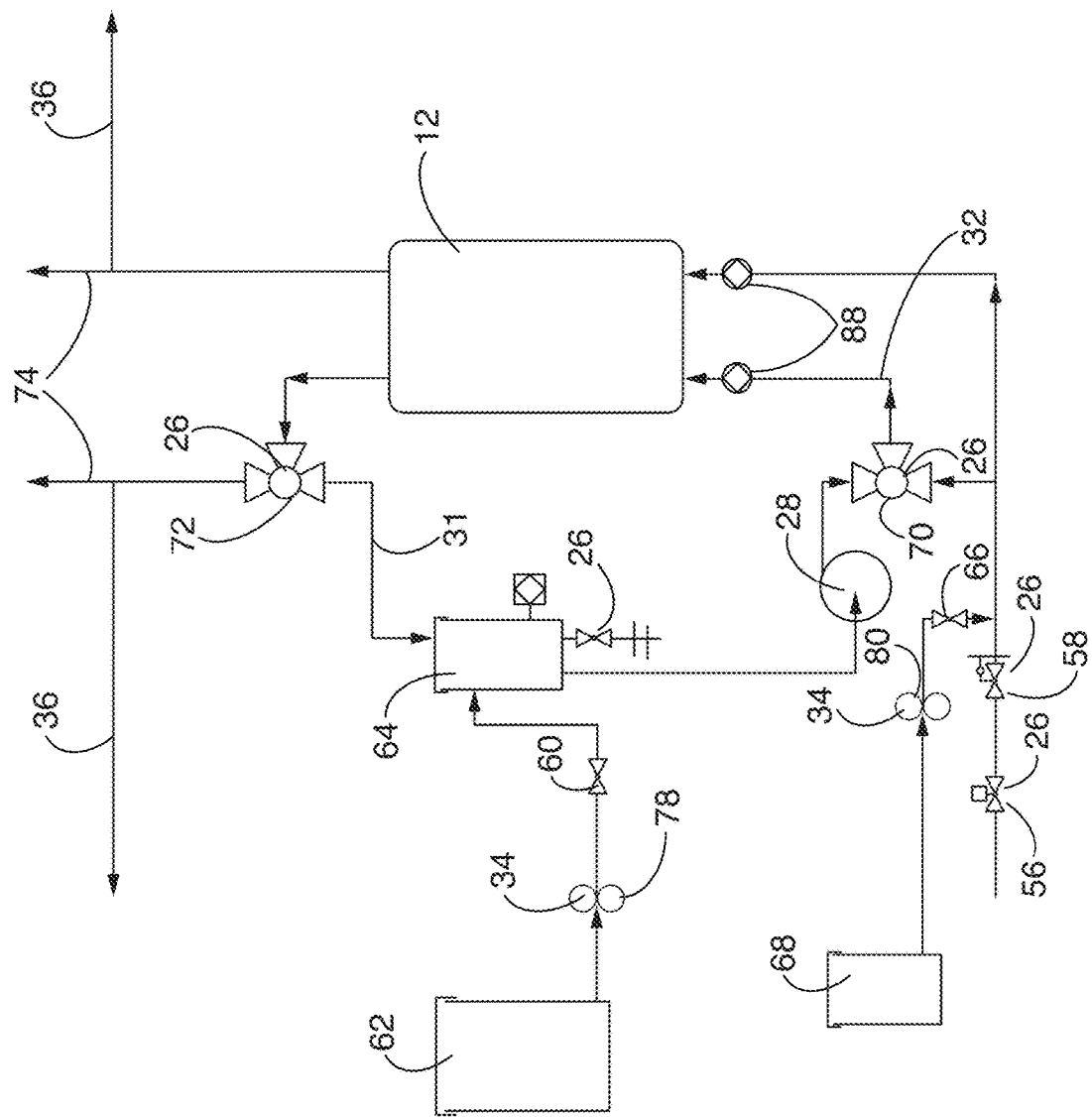
Figure 1C:
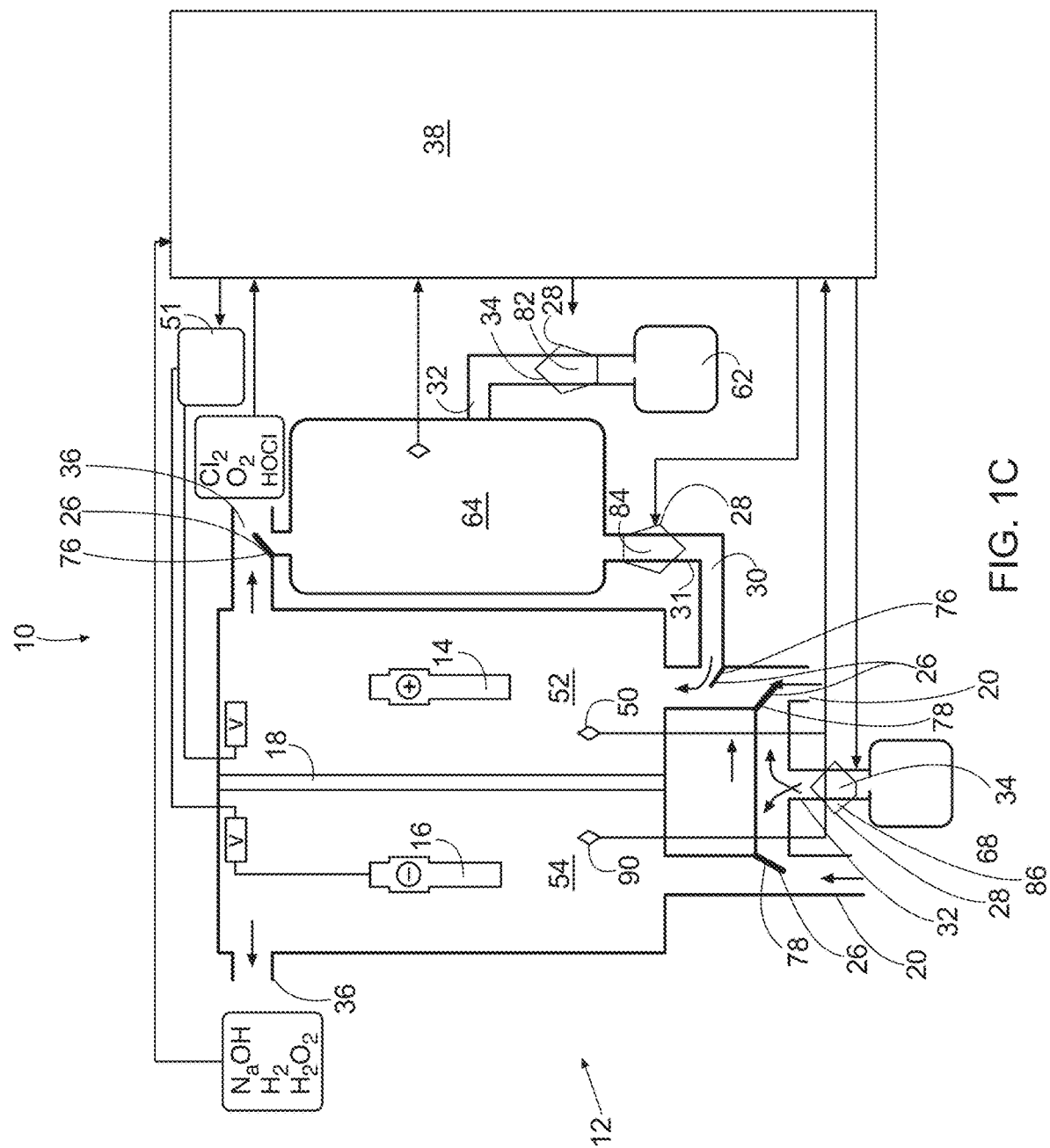
Figure 1D:
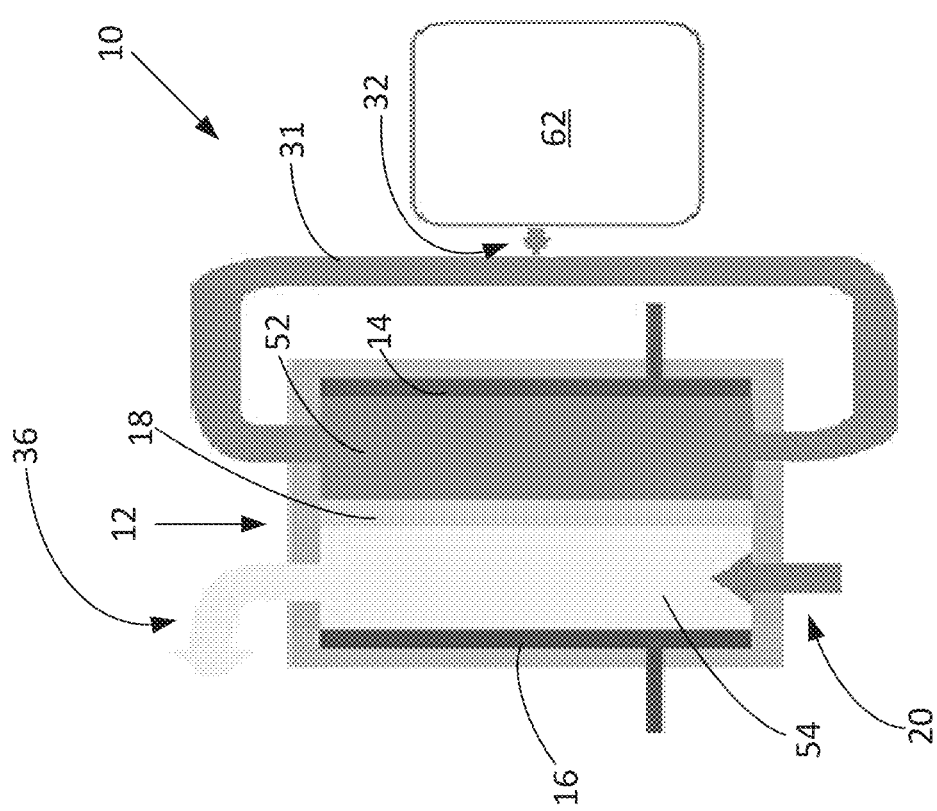

In another non-limiting illustration, FIG. 1B shows an embodiment in which the system 10 comprises a first valve 56 (e.g., a solenoid, a variable valve, and/or any other suitable valve) and a second valve 58 (e.g., a pressure regulating, a variable valve, and/or any other suitable valve) to control an amount, timing, and pressure of water (e.g., zero hardness potable water and/or any other suitable water) that flows into the cell 12. Again, in some embodiments, such valves are controlled by one or more sensors and/or the control system 38 and/or any other suitable processor. In any case, FIG. 1B also shows that in some embodiments, the system 10 optionally comprises a valve 60 (e.g., a variable valve, a mechanically controlled valve, and/or any other suitable valve) that is configured to control the introduction of a first electrolyte and/or electrolyte solution (e.g., an aqueous solution comprising $Na_2CO_3$ from a storage tank 62) into the anode compartment (e.g., via an anolyte recirculation tank 64). Additionally, FIG. 1B shows that some embodiments of the system 10 comprise yet another valve 66 that is configured to control the introduction of a second electrolyte and/or electrolytic solution (e.g., an aqueous solution of NaCl from a tank 68) into the anode compartment and/or cathode compartment of the cell 12. Thus, in some embodiments, the system is configured to switch between using a first electrolyte solution (e.g., a $Na_2CO_3$ solution) in the anode compartment (e.g., with water in the cathode compartment) to using a second electrolyte solution (e.g., a NaCl solution) in the anode and/or cathode compartment (and/or to using a combination thereof).

Continuing with FIG. 1B, that figure shows that, in at least some embodiments, the system 10 comprises one or more valves 26 (e.g., a first three-way valve 70, a variable valve, and/or any other suitable valve or valves) that controls (at least partially): (a) the flow or recirculation of anolyte through the anode compartment and/or (b) the flow of water (e.g., softened, potable water) and/or a second electrolyte solution (e.g., an aqueous NaCl solution) into the cell. Additionally, FIG. 1B shows that, in some embodiments, another valve (e.g., a second three-way valve 72, a variable valve, and/or any other suitable valve or valves) controls (at least partially): (a) recirculation of the anolyte through the anode compartment, (b) release of gases through a vent 74, and/or (c) release of fluids (e.g., anolyte) through a discharge line 36.

In still another non-limiting illustration, FIG. 1C shows that, in some embodiments, the system 10 comprises one or more valves 76 that at least partially control recirculation of the anolyte through the anode compartment 52. Additionally, FIG. 1C shows that, in some embodiments, the system 10 comprises one or more additional valves 26 that control (and/or prevent) the flow and/or flowrate of a second electrolyte solution (e.g., a NaCl solution) into the anode compartment 52 and/or the cathode compartment 54.

While the system 10 can comprise any suitable type of valve 26, some examples of suitable valves include, but are not limited to, one or more variable valves, manual valves, automated valves, motorized valves, powered valves, solenoid valves, ball valves, butterfly valves, gate valves, check valves, actuated valves, and/or any other suitable valves. Again, while one or more of the valves are manually operated in some embodiments of the system, in some other embodiments, one or more valves are configured to be automated (e.g., controlled by one or more processors of the control system 38). Accordingly, in some such embodiments, the described system can automatically adjust its operating parameters based on any suitable element (e.g., as discussed below), including, without limitation, based on the quality or characteristics of the water being fed into the cell 12, the conductivity of one or more solutions in the cell, the flowrate of one or more fluids through the cell, and/or any other suitable feature.

With respect to the pumps 28, the system 10 can comprise any suitable type and number of pumps, in any suitable locations, that allow the system to produce electrolyzed alkaline water and/or electrolyzed oxidizing water. In this regard, the pumps can perform any suitable process, including, without limitation, forcing one or more fluids and/or gases through the system, preventing one or more fluids or gases from moving through the system, increasing and/or decreasing a rate at which materials flow though the cell, varying pressure within the cell, introducing materials (e.g., electrolyte, electrolyte solution, water, and/or any other suitable material) into the cell, and/or functioning with (and/or in place of) one or more valves 26 and/or dosing or feeder mechanisms.

Some non-limiting examples of suitable pumps 28 include one or more variable speed pumps; magnetic drive pumps; AC pumps; DC pumps; peristaltic pumps; positive displacement pumps; negative displacement pumps; piezoelectric pumps; manual pumps; motorized pumps; piston pumps; fixed displacement piston pumps; axial piston pumps; radial pumps; reciprocating pumps; plunger pumps; roots blowers; pumps that are configured to increase pressure within the cell 12, the container 40, and/or any other suitable location to thereby force fluid from or through the system; centrifugal pumps; rotary pumps; vane-type pumps; diaphragm pumps; multi-stage pumps; variable speed pumps; wringers (e.g., one wheel that pinches a portion of the a flexible bladder against another wheel or other object in which at least one wheel is configured to roll to force fluid from the bladder); and/or any other suitable mechanism that is capable of forcing and/or drawing fluid (and/or any other suitable material) within or from any suitable portion of the system. In some embodiments, the pumps comprise one or more mag drive pumps and/or variable speed pumps. In this regard, in accordance with some such embodiments, magnetic drive pumps lack shaft seals, which can leak.

In some embodiments, the pumps 28 are configured to selectively move (manually and/or automatically) one or more fluids into and/or out of the anode compartment 52, the cathode compartment 54, one or more storage containers 40, one or more dispensing tools 42, one or more drains, an electrolyte container 62 that comprises a first electrolyte and/or a first electrolyte solution (e.g., a $Na_2CO_3$ solution), another electrolyte container 68 that comprises a second electrolyte and/or a second electrolyte solution (e.g., a NaCl solution), an anolyte recirculation tank 64, and/or other suitable portion of the system. Again, while such pumps can be disposed in any suitable location, FIG. 1A shows an embodiment in which a pump 28 (e.g., pump 29) is used to recycle fluid (e.g., anolyte) in the anode compartment 52 and another pump (e.g., pump 33) is used to move fluid (e.g., electrolyzed alkaline water) from the container 40 to a dispensing tool 42. Additionally, FIG. 1B shows an embodiment in which a first 78 and second 80 pump respectively move a first (e.g., a $Na_2CO_3$ solution) and second (e.g., a NaCl solution) electrolyte solution from the first 62 and the second 68 electrolyte containers to the cell 12.

FIG. 1C shows that, in some embodiments, the system 10 comprises: (a) a first pump 82 that is configured to selectively move a first electrolyte (e.g., $Na_2CO_3$, a solution comprising $Na_2CO_3$, and/or any other suitable electrolyte) from the first electrolyte tank 62 into the anolyte recirculation tank 64 and/or the anode compartment 52; (b) a second pump 84 that is configured to selectively recirculate fluids (e.g., anolyte) through the anode compartment 52 and/or the anolyte recirculation tank 64; and/or (c) a third pump 86 that is configured to selective move a second electrolyte (e.g., NaCl, a NaCl solution, and/or any other suitable electrolyte) from a second electrolyte container 68 to the anode 52 and/or cathode 54 compartments. Again, it should be noted that the various pumps, valves, dosing mechanisms, and feeders discussed herein, can be interchanged and replaced with any other suitable component that allows the cell to produce electrolyzed water and/or to otherwise function as described herein.

Turning now to the fluid mixers 30, some embodiments of the system 10 comprise one or more fluid mixers in the anode compartment 52, the cathode compartment 54, and/or the anolyte recirculation tank 64 that are configured to mix fluids within such containers. Thus, in some embodiments, the mixers help keep electrolyte and/or ion concentrations substantially homogeneous within the anode and/or cathode compartments, mix electrolytes into solution in one or both of the compartments (e.g., the anode compartment), help speed chemical reactions within the cell, cause gas bubbles to be off gassed, to improve cell electrolysis efficiency, and/or to otherwise help the cell 12 to perform its intended functions.

The system 10 can comprise any suitable type of fluid mixers 30, including, without limitation, one or more magnetic stirrers, impellers, mixers, blades, turbines, pumps 28, inlets, outlets, cyclo mixers, recirculation lines, circulation pumps, jets, spacer frames, agitators, and/or other suitable mixing mechanisms. By way of non-limiting illustration, FIGS. 1A-1C show some embodiments in which the mixer 30 comprises one or more recirculation lines 31 and/or pumps 28 that are configured to cause fluid in the anode compartment 52 to be mixed as fluid is recirculated through the compartment. Additionally, in some embodiments, the electrolyte storage tank 62 comprises one or more agitators and/or any other suitable mixing mechanisms that are configured to mix materials (e.g., anolyte) that are within the storage tank.

With reference now to the electrolyte inlets 32, one or more electrolytes can be added to the anode 52 and/or cathode 54 compartments in any suitable manner, including, without limitation, manually and/or automatically. In some embodiments, an electrolyte solution is added directly to the cell 12 (e.g., the anode compartment and/or to the cathode compartment, in some embodiments). In some other embodiments, water and/or an electrolyte solution is added to the cell, and then additional electrolyte is added (e.g., as a powder, solid, liquid, gel, liquid, and/or otherwise) to the cell as needed (e.g., as electrolyte concentration drops in the anode and/or cathode compartments). In some embodiments, the system 10 comprises one or more electrolyte inlets that are configured to direct electrolytes into a compartment of the cell. By way of non-limiting illustration, FIGS. 1A-C show some embodiments in which the anode compartment 52, the cathode compartment 54, and/or the cell 12 comprise one or more electrolyte inlets 32.

In some embodiments, the system 10 comprises one or more electrolyte feeders 34 that are configured to add electrolyte to the anode compartment 52 (and/or, in some cases, cathode compartment 54). Specifically, FIGS. 1A-1C show that, in some cases, the system 10 comprises an electrolyte feeder 34 that is configured to add a first electrolyte (e.g., $Na_2CO_3$ and/or any other suitable electrolyte) to the anode compartment 52 and/or the anolyte recirculation tank 64. Similarly, FIGS. 1B and 1C show some embodiments in which the system 10 comprises an electrolyte feeder 34 to provide a second electrolyte (e.g., NaCl and/or any other suitable electrolyte) to the anode compartment 52 and/or the cathode compartment 54.

Where the system 10 comprises one or more electrolyte feeders 34, the feeders can comprise any suitable mechanism that is configured to add electrolyte to the cell 12. Some examples of suitable feeders comprise one or more peristaltic pumps, valves 26, pumps 28, injectors, augers, droppers, mechanized electrolyte delivery systems, dosing mechanisms, and/or other mechanisms that are configured to add electrolyte to the cell (e.g., to the anode compartment or elsewhere). Indeed, in some embodiments, the feeder comprises one or more pumps 28 (e.g., as shown in FIGS. 1A-C). In any case, the feeder can be controlled in any suitable manner, including, without limitation, manually and/or automatically (e.g., via the control system 38 or otherwise). Indeed, in some embodiments, the feeder comprises one or more meters that are configured to inject (and/or otherwise provide) specific amounts of the electrolyte into the cell (either directly or indirectly) to obtain electrolyzed water (e.g., alkaline and/or oxidizing) with one or more desired characteristics. Additionally, in some embodiments (and as discussed below) when the system determines that the amount of electrolyte in the solution should be changed to produce a desired product and/or to compensate for one or more other variables in the system's operation, in some embodiments, the feeders are configured to automatically (e.g., with a the control system and/or sensors 50) to vary the amount of electrolyte in the system.

With reference now to the fluid outlets 36, the system 10 can comprise any suitable number of fluid outlets that are disposed in any suitable location or locations that allow fluid to be transferred from the anode compartment 52 and/or the cathode compartment 54 to any suitable location. Indeed, in some embodiments, the fluid outlets are configured to allow the system to selectively send electrolyzed alkaline water and/or electrolyzed oxidizing water to any suitable location, including, without limitation, to a container (e.g., container 40 in the case of the electrolyzed alkaline water), to a dispensing tool 42, to a drain, the anode compartment 52, and/or to any other suitable location.

With reference now to the sensors 50, the system 10 can comprise any suitable type and number of sensors that allows the system to produce electrolyzed alkaline water, electrolyzed oxidizing water, and/or any other suitable product. Some non-limiting examples of such sensors are pH sensors, conductivity sensors, flowrate sensors, flow meters, fluid flow sensors, fluid velocity sensors, fluid level sensors, electrolyte concentration sensors, temperature sensors, voltage sensors, current sensors, pressure sensors, ion selective sensors, electrical sensors, electrical potential sensors, electrochemical sensors, hydrogen sensors, scales, water purity sensors, water quality meters, oxidation reduction potential ("ORP") meters, redox sensors, magnesium sensors, calcium sensors, water hardness sensors, and/or any other suitable sensors, disposed in any suitable location (including, without limitation, at or prior to the inlets 20, within the anode compartment 52, within the cathode compartment 54, in the circulation line 32, in a storage tank 40, in the recirculation tank 64, at the outlets 36, and/or in any other suitable location).

Indeed, in some embodiments, the anode compartment 52 comprises one or more pH sensors, conductivity sensors, flowrate sensors, and/or electrochemical sensors that are configured to determine when more electrolyte and/or water need to be added to the anode compartment 52. Similarly, in some embodiments, the cathode compartment 54 comprises one or more pH sensors, conductivity sensors, flowrate sensors, and/or electrochemical sensors that are configured to help the system determine when fluid in the cathode compartment (or the catholyte) has reached a desired pH and/or concentration of NaOH, when electrolyzed alkaline water should be released from the compartment, when water should added to the compartment, and how operating conditions of the system can be modified to provide the desired chemicals. By way of non-limiting illustration, FIGS. 1A-C show some embodiments in which the system 10 comprises one or more flow meters 88, electrical conductivity sensors 90, fluid level sensors 92, and/or other suitable sensors (e.g., flow sensors, voltage sensors, current sensors, etc.).

In some embodiments, the cell 12 comprises one or more conductivity sensors amperage sensors, concentration sensors, flowrate sensors, pH sensors, and/or other suitable sensors 50. In some such embodiments, when the cell determines that conductivity of the electrolyte solution is below a desired threshold (e.g., because the solution does not have enough electrolyte, the amperage is too low, the pH is not in a desired range, and/or for any other suitable reason), the cell is configured to: increase the operating amperage of the electrodes (e.g., to increase ion formation); modify the flowrate of electrolyte solution through the cell (e.g., through the anode compartment and/or any other suitable portion of the cell, so as to give the electrolyte more time to react and/or ionize); decrease fluid pressure in the cell (e.g., in both the anode and cathode compartments to maintain substantially equal pressure between the compartments) to allow the electrolyte to ionize and/or otherwise react more effectively; have more electrolyte introduced (e.g., into the anode compartment and/or the cathode compartment, as applicable) through the use of one or more pumps, variable pumps, valves, variable valves, droppers, dosing mechanisms, and/or any other suitable mechanism (e.g., feed mechanism 34); and/or to otherwise vary operation of the cell to compensate for (and/or to otherwise attempt to correct) the low conductivity measurement. Indeed, in some embodiments, in which the system 10 determines that conductivity of one or more solutions in the system are below (or otherwise fall outside of a set range), the system is configured to modify (automatically and/or otherwise) the electrode's operating amperage and/or the amount of one or more electrolytes that are added to one or more compartments of the cell.

In some cases, when one or more sensors 50 determine that: the conductivity level of the electrolyte solution in the cell 12 (e.g., in the anode compartment and/or the cathode compartment) is above a desired level; amperage is in the cell is too high; a flowrate is too low; a pH of the anolyte and/or catholyte is outside of a desired range; an electrolyte concentration in the cell is too high; and/or that some other parameter of the cell's operation is outside of a set range, some embodiments of the cell are configured to: decrease the operating amperage of the electrodes (e.g., to decrease ion formation); increase the flowrate of electrolyte solution through the cell (e.g., through the anode compartment and/or any other suitable portion of the cell, so as to give the electrolyte less time to ionize and/or otherwise react); increase fluid pressure in the cell (e.g., in both the anode and cathode compartments, to keep pressures in the compartments substantially similar) to reduce ionization; stop or have less electrolyte introduced (e.g., into the anode compartment and/or the cathode compartment) through the use of one or more pumps, variable pumps, valves, variable valves, droppers, dosing mechanisms, and/or any other suitable mechanism; and/or to otherwise vary operation of the cell to compensate for (and/or to otherwise attempt to correct) the high conductivity measurement. In still other embodiments, the cell is configured to: monitor pressure within the anode compartment 52 and/or the cathode compartment 54 and to raise, lower, and/or to otherwise vary such pressure (e.g., by modifying variable pump speed, by varying a valve opening, by controlling a dropper, by controlling a feed mechanism 34, any other suitable electrolyte delivery device, and/or in any other suitable manner) to keep pressure within the cell at desired levels; monitor pH within one or more portions of the cell and to vary electrolyte levels, amperage, flowrates, introduction of a base and/or acid, and/or to otherwise modify cell operation to maintain a desired pH level in one or more portions of the cell; monitor flowrate and to increase, decrease, and/or otherwise vary flowrate to keep flowrate in the cell (and/or various portions of the cell) within a desired range; monitor temperature and to heat, cool, introduce cool fluid into, introduce hot fluid into, and/or to otherwise control temperature within the cell and/or any portion thereof; monitor ORP of one or more solutions produced within the cell (e.g., the electrolyzed alkaline and/or electrolyzed oxidizing water) and to change cell operating amperage, increase, and/or decrease an amount of electrolyte that is added to the cell, vary a flowrate of the electrolyte solution through the cell, and/or to otherwise vary cell operation; and/or to otherwise monitor one or more characteristics of the cell and/or its contents and to vary cell operation and/or such contents based on the monitored readings.

Thus, in some embodiments, the described electrolytic cell 12 comprises one or more feedback loops (e.g., closed feedback loops) that allow the control system 38 to monitor and control cell operation and production. Additionally, in some cases, the system is configured to provide high-quality cleaning reagents under a wide variety of circumstances. For instance, some embodiments of the cell are configured to modify cell operating conditions to account for: influent water with different characteristics (e.g., mineral content, temperature, pH, conductivity, and/or any other suitable characteristics); differing humidity levels, air pressures, temperatures, vibration levels, and/or other characteristics in places of the cell's operation; and/or any other suitable characteristic that can affect the cell's function and the quality of the product or products it produces.

Although in some cases, the system 10 and/or cell 12 is configured to provide information about its operating conditions to one or more users (e.g., via one or more displays; lights; audible sounds; visual communications; wired communications; wireless communications to a phone, tablet, computer, and/or any other suitable device; and/or in any other suitable manner), in some other cases, the system 10 is configured to automatically and/or dynamically make adjustments to its operation parameters to produce desired products with desired characteristics. In some cases, the system is also configured to receive input regarding a desired product and to then automatically vary its operating parameters to produce the desired product. For instance, when a user indicates that a user would like an electrolyzed alkaline water and/or an electrolyzed oxidizing water with a desired pH (or a pH in a desired range), the cell is configured to automatically modify its operating parameters (e.g., amperage, electrolyte dosing, electrolyte solution flowrate, and/or any other suitable parameter) to produce the desired product.

Thus, in some embodiments, a user can quickly and simply modify the products being produced by the cell (e.g., by selecting desired products, selecting desired characteristics, setting a program, and/or in any suitable manner) without the user having to manually open and close valves in the cell, increase or decrease amperage between the electrodes 17, add and/or slow the addition of electrolyte into the cell, and/or otherwise manually control the cell. Indeed, while some embodiments of the system 10 are configured to be controlled by an operator (e.g., manually and/or via an automated method, as controlled by the operator), in some other embodiments (as mentioned previously), the system comprises one or more control systems 38 that are configured to help control the system's operation. In this regard, the control system can comprise any conventional or novel processor and/or control system that is suitable for use with the system, and that is configured to allow the system to function as described herein. In this regard, some embodiments of a suitable control system are described below in the section entitled Representative Methods and Operating Environment.

In some embodiments, the control system 38 is configured to operate the system 10 in accordance with one or more pre-set settings. In some other embodiments, the control system is in signal communication with one or more controls (e.g., keyboards, key pads, switches, user interfaces, touch screens, controllers, joysticks, personal computers, timers, servers, apps, smart phones, handheld computers, computers (onsite and/or offsite), and/or other suitable controls) that allow the system's operation to be modified, either manually and/or automatically (e.g., for different water sources, for different cleaning applications, to use different electrolytes, to modify fluid concentrations, to modify and/or select products produced by the cell, and/or for any other suitable purpose).

In some embodiments, the control system 38 is also in signal communication with one or more of the sensors 50. Thus, in some embodiments, the control system is able to modify operation of the system 10 based on sensor readings. By way of non-limiting example, some embodiments of the control system are configured to cause the system (e.g., via user controls, one or more programs, as directed by the operator, and/or in any other suitable manner) to: add more electrolyte, water, and/or any other suitable material to the anode compartment 52 (and/or elsewhere) as needed to produce desired product; release fluid from the anode compartment and/or cathode compartment 54; add fluid (e.g., water, electrolyte, and/or any other suitable material) to the cathode compartment; raise (e.g., via one or more heaters 48) and/or lower a temperature of fluid in the anode compartment, the cathode compartment, the container 40, the dispensing tool 42, and/or any other suitable location; add any other material (e.g., base or acid) to the anode or cathode compartment (e.g., to adjust pH levels); mix the contents of the anode and/or cathode compartments; recirculate fluids through the anode compartment; adjust water softening and/or water treatment operations of the system; adjust a voltage and/or current (e.g., amperage) of the power supply 51 (e.g., flowing between the electrodes 17); operate one or more valves 26 and/or pumps 28 of the system; vary fluid speed through one or more portions of the cell; switch between electrolytes; turn off and/or otherwise alter operating parameters of the cell when water and/or electrolyte levels and/or voltage levels drop too low (and/or otherwise vary from set parameters); and/or for any other suitable purpose. Thus, in some embodiments, the system comprises (as mentioned above) a "closed loop" system that is configured to automatically adjust for different operating conditions (e.g., for operating with waters with different pH levels and/or mineral content), to produce products with different characteristics, and/or for different parameters desired by a particular operator and/or needed for a particular application. In some embodiments, the system is also configured to monitor fluid levels within the various portions of the cell. Thus, in some embodiments, as off gassing occurs, as fluids leave the cell, and/or as fluid levels otherwise drop in the anode compartment 52 and/or the cathode compartment 54, the cell is configured to automatically compensate for such fluid loss (e.g., by adding more electrolyte, electrolyte solution, recirculated anolyte, and/or any other suitable material to one or more compartments of the cell).

In some embodiments, the system's 10 ability to monitor and dynamically adjust operating parameters is constant during cell operation (e.g., taking place in near-real time). That said, in some other embodiments, such monitoring and adjusting takes place in any other suitable manner (including, without limitation, intermittently, during a startup process of the system, randomly, repeatedly, at a set time, as determined by a program, continuously, continually, and/or in any other suitable manner). Additionally, in some embodiments, such monitoring and adjusting takes place at the cell and/or in any other suitable location (e.g., over a network, as described below).

Moreover, some embodiments of the described electrolytic cell 12 (e.g., controller 38) are configured to automatically adjust their operating parameters to produce one or more products (e.g., electrolyzed alkaline water, electrolyzed oxidizing water, bleach, and/or any other suitable product) to have a wide range of characteristics. Indeed, in some cases, the described cells are configured to be able to automatically and selectively use one stream of feed water to produce electrolyzed alkaline waters (and/or electrolyzed oxidizing waters) having pHs that vary by more than about 0.25, 1, 2, 3, 4, 5, 6, or more pH units. In some cases, the described cells are configured to be able to automatically and selectively use one stream of feed water to produce amounts of electrolyzed alkaline water (and/or electrolyzed oxidizing waters) (for instance, by varying electrolyte levels, varying cell operating amperage, varying flowrate within the cell, and/or in any other suitable manner) that have pHs that vary by more than 3 pH units (e.g., by more than 3.5 pH units). In contrast, some competing devices may only be able to take one stream of water and produce final products that vary less than 0.5 pH units from each other.

In accordance with some embodiments, by having the system 10 automatically vary one or more operating parameters of the cell 12, the cell cannot only produce products with desired characteristics, but the cell can further increase its own lifespan. Indeed, while many cells are known to provide a substantially constant level of amperage, despite actual conductivity levels within the electrolytic cells, such cells can greatly over drive cells as electrolyte levels increase and/or decrease within the cell. In contrast, as some embodiments of the described cells are configured to modify amperage levels and/or electrolyte levels, some such embodiments can use 40% to 50% less amperage (or even less) than do some competing devices.

In some cases, when one or more sensors 50, valves 26, pumps 28, and/or other components of the cell 12 fail to function properly, the system is configured to diagnose such a problem, to function without such component, to stop functioning (e.g., to protect the cell, depending on the failure) and/or to otherwise react to such failure. Indeed, in some embodiments, even with a sensor is broken, the cell is configured to operate to the best of its ability without such sensor.

In some embodiments, the system 10 comprises one or more power supplies 51 that are configured to run a current (e.g., a DC current) between the anode 14 and the cathode 16 to produce the electrolyzed alkaline water, oxidizing water, and/or any other suitable chemical (e.g., NaOH, $H_2$, $H_2O_2$, etc. in the cathode compartment 54; $Cl_2$, $O_2$, HOCl, etc. in the anode compartment 52). In this regard, the power supply can comprise any suitable characteristic that allows the system to function as described herein. Indeed, although some embodiments of the power supply are configured to provide a relatively static voltage and/or current to the cell 12, in some other embodiments, the power supply is configured to vary the voltage and/or current that it provides to the cell (e.g., as determined by the control system 38, the operator, and/or otherwise). In this regard, while voltage and/or current levels of some embodiments of the power supply are manually controlled, in some embodiments, the control system 38 is configured to modify the voltage and/or current levels provided by the power supply based on measurements from the sensors 50.

In some embodiments (e.g., as discussed above), the system 10 is configured to measure cell 12 conductivity to determine the electrical power needed by the cell to cause a desired level of ionic breakdown of the water (e.g., in the cathode compartment 54) and the electrolyte (e.g., $Na_2CO_3$ and/or any other suitable electrolyte) in the anode compartment 52. In some other embodiments, however, based on sensor 50 readings, the system (e.g., the control system 38) is configured to calculate cell conductivity (instead of simply measuring it). Thus, in some such embodiments, the system is configured to function without conductivity meters so as to save costs and prevent the maintenance associated with such meters.

In some embodiments, the system 10 (e.g., the control system 38) is configured (e.g., based on calculated and/or measured cell conductivity, NaOH concentrations in the cathode compartment 54, inlet water conditions, anolyte conductivity, catholyte conductivity, and/or any other suitable factor) to continuously adjust power settings of the power supply 51 to perform ionization at the electrodes (e.g., as discussed above), regardless of the flow parameters and/or the concentration of electrolyte in solution (e.g., in the anode compartment 52).

In some embodiments (e.g., as mentioned), the system 10 (e.g., the control system 38) is configured to monitor and control mixtures and amounts of electrolyte (e.g., $Na_2CO_3$ and/or any other suitable electrolyte) being sent to the cell 12 (e.g., to the anode compartment 52 and/or elsewhere). Additionally, in some embodiments, the system manages the valves 26 and pumps 28 to ensure the correct flow of fluids through the cell to maximize electrochemical reactions at the electrodes (e.g., at the anode 14 and/or cathode 16). Moreover, in some embodiments, the system uses calculated and/or measured cell conductivity levels and/or any other suitable information to determine fluid flow levels in the cell and/or to selectively vary (e.g., increase, decrease, and/or stop) fluid flowrate to balance, adjust, and/or optimize fluid flow and/or pressure in the cell.

Turning now to the containers 40, some embodiments of the described system 10 optionally comprise one or more containers to store fluid from the cathode 54 and/or anode 52 compartments. By way of non-limiting illustration, FIG. 1A shows an embodiment in which the system 10 comprises a container 40 that is configured to receive electrolyzed alkaline water from the cathode compartment 54.

In some embodiments, the system 10 comprises one or more heaters 48. While such heaters can perform any suitable function, in some embodiments, they are configured to help: increase the cleaning effectiveness of fluids produced by the system (e.g., the electrolyzed alkaline water), to generate steam, to help chemical reactions in the system 10 to take place at an optimal rate and temperature, and/or for any other suitable purpose. In this regard, the heaters can comprise any suitable heat sources (e.g., heat coils, inductive heaters, boilers, flame heaters, radiators, and/or any other suitable heat sources) and can be disposed in any suitable location, including, without limitation, in the anode compartment 52, the cathode compartment 54, the container 40, the dispensing tool 42, the fluid inlets 20, the fluid outlets 36, and/or in any other suitable location. By way of non-limiting illustration, FIG. 1A shows a representative embodiment of heater 48 placement.

In addition to the aforementioned components, the described system 10 can be modified in any suitable manner. In one example, instead of being permanently installed in place, some embodiments of the described electrolytic cell 12 and/or container 40 are configured to be mobile (e.g., being disposed on one or more carts, dollies, hand trucks, trucks, vans, vehicles, backpacks, pallets, trailers, and/or other suitable items). By way of non-limiting illustration, FIGS. 1L-1O show some embodiments in which the system 10 is configured to fit within a vehicle 99. Specifically, FIGS. 1L-1O show some embodiments in which a vehicle 99 comprises the electrolytic cell 12, the power supply 51, a container 40 and/or 46, a water softener 24, and/or any other suitable portion of the system 10.

Figure 1E:
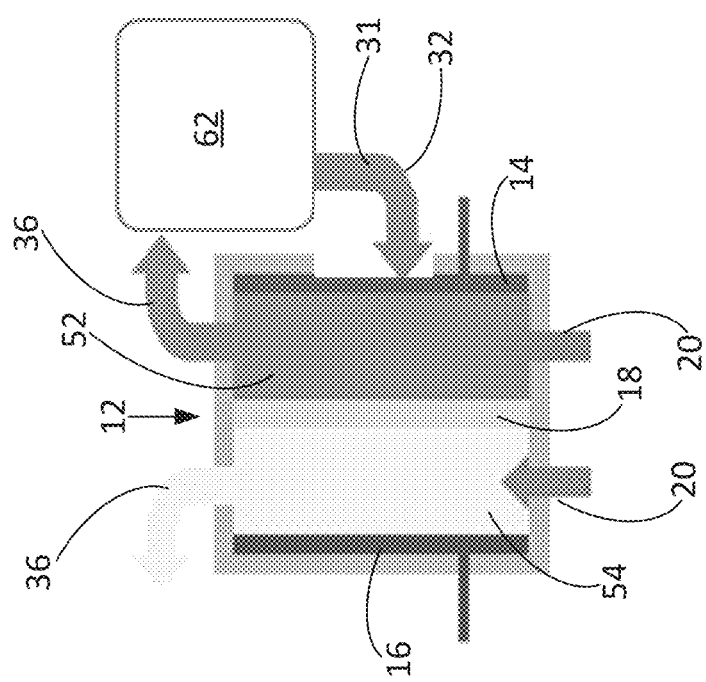
FIG. 1E illustrates a schematic view of an electrolytic cell that is configured to recirculate an anolyte through its anolyte compartment in accordance with a representative embodiment.
Figure 1F:
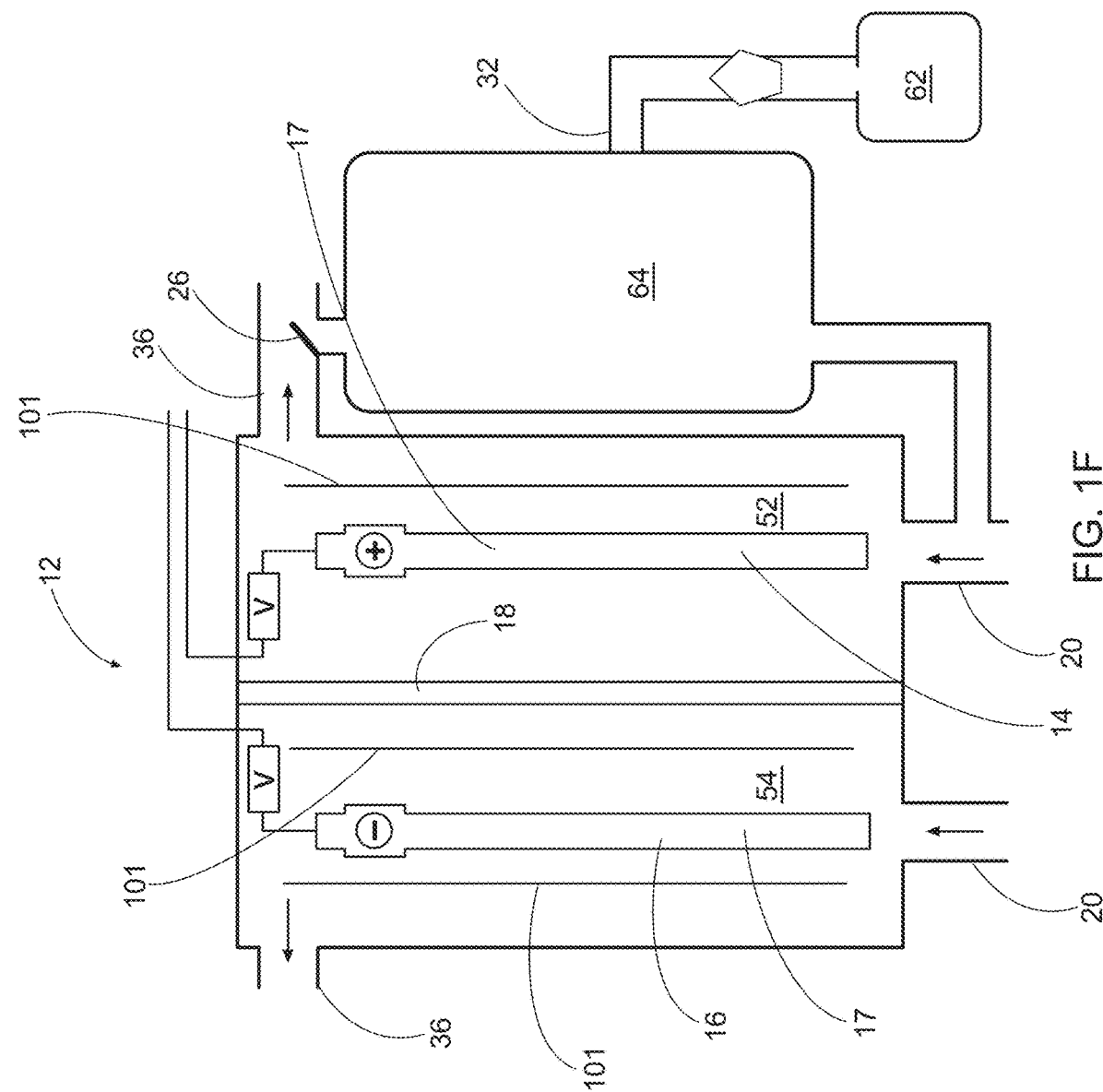
FIG. 1F illustrates a schematic view of the electrolytic cell, wherein the electrolytic cell is configured to recirculate anolyte through its anolyte compartment in accordance with a representative embodiment.

In another example of a suitable modification, FIGS. 1D and 1E show different embodiments in which the cell 12 comprise a recirculation loop 31. Additionally, those drawings show that, in some embodiments, although the anode 14 and/or cathode 16 can be disposed in any suitable locations, in some embodiments, such electrodes are disposed near a wall of the cell 12. Additionally, FIG. 1F shows that, in some embodiments, the anode 14 and/or cathode 16 are configured to extend substantially along a full length of the cell 12 so as to allow fluids in the various compartments (e.g., the anolyte and catholyte) to have an increased opportunity to contact the various electrodes and to react. Moreover, FIG. 1F shows that, in some embodiments, the anode 14 and/or cathode 16 are placed directly in the flow path of fluids into the various compartments through the inlets. Again, while such placement can perform any suitable function, in some cases, such placement allows fluids to have a higher likelihood of contacting the electrodes and reacting. Additionally, in some cases, by having the electrodes in the fluid flow paths, the flow of fluid across the electrodes can help to remove gas bubbles (which can cause inefficiencies) from the electrodes.

Figure 1I:
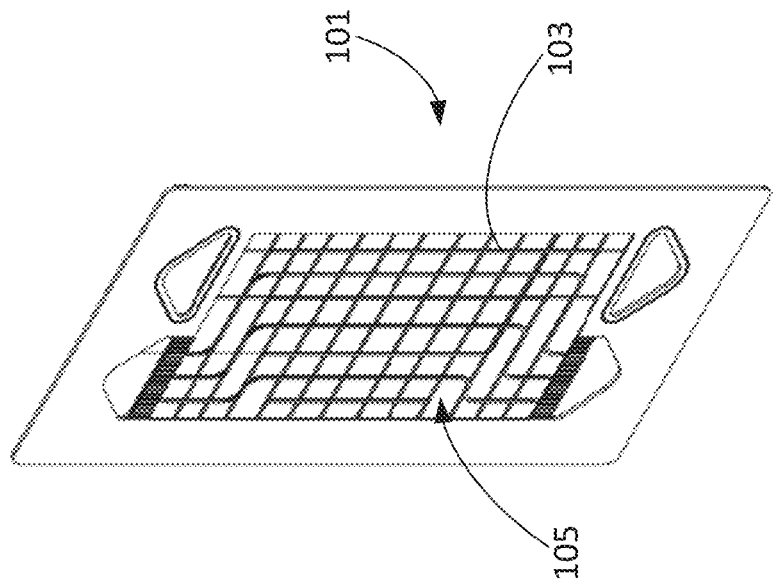
FIG. 1I illustrates a perspective view of a spacer frame that is used in connection with the described electrolytic cell in accordance with some representative embodiments.
Figure 1H:
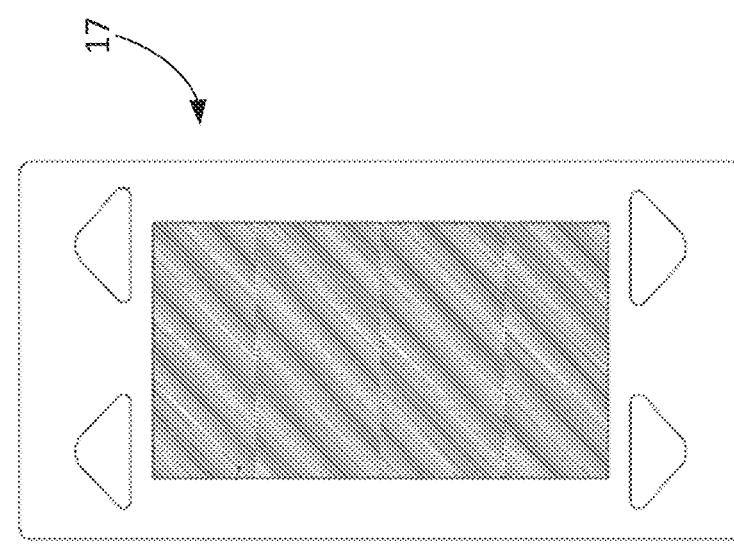
FIG. 1H illustrates a view of an electrode that is used in connection with the described electrolytic cell in accordance with some representative embodiments.
Figure 1K:
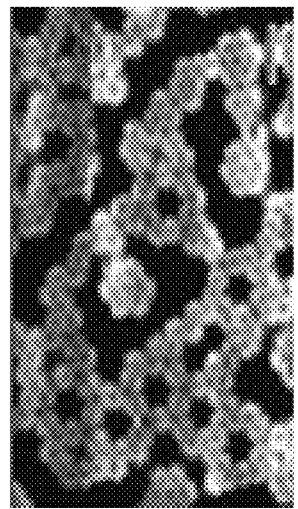
FIG. 1K illustrates an electron microscope image depicting hexamer water clusters formed by exposure to an electrode in accordance with some embodiments.
Figure 1J:
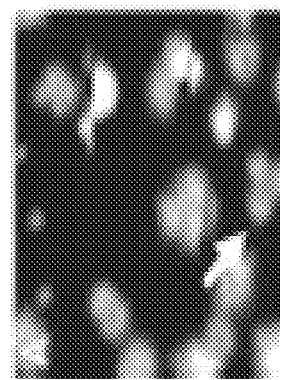
FIG. 1J illustrates an electron microscope image depicting water clusters found in regular water.
Figure 1L:
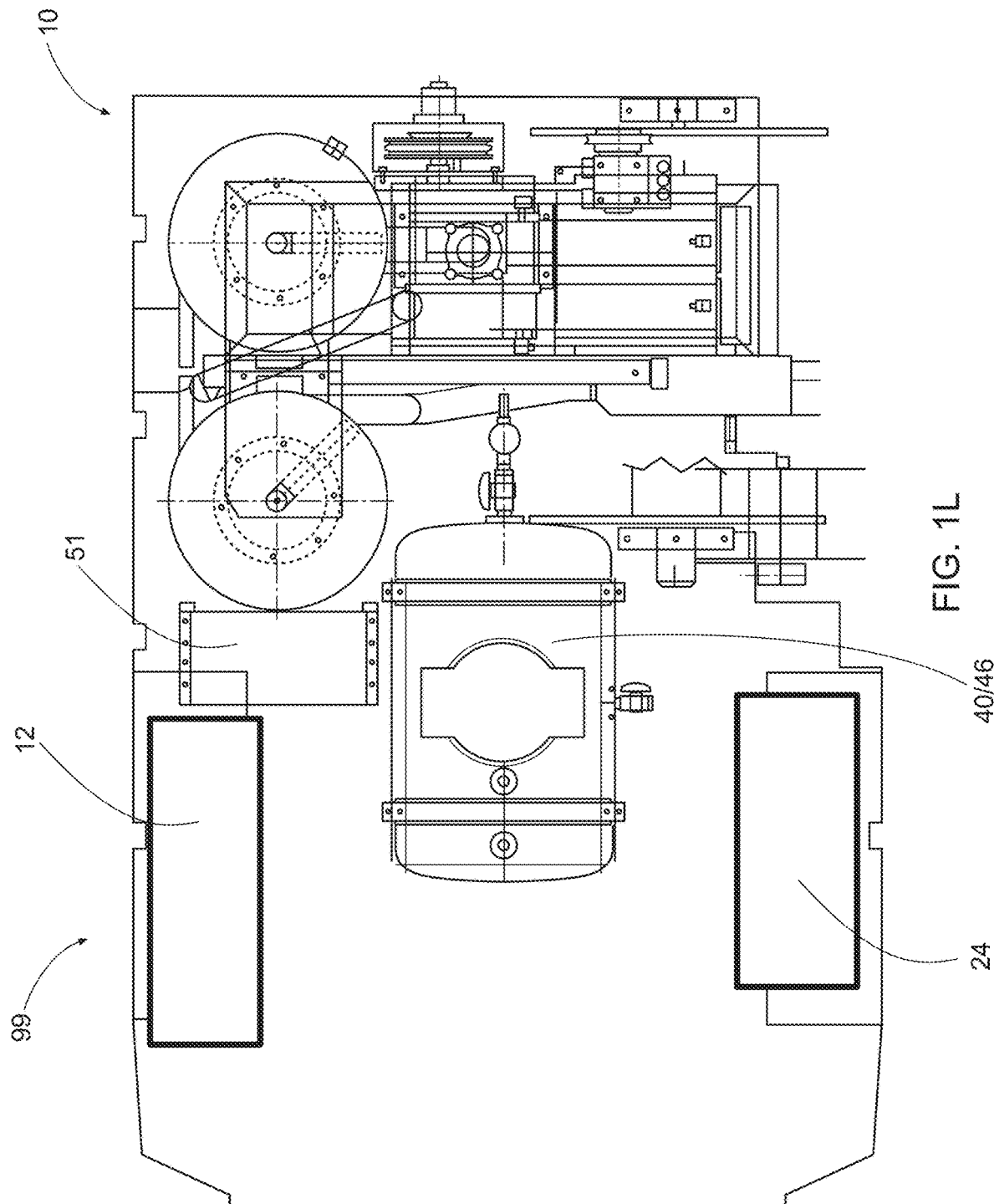
FIG. 1L illustrates a schematic diagram showing some embodiments of the described systems that are carried in a vehicle.
Figure 1N:
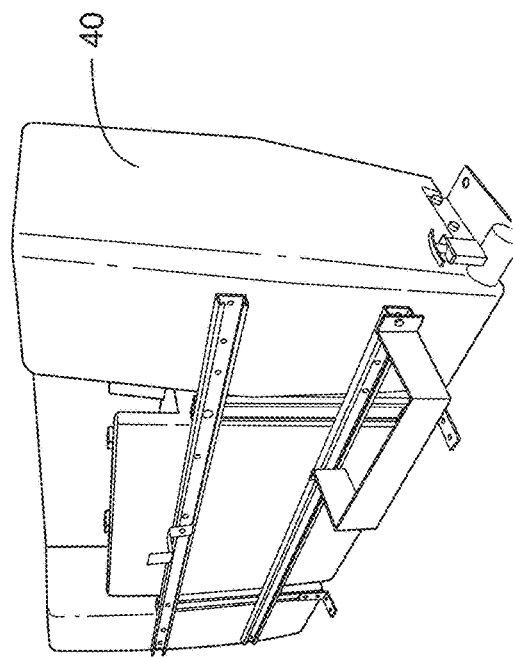
FIGS. 1M-1O depict different portions of the described system, disposed within a vehicle in accordance with some representative embodiments.
Figure 1M:
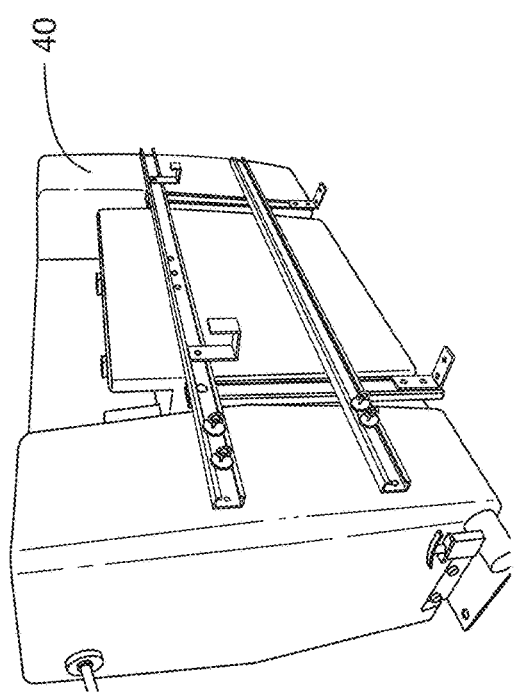
Figure 1O:
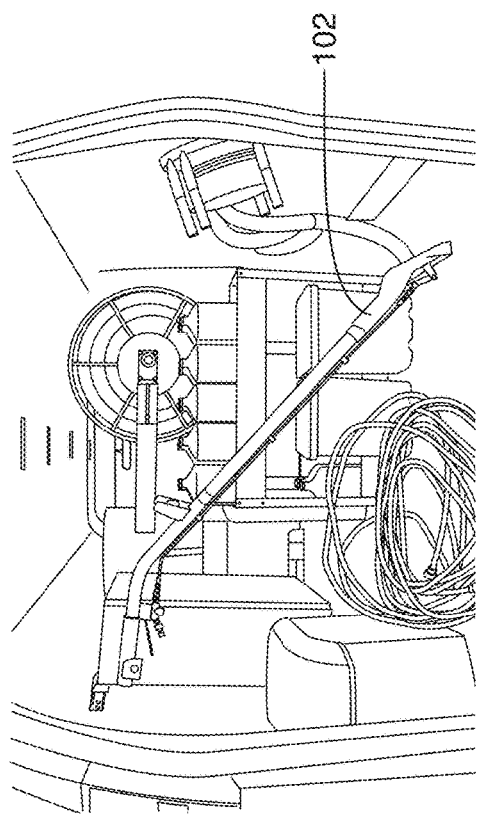

As another example of a suitable modification, FIGS. 1F, 1G, and 1I show that, in some embodiments, the cell 12 comprises one or more spacer frames 101. In this regard, the spacer frames can perform any suitable function that allows the cell to function as intended. Indeed, in some embodiments, FIG. 1G shows that a spacer frame (e.g., the spacer frame 101 in the middle of the cell 12 is configured to help direct influent (e.g., an electrolyte solution) into both the anode compartment 52 and the cathode compartment 54. Additionally, FIGS. 1F and 1G show that, in some embodiments, one or more spacers 101 are in close proximity to one or both of the electrodes 17. In particular, FIGS. 1F and 1G show some embodiments in which each electrode is sandwiched between two spacer frames 101.

Where the cell 12 comprises one or more spacer frames 101, the spacers can be disposed any suitable distance from the electrodes 17. Indeed, in some embodiments, each electrode is sandwiched between two spacer frames, with such frames contacting a side of the corresponding electrode.

While the spacer frames 101 can have any suitable component and/or characteristic, FIG. 1I shows that, in some embodiments, the spacers 101 comprise a plate (and/or any other suitable object that is configured to have a substantial portion of one surface to be held in close proximity to a corresponding surface of a corresponding electrode 17). In this regard, some embodiments of the spacers comprise one or more holes that extend through the spacers (e.g., to allow electrons and ions to readily move through the spacers). In some embodiments, the spacers also comprise one or topographical features that are configured to channel, mix, churn, agitate, blend, stir, and/or otherwise direct fluid past a corresponding electrode. By way of non-limiting illustration, FIG. 1I shows that in some embodiments, the spacers 101 comprise one or more channels, raised surfaces 103, recesses, protrusions, and/or other suitable topographical features that are configured to help ensure that more of the fluid in the cell is run past and is reacted by at least one of the electrodes. Indeed, in some embodiments, when a spacer is in close proximity to a corresponding electrode and fluid flows between the two, the topographical features of the spacer force the fluid to mix, thereby ensuring more (if not complete) exposure of the fluid to the electrode and its electrical fields.

In accordance with some embodiments, one or more surfaces of one or more of the electrodes 17 is matched in size and/or shape (e.g., precisely or otherwise) with a corresponding spacer 101. In some such embodiments, one or more flow paths, channels, openings, and/or other features of each spacer (e.g., as shown in FIGS. 1H and 1I) are aligned with the corresponding surface of the corresponding electrode to ensure substantial (if not complete) contact with the electrolyte solution (i.e., its various ionic materials) and the charged electrode surface (e.g., to optimize ionization). In some such elements, a distance between (and/or contact with) the spacers and electrodes is maintained throughout cell operation.

As another example of a suitable modification, FIG. 1G shows that, in some embodiments, the cell 12 comprises a single inlet 20 and a single outlet 36 (though more could be used). Additionally, that drawing shows that, in some embodiments, instead of having an ion selective membrane (e.g., membrane 18) be disposed between the anode compartment 52 and the cathode compartment 54, in some embodiments, a spacer 101 is at least partially disposed between the two compartments. In this regard, such a cell can perform any suitable function including, without limitation, producing bleach (NaClO), HOCl, ClO$^-$, and/or any other suitable product. Indeed, in some embodiments, such cell is capable of forming a concentrated bleach, with bleach molecules found in the product at a concentration of between 400 and about 8,000 parts per million (ppm). In this regard, while some competing devices that are configured differently are capable of forming bleach at 20-300 ppm, some embodiments of the described cell are capable of producing bleach at a concentration greater than 1,000 ppm (e.g., about 7,500 ppm±1,000 ppm). In this regard, it should be noted that the cells 12 of FIGS. 1D-1G and 1L can comprise any of the components and/or features of the other cells described herein (e.g., comprising any suitable valve 26, feeder 34, pump 28, control system 38, and/or other component described herein); being able to monitor operational parameters; being able to modify amperage, electrolyte concentration, pH, flowrate, and/or any other suitable operating parameter (or condition) of the cell in near real time; being able to use any suitable electrolyte and/or combination of electrolytes (e.g., NaCl, a non-NaCl electrolyte (such as soda ash), and/or any other suitable electrolyte); being able to recirculate anolyte through the anode compartment 52 (and/or the cell), and/or any other feature described herein).

As another example of a suitable modification, instead of being used to clean carpets and/or other flooring, some embodiments of the system are configured to be used with one or more clothes washing machines, dish washers, street sweepers, high pressure washers, floor cleaners, parking lot cleaners, disaster cleanup devices, and/or any other suitable devices. Indeed, in some embodiments, in place of (or in addition to) adding soap to a clothes washing machine, a dish washer, and/or any other suitable device, some embodiments of the described system are configured to provide such a device with electrolyzed alkaline and/or oxidizing water for use as a cleaning and/or disinfecting agent.

The described system 10 can be used in any suitable manner and for any suitable purpose. Indeed, in some embodiments, a user (and/or the system) adds an electrolyte solution to the anode compartment 52 and water (and/or any other suitable chemical, including without limitation, and/or any other suitable chemical) to the cathode compartment 54. In some such embodiments, the user (and/or the system) then runs the electrolytic cell 12 to generate electrolyzed alkaline water in the cathode compartment. In some cases, as electrolyzed oxidizing water is produced in the anode compartment 52, such fluid is recirculated through the anode compartment, with additional electrolyte and/or water being added to the anode compartment as necessary (e.g., by the control system 38, the electrolyte feeder 34, an operator, and/or in any other suitable manner). Thus, while some embodiments of the system produce relatively large amounts of electrolyzed alkaline water (e.g., for use as a cleaning agent), in some cases, the system produces and/or releases relatively little (or no) electrolyzed oxidizing water. In some embodiments, however, the system is easily modified (e.g., by automatically and/or manually opening and/or closing one or more valves 26, actuating one or more pumps 28, and/or otherwise) to allow an operator (and/or the system) to selectively release (and/or produce a larger quantity of) the electrolyzed oxidizing water (e.g., to be used to sanitize a surface and/or for any other suitable purpose). In this regard, it should be noted that where the system automatically monitors and updates its operating parameters, the system can function far more efficiently and with much less input from an operator that would be required in some embodiments in which control of the various operating parameters of the cell are required to be manually changed.

Additionally, although some embodiments of the system are configured to use a first electrolyte (e.g., $Na_2CO_3$ and/or any other suitable electrolyte), in some other embodiments, the system is configured to be switched to use a second electrolyte (e.g., NaCl and/or any other suitable electrolyte) at any suitable time (e.g., on demand). In this regard, while some embodiments of the system are configured to operate with only the first or the second electrolyte, in some embodiments, the system is configured to selectively use two or more electrolytes (or combinations thereof).

As mentioned, fluids from the system 10 can be used in any suitable manner. Indeed, in some embodiments, fluids from the cathode compartment 54 (e.g., alkaline water) and/or the anode compartment 52 (e.g., oxidizing water) are discharged into one or more containers 40 (e.g., a container on a truck, van, backpack, a base of operations, and/or any other suitable location), a drain, a dispensing tool 42, and/or any other suitable location. In some embodiments, however, the electrolyzed alkaline water (and/or, in some embodiments, the electrolyzed oxidizing water) are passed through one or more dispensing tools 42 (e.g., to clean a surface and/or material), and a vacuum 44 is then used to suck up the used fluid with any debris, with the recovered fluid and debris being sent to a holding tank 46, a drain, and/or any other suitable location.

Additionally, (as previously mentioned) while some embodiments of the system 10 are configured to recycle electrolyzed oxidizing water (and to thereby release little to no oxidizing water from the system), in some other embodiments, the system can be switched to produce and/or release electrolyzed oxidizing water for any suitable purpose (e.g., sanitizing stains left by pets). In one non-limiting example, FIGS. 1L-1O show some embodiments in which the system 10 is disposed in a vehicle 99. In some such embodiments, the system is configured to recirculate anolyte through the anode compartment 52, without releasing anolyte. As a result, such a system requires relatively less water, requires relatively less electrolyte, produces relatively less waste, and requires relatively less space than some competing systems. Accordingly, some embodiments of the current system are relatively inexpensive to operate and transport. Some embodiments of the described system 10 are configured to include or provide some beneficial features. Indeed, in some embodiments, electrolyzed oxidizing water is recycled through the anode compartment 52. As a result, some such embodiments may use (and/or waste) substantially less water than do some conventional electrolytic devices. For instance, some conventional devices create as much oxidizing water as alkaline water. Indeed, in some conventional devices it is not possible (or at least not easy) to produce more alkaline water than oxidizing water. In this regard, as the oxidizing water is typically not considered (at least by some) to be as useful or needed (e.g., in cleaning carpets and other flooring or objects) as alkaline water, the oxidizing water is often times wasted and simply poured down a drain, where it can cause environmental issues. Accordingly, in some cases, almost half of the fluid produced by some conventional devices is typically wasted. In contrast, as some embodiments of the described system produce and release relatively little (or no) oxidizing water (e.g., unless otherwise desired), the described system can be environmentally friendly, be relatively inexpensive to operate, be relatively convenient to use, and can produce relatively small amounts of corrosive, smelly, acidic water that is discharged.

As yet another example, some embodiments of the membrane 18 are relatively non-porous. Indeed, unlike some conventional electrolytic devices that comprise a relatively porous membrane, which allows mixing of the acidic fluids from the anode compartment 52 with alkaline fluids of the cathode compartment 54, some embodiments of the described system comprise one or more non-porous membranes that allow alkali ions (e.g., $Na^+$) and protons (e.g., $H^+$) to pass through the membrane while separating the electrolyzed oxidizing water in the anode compartment from the alkaline water in the cathode compartment. Accordingly, in some embodiments, the electrolyzed alkaline water produced in the system's cathode compartment is relatively pure, and free from acids, salts, and/or other contaminants that are able to pass through the porous membrane of some conventional devices.

In still another example, as some embodiments of the described system 10 recycle fluid (e.g., electrolyzed oxidizing water and electrolyte solution) through the anode compartment 52, alkali ions (e.g., $Na^+$) (which in some conventional devices is discarded or are otherwise passed through an anode compartment one time) are recirculated and given additional opportunities to pass through the membrane 18 into the cathode compartment 54.

In some embodiments, by recirculating fluids through the anode compartment 52 (and/or the anolyte recirculation tank 64) and thus allowing a greater portion of alkali ions (e.g., $Na^+$) in the anode compartment to pass through the membrane 18 and into the cathode compartment 54 than occurs in some conventional devices, and as some embodiments reduce and/or completely prevent mixing between the acid solutions of the anode compartment and the basic solutions of the cathode compartment, some embodiments of the described system 10 are configured to produce higher and purer concentrations of NaOH in the cathode compartment than do some conventional devices. Indeed, while some conventional devices may produce less than about 100 ppm or even 50 ppm or less of NaOH (e.g., in the electrolyzed alkaline water), some embodiments of the described system produce electrolyzed alkaline water having an NaOH concentration of between 100 ppm and about 700 ppm (or any subrange thereof). Indeed, some embodiments of the system are configured to produce electrolyzed alkaline water having a NaOH concentration of above about 200 ppm (e.g., above about 250 ppm).

As another example, some embodiments of the system 10 are easily reconfigured (e.g., by flipping a switch, opening and/or closing one or more valves 26, by actuating one or more pumps 28, by selecting a different operation mode for the system, and/or in any other suitable manner) to selectively switch from releasing electrolyzed alkaline water (e.g., for delivery through a dispensing tool 42 or otherwise) to releasing electrolyzed oxidizing water on demand (and/or combinations thereof) (e.g., for use as a sanitizer and/or for any other suitable purpose). In some such embodiments, the system is also easily selectively changed back to releasing alkaline water on demand. Thus, in some embodiments, the system (on demand) can pass more fluids through the anode compartment and/or produce more electrolyzed oxidizing water upon demand. Additionally, in some embodiments, instead of just being able to switch between releasing a larger amount of alkaline water than oxidizing water (or vice versa), some embodiments of the system are configured to release alkaline water and oxidizing water simultaneously (e.g., via two different dispensing tools 42, to two different tanks, and/or in any other suitable manner).

In even another example, some embodiments of the described system 10 are configured to be mostly, if not completely, automated (e.g., as discussed above). Accordingly, such embodiments can be relatively easy to use and can automatically adjust for different situations (e.g., feed water compositions, uses, etc.). Indeed, some such embodiments can automatically compensate (e.g., adjust operating parameters) for the characteristics (e.g., pH and/or any other suitable characteristic) of water from a variety of sources. Similarly, some embodiments of the system are configured to automatically adjust operating parameters to produce electrolyzed alkaline water with one or more desired concentrations of NaOH.

In still another example, some embodiments of the described system can be relatively small (e.g., as discussed above). In some other embodiments, however, the system is easily scaled up in size to produce higher volumes of electrolyzed alkaline water, with higher concentrations of NaOH.

In still another example, some embodiments of the system 10 comprise a stainless steel, open frame design that provides for superior maintenance access over some conventional devices.

In even another example, as some embodiments of the described system 10 place water in the cathode compartment 54 (instead of an electrolyte solution), and as some embodiments of the system comprise a relatively non-porous membrane 18, some embodiments of the described system produce electrolyzed alkaline water that is substantially if not completely free from NaCl (and/or other electrolytes). This is especially true in some embodiments in which the anolyte comprises a non-sodium chloride electrolyte (e.g., soda ash), as discussed hereinafter. In contrast, in some conventional devices, a NaCl solution is added to both the anode and cathode compartment, with most of the salt passing straight through the cell, with only a small fraction of the salt ultimately producing NaOH in the catholyte. Indeed, in some conventional devices, unreacted chlorides account for 1,500 ppm or even 2,000 ppm in the produced oxidizing water and often even higher concentrations in the electrolyzed alkaline water. This excess chloride and NaCl often has no cleaning effect, but instead tends to leave NaCl in the cleaned materials.

Thus, some embodiments of the present invention relate to systems and methods for producing electrolyzed alkaline water and/or electrolyzed oxidizing water by electrolyzing a solution comprising one or more electrolytes. While the electrolyzed alkaline water and/or electrolyzed oxidizing water can be used for any suitable purpose, in some embodiments, they are used to clean and/or disinfect carpets, rugs, tile, stone, linoleum, flooring surfaces, furniture, walls, drywall, plaster, countertops, blinds, appliances, woods, metals, vehicles, upholstery, drapes, fabrics, clothing, cloth, bedding, textiles, and/or any other suitable surface, object, or material. Additionally, in some embodiments, the described system is configured to produce different ratios of electrolyzed alkaline and oxidizing water. Moreover, in some embodiments, the described system is configured to selectively switch between using a first electrolyte (e.g., sodium carbonate) and a second electrolyte (e.g., sodium chloride), and vice versa, on demand.

Electrolytes

The described system 10 can be used with any suitable electrolyte that allows the system to produce electrolyzed alkaline water, electrolyzed oxidizing water, and/or any other suitable product. Moreover, in place of, or in addition to, being used with the described system, the electrolytes described herein can be used with any other suitable electrolytic device. In this regard, some embodiments of the described system (and/or any other suitable device) are configured to use sodium chloride (NaCl) as the electrolyte. In some other embodiments, however, the electrolyte comprises a non-sodium chloride or at least a non-sodium chloride based electrolyte. In this regard, where the electrolyte comprises a non-sodium chloride electrolyte, the electrolyte can comprise any suitable alkali salt that is capable of allowing the described systems 10 to produce electrolyzed water and/or any other suitable chemical, and that do not comprise or that comprise a relatively small amount of sodium chloride (again, if any). Some non-limiting examples of suitable non-sodium chloride electrolytes include, but are not limited to, sodium carbonate ($Na_2CO_3$), soda ash, sodium bicarbonate ($NaHCO_3$), potash, potassium carbonate ($K_2CO_3$), potassium bicarbonate ($KHCO_3$), sodium chloride, potassium nitrate ($KNO_3$), potassium chloride (KCl), potassium chlorate ($KClO_3$), sodium phosphate, and/or any other suitable electrolyte (e.g., any suitable alkali ion containing electrolyte). In some embodiments, however, the electrolyte comprises $Na_2CO_3$ and/or sodium $NaHCO_3$.

In some cases, the electrolyte (e.g., $Na_2CO_3$) is added to water (e.g., in the anode compartment 52, where anolyte is recirculated through the cell 12, and/or to the cathode compartment, where applicable) at any suitable concentration that allows the resultant electrolyte solution to be electrolyzed to form electrolyzed oxidizing water and/or electrolyzed alkaline water (and/or any other suitable chemical). In some embodiments, the electrolyte (e.g., $Na_2CO_3$) is added to water (e.g., that is in and/or that is to be added to) the anode compartment 52 at a concentration of between about 0.1% and about 60% by weight (or within any subrange thereof). Indeed, in some embodiments, the electrolyte (e.g., $Na_2CO_3$) is added to water at a concentration of between about 10% and about 30% by weight (e.g., at a concentration of about 20%±5%). Additionally (as described above), in some embodiments, as the system 10 operates, additional electrolyte is added (e.g., automatically and/or manually, as discussed above) to the anode compartment and/or the cathode compartment 54 (e.g., via the electrolyte feeder 34, the control system 38, and/or otherwise) to keep the electrolyte at a desired concentration (e.g., in the anode compartment). Indeed, in some embodiments, a $Na_2CO_3$ solution is added to the anode compartment and/or additional electrolyte is added to the anode compartment as needed (e.g., as controlled by the control system 38 or otherwise), while water is added to the cathode compartment 54. Again, and as discussed, in some embodiments, the system is configured to vary the amount of electrolyte that is added to the anode compartment to adjust for varying levels of amperage and/or changes in conductivity of electrolyte within the cell.

Where the electrolyte comprises $Na_2CO_3$ (sodium carbonate) and/or $NaHCO_3$ (sodium bicarbonate) a variety of chemical reactions may occur as the electrolytic cell 12 is operated. In some cases, however (as shown below), electrolysis of $Na_2CO_3$ and $NaHCO_3$ in the cell 12 produces NaOH (e.g., in the electrolyzed alkaline water in the cathode compartment 54), carbon dioxide ($CO_2$) (e.g., in the anode compartment 52), hydrogen gas ($H_2$) (e.g., in the cathode compartment), hydrogen peroxide ($H_2O_2$) (e.g., in the cathode compartment), oxygen ($O_2$) (e.g., in the anode compartment), hypochlorous acid (HOCl) (e.g., in the electrolyzed oxidizing water in the anode compartment), and/or a variety of other possible chemicals. Indeed, in some embodiments, electrolysis of solutions comprising $Na_2CO_3$ or $NaHCO_3$ have results in the following:

$$Na_2CO_3(aq)+2H_2O(l) \rightarrow 2NaOH(aq)+CO_2(g)+1/2O_2(g)+H_2(g)$$

$$2NaHCO_3(aq)+2H_2O(l) \rightarrow 2NaOH(aq)+2CO_2(g)+O_2(g)+2H_2(g)$$

Thus, in some embodiments, the electrolysis of $Na_2CO_3$ (sodium carbonate), $NaHCO_3$ (sodium bicarbonate), and/or another suitable electrolyte does not produce chlorine gas ($Cl_2$) (or at least relatively little amounts), as is (or can be produced) when NaCl is electrolyzed in the system 10 and/or in some conventional devices. Accordingly, in some embodiments, the use of such electrolytes is relatively safe (e.g., by not exposing users to toxic chlorine gas and/or noxious chlorine chemicals) and does not expose surrounding structures (e.g., vehicles) the highly corrosive effects of chlorine gas. Additionally, in some embodiments in which the electrolyte solution is added to the anode compartment 52 while water is added to the cathode compartment, the described system can produce electrolyzed alkaline water that is substantially free from salts (e.g., NaCl). Thus, unlike some conventional devices that produce electrolyzed alkaline water with a relatively high salt content (which can leave salt in carpets and other materials that are cleaned with the alkaline water), some embodiments of the described system are able to produce a relatively pure aqueous NaOH solution (which leaves no salt or other residue on cleaned objects). Furthermore, as some embodiments of the electrolyzed alkaline water are relatively (if not completely) salt (e.g., NaCl) free, such liquids can be substantially less corrosive (e.g., to sewers, containers 40, equipment, etc.) than are some conventional electrolyzed alkaline waters that comprise NaCl.

Once $Na_2CO_3$ (sodium carbonate), $NaHCO_3$ (sodium bicarbonate), and/or another suitable non-NaCl electrolyte is used to create electrolyzed alkaline water, electrolyzed oxidizing water, and/or any other suitable product (e.g., via the system 10 and/or any other suitable device), the various chemicals produced by such an electrolysis process can be used for any suitable purpose and in any suitable manner, including, without limitation, for cleaning and/or sanitizing. Indeed, in some embodiments, the electrolyzed alkaline water is used to clean flooring (e.g., carpets, rugs, tile, stone, and other flooring surfaces), furniture, walls, countertops, vehicles, upholstery, and/or any other suitable surface or material, and the electrolyzed alkaline water (if released from the system at all) can be used to sanitize objects.

Where $Na_2CO_3$ (sodium carbonate), $NaHCO_3$ (sodium bicarbonate), and/or another suitable non-NaCl electrolyte is used to create electrolyzed alkaline water and/or electrolyzed oxidizing water, the various fluids produced can have any suitable characteristic. Indeed, in some embodiments, the pH range, NaOH concentration, oxidation reduction potential or ORP, and/or other characteristic of the fluids produced with the described electrolyte(s) can be modified (e.g., automatically, as discussed above; manually, as discussed herein, and/or in any other suitable manner) to meet any desired and possible range. For instance, more or less water and/or electrolyte can be added to the anode 52 and/or cathode 54 compartments, flowrates can be increased and/or decreased, and/or more or less voltage and/or current can be added to the cell 12 (e.g., as controlled manually, in order to hit user selected levels, as controlled by the control system 38 and/or sensors 50, and/or otherwise).

In any case, the electrolyzed alkaline water produced with $Na_2CO_3$ (sodium carbonate), $NaHCO_3$ (sodium bicarbonate), and/or another suitable non-NaCl electrolyte can have any suitable pH, including, without limitation, a pH between about 10.5 and about 14.5 (or any subrange thereof). Indeed, in some embodiments, the alkaline water comprises a pH between about 11 and about 12.5 (e.g., between about 11.5 and about 12.2). Again, when in accordance with some embodiments, the described system 10 can take a single source of feed water and use that feed water (e.g., by automatically adjusting one or more operating conditions of the cell) to produce multiple amounts of alkaline water having different pHs (as indicated by the user, a program, and/or in any other suitable manner).

The electrolyzed alkaline water produced with $Na_2CO_3$ (sodium carbonate), $NaHCO_3$ (sodium bicarbonate), and/or another suitable non-NaCl electrolyte can have any suitable NaOH concentration, including, without limitation, a NaOH concentration between about 50 and about 700 ppm (or within any subrange thereof). Indeed, in some embodiments, electrolyzed alkaline water that is produced through the use of the described electrolytes (e.g., non-NaCl electrolytes) has a NaOH concentration between about 75 and about 550 ppm (e.g., between about 115 and 510). In some cases, however, the NaOH concentration of the alkaline water produced by the described system 10 is between about 125 and about 500 ppm.

The electrolyzed alkaline water produced with $Na_2CO_3$ (sodium carbonate), $NaHCO_3$ (sodium bicarbonate), and/or another suitable non-NaCl electrolyte can have any suitable oxidation reduction potential (or ORP), including, without limitation, an ORP between about −200 mv and about −1,100 mv (or any subrange thereof). Indeed, in some embodiments, electrolyzed alkaline water that is produced through the use of the described electrolytes (e.g., non-NaCl electrolytes) has an ORP between about −300 mv and about −1,000 mv (e.g., between about −400 mv and −900 mv).

The electrolyzed alkaline water produced with $Na_2CO_3$ (sodium carbonate), $NaHCO_3$ (sodium bicarbonate), and/or another suitable non-NaCl electrolyte can have any suitable chloride or chlorine concentration. In some non-limiting embodiments, however, such alkaline water has a chloride or chlorine concentration of essentially 0.

The electrolyzed oxidizing water produced with $Na_2CO_3$ (sodium carbonate), $NaHCO_3$ (sodium bicarbonate), and/or another suitable non-NaCl electrolyte can have any suitable pH, including, without limitation, a pH between about 1 and about 6.5 (or any subrange thereof). Indeed, in some embodiments, the oxidizing water comprises a pH between about 2.5 and about 4.5 (e.g., between about 3 and about 4). Again, in some embodiments, the system 10 is configured to automatically adjust its operating to produce oxidizing water with different pHs to meet a user's desires.

The electrolyzed oxidizing water produced with $Na_2CO_3$ (sodium carbonate), $NaHCO_3$ (sodium bicarbonate), and/or another suitable non-NaCl electrolyte can have any suitable HOCl concentration, including, without limitation, a HOCl concentration between about 1 and about 10,000,000 ppm (or any subrange thereof). Indeed, in some embodiments, electrolyzed oxidizing water that is produced through the use of the described electrolytes (e.g., non-NaCl electrolytes) has a NaOH concentration between about 100 and about 700 ppm (e.g., between about 200 and 500). In some cases, however, the HOCl concentration of the oxidizing water is between about 250 and about 450 ppm.

The electrolyzed oxidizing water produced with $Na_2CO_3$ (sodium carbonate), $NaHCO_3$ (sodium bicarbonate), and/or another suitable non-NaCl electrolyte can have any suitable oxidation reduction potential (or ORP), including, without limitation, an ORP between about 100 mv and about 2,000 mv (or any subrange thereof). Indeed, in some embodiments, electrolyzed oxidizing water that is produced through the use of the described electrolytes (e.g., non-NaCl electrolytes) has an ORP between about 800 mv and about 1,600 mv (e.g., between about 1,000 mv and 1,400 mv).

Some embodiments of the described system 10 are configured to include or provide some beneficial features (including, without limitation, one or more of the beneficial features discussed above with respect to the system 10). Indeed, in some embodiments, by using $Na_2CO_3$ (sodium carbonate), $NaHCO_3$ (sodium bicarbonate), and/or another suitable non-NaCl electrolyte in an electrolysis process, the electrolyzed alkaline water produced therefrom can be substantially (if not completely) free from NaCl, chloride ions, and/or chlorine. Accordingly, such alkaline water can be relatively pure so as not leave NaCl behind in cleaned materials. Additionally, in some cases in which the alkaline water lacks NaCl, the alkaline water can be relatively non-corrosive, and hence, can be relatively safe for discharge into drains (e.g., after it has been used to clean an object or material).

Thus, some embodiments of the described systems and methods relate to the production of electrolyzed alkaline water and/or electrolyzed oxidizing water by electrolyzing a solution comprising sodium carbonate, soda ash, sodium bicarbonate, washing soda, soda crystals, crystal carbonate, sodium acetate, sodium percarbonate, potassium carbonate, potassium bicarbonate, sodium phosphate, and/or any other suitable non-NaCl electrolyte.

Wand

In accordance with some embodiments, the described systems and methods include a wand that is configured to spray (and/or otherwise deliver) one or more fluids (e.g., water, electrolyzed alkaline water, electrolyzed oxidizing water, stabilized alkaline water, stabilized acidic water, reverse osmosis water, deionized water, cleaning agents, detergents, soaps, air, waxes, stain guards, dyes, pre-treatments, post-treatments, pre-sprays, and/or any other suitable fluid) onto an object and to then have such fluid and/or debris be sucked from such object, through the wand, and into a depository (e.g., a tank, container, a drain, and/or any other suitable location).

While the described wand can comprise any suitable component or characteristic that allows it to function as intended, FIGS. 2A-2G illustrate some embodiments in which the wand 100 comprises one or more vacuum tubes 102, wand heads 104, shrouds 106, jets 108, jet manifolds 109, vacuum ports 110, breaker bars 112, rollers 114, lips 116, feed lines 118, trigger assemblies 120, filters 122, handles 124, and/or handle supports 125.

With respect to the vacuum tube 102, the tube can comprise any suitable characteristic that allows it to be used to push, pull, and/or otherwise direct movement of the wand head 104 and to conduct fluids, debris, and/or other material from the wand head to a depository. In some embodiments, the vacuum tube has a relatively large inner diameter, which allows an increased amount of air, oxygen, water, fluid, debris, and/or other materials to pass through the tube. Indeed, in some embodiments, because of its relatively large inner diameter, the tube is able to allow a standard vacuum to pass more air across (and pull more fluid from) the flooring, walls, drapes, (and/or other object) being cleaned than could the same vacuum with a smaller vacuum tube. As a result, some embodiments of the described vacuum tube allow the flooring (and/or other material) to dry faster than would smaller vacuum tubes. Moreover, because of its relatively large inner diameter, some embodiments of the described vacuum tube are able to perform a better job at removing dirt, hair, flooring fragments, oils, sand, particulates, stains, and/or other debris from flooring and/or other surfaces that are cleaned with the described vacuum tube. Additionally, in some embodiments, while the inner diameter of the vacuum is relative large, the outer diameter of the vacuum tube is still small enough that it can easily fit in the hand of a user so as to allow the user to hold the tube without undue hand fatigue.

While the vacuum tube 102 can have any suitable inner diameter (e.g., between about 5 mm and about 25 cm, or within any subrange thereof), in some embodiments, the described tube comprises an inner diameter between about 3.8 cm and about 7.7 cm, or any subrange thereof. Indeed, in some embodiments, the tube's inner diameter is between about 3.45 cm and about 6.35 cm, or any subrange thereof (e.g., about 4.45 cm±0.5 cm).

In some embodiments, the end of the vacuum tube 102 that connects to a vacuum hose is configured to couple to the vacuum hose in any suitable manner, including, without limitation, by flaring, tapering, and/or having any suitable coupling mechanism. Indeed, in some embodiments, such end of the vacuum tube flairs so as to have an outer diameter that is between about 4.5 cm and about 7.6 cm (or within any subrange thereof). For instance, some embodiments of the vacuum tube flair to have an outer diameter that is between about 4.55 cm and about 5.1 cm.

The wall of the vacuum tube 102 can be any suitable thickness that allows it to function as described herein. Indeed, in some embodiments, the vacuum tube wall is between about 0.25 mm and about 5 mm (or within any subrange thereof). Indeed, in some embodiments, the vacuum tube wall is between about 0.5 mm and about 1.3 mm thick (e.g., about 0.89 mm±0.3 mm).

When the wand head 104 is disposed on a flooring surface such that the wand head and/or the shroud 106 form a seal (or at least a partial seal) on the flooring surface, the distance between the front end 210 of the wand head 104 and the back end 212 of the vacuum tube 102 (shown as L in FIG. 2J) can be any suitable distance. In some embodiments, such distance (L) is between about 50 cm and about 152 cm (or within any subrange thereof). Indeed, in some embodiments, the distance L is between about 91 cm and about 115 cm (e.g., between about 96 cm and about 107 cm).

When the wand head 104 is disposed on a flooring surface such that the wand head and/or the shroud 106 form a seal (or at least a partial seal) on the flooring surface, the distance between the bottom end 214 of the wand head 104 and the top end 216 of the vacuum tube 102 (shown as H in FIG. 2J) can be any suitable distance. In some embodiments, such distance (H) is between about 60 cm and about 120 cm (or in any subrange thereof). Indeed, in some embodiments, the distance H is between about 76 cm and about 105 cm (e.g., between about 83 cm and about 94 cm).

Figure 2D:
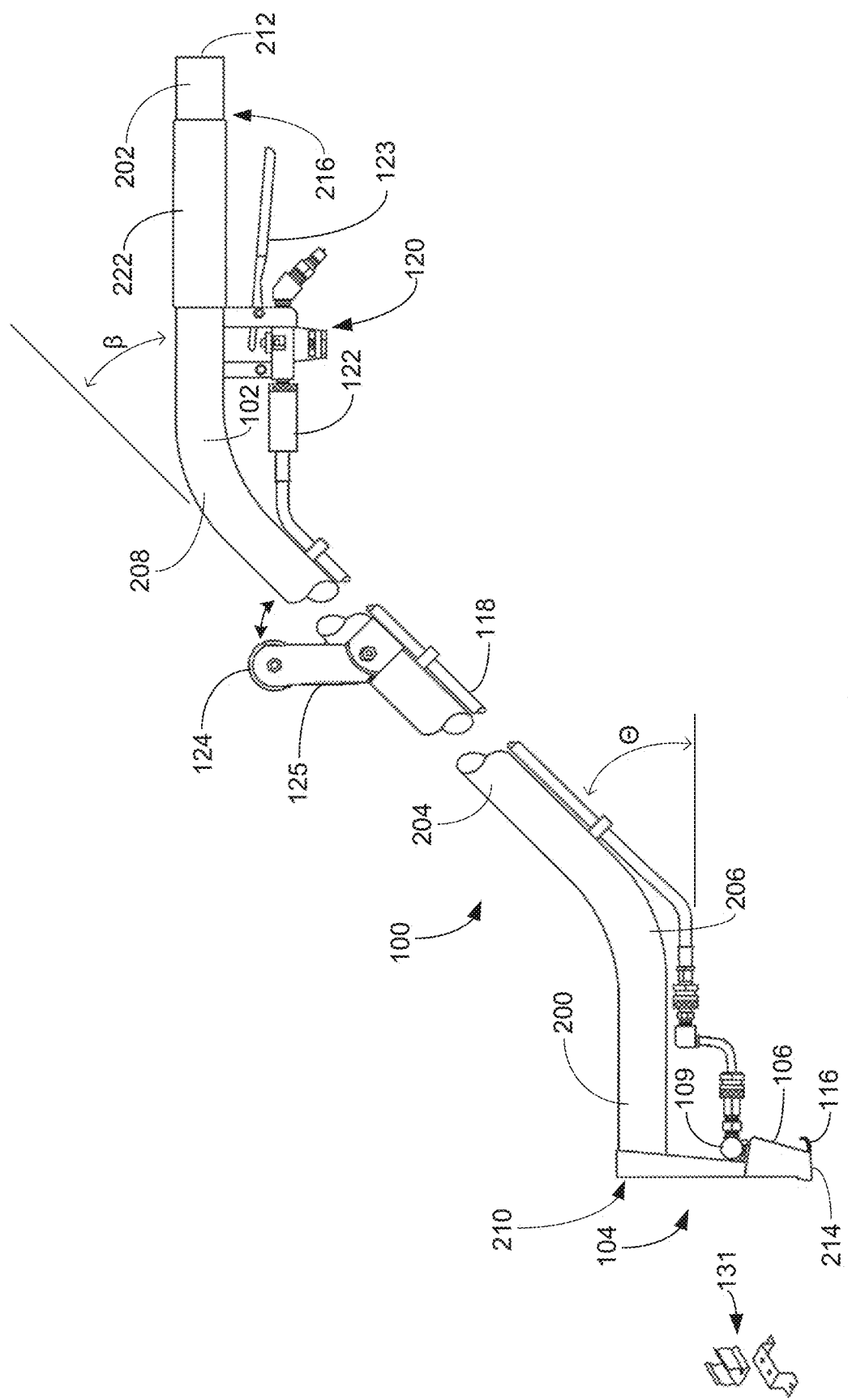
FIG. 2D illustrates a side schematic view of a representative embodiment of the wand.

The vacuum tube 102 can be any suitable shape, and can comprise any suitable number of tubing sections (e.g., a single monolithic tube section or 2, 3, 4, 5, 6, or more sections that couple together) that allows the vacuum tube to perform its described functions. In some embodiments, however, the tube comprises two or more sections (e.g., comprising discrete components and/or a single component having multiple sections) that are at least partially disposed at an angle to each other. Indeed, in accordance with some embodiments, FIGS. 2B and 2D show that the vacuum tube 102 comprises a first section 200, a second section 202, and/or a third section 204, with a first bend 206 (or elbow) disposed between the first 200 and third 204 sections and a second bend 208 (or elbow) disposed between the second 202 and the third 204 sections.

Where the vacuum tube 102 comprises a bend (e.g., a first bend 206, a second bend 208, and/or any other suitable bend) between one or more sections, the various sections of the vacuum tube can have any suitable special relation to each other. Indeed, in some embodiments, the bend 206 between the first 200 and the third 204 section causes a length of the third section 204 (e.g., a longitudinal axis of a portion of the third section) to run with respect to a length of the first section 200 (e.g., a longitudinal axis of a portion of the first section) at an angle θ that is between about 35 degrees and about 70 degrees (or that falls in any subrange thereof). Thus, in some embodiments, a length of the third section runs at an angle to the first section of between about 40 degrees and about 44 degrees (e.g., about 42 degrees±2 degrees).

In some embodiments, the second bend 208 between the second section 200 and the third 204 section causes a length of the third section 204 (e.g., the longitudinal axis of a portion of the third section) to run with respect to a length of the second section 204 (e.g., the longitudinal axis of a portion of the second section) at an angle β that is between about 35 degrees and about 70 degrees (or that falls in any subrange thereof). Thus, in some embodiments, a length of the third section runs at an angle to the second section of between about 41 degrees and about 45 degrees (e.g., about 43 degrees±2 degrees).

Figure 2E:
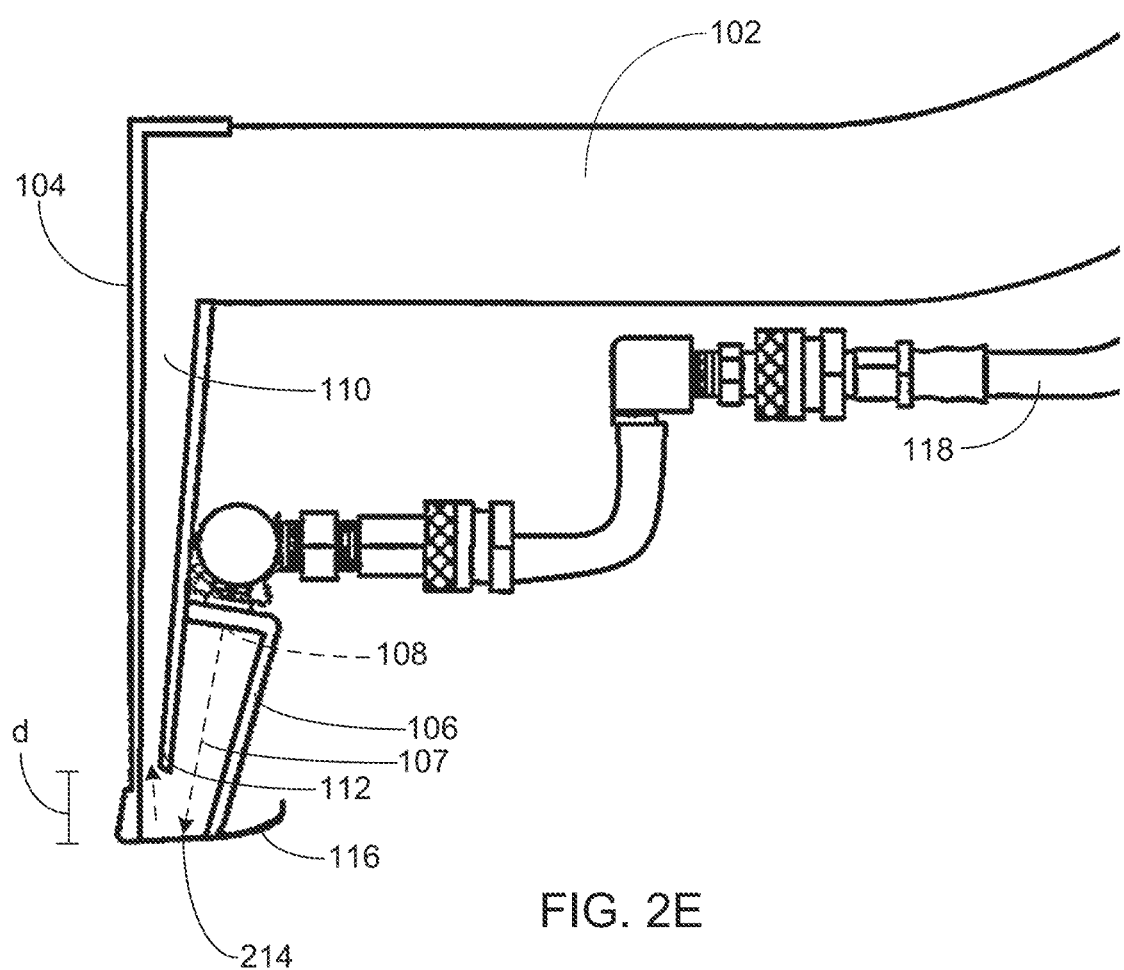
FIG. 2E illustrates a partial, side, cross-sectional view of a representative embodiment of the wand head.
Figure 2F:
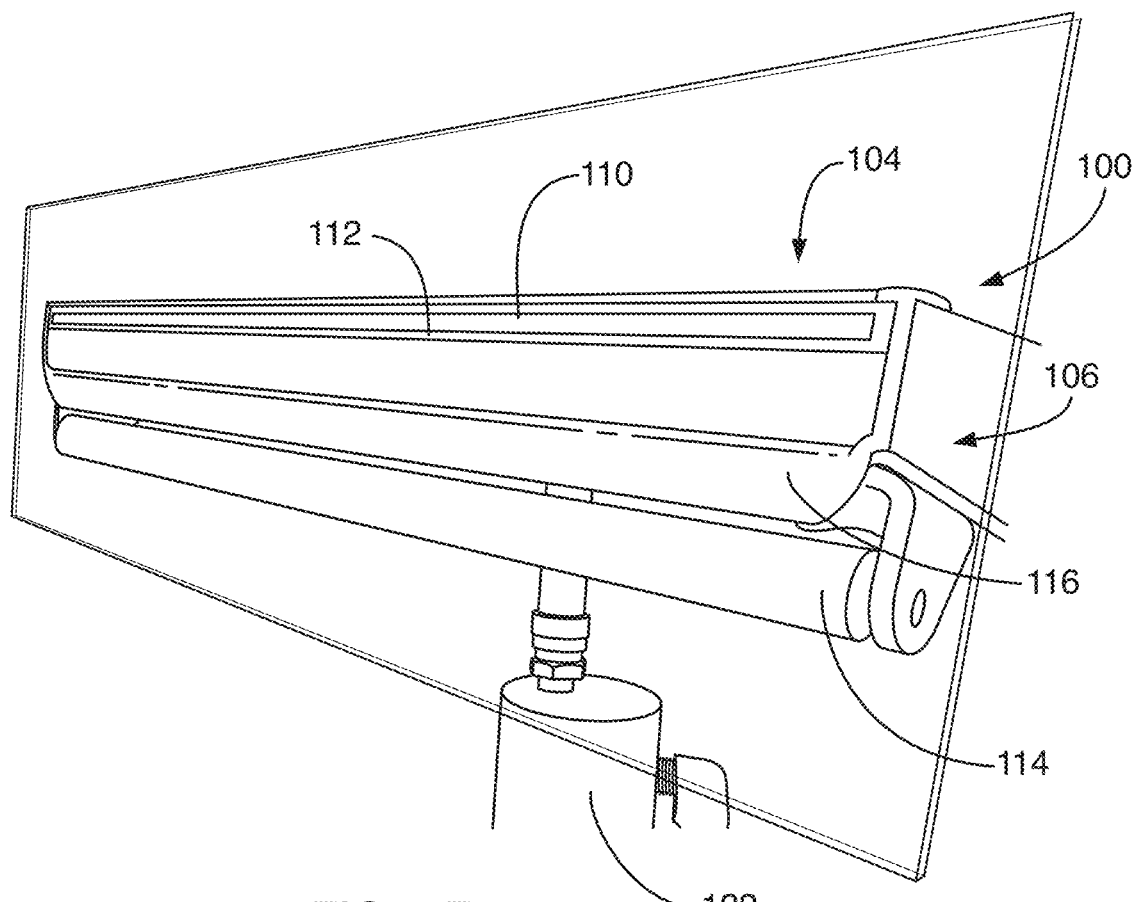
FIG. 2F illustrates a perspective view of the wand head in which the head is in contact with a piece of a transparent material such that a shroud of the wand head and/or the wand head forms at least a partial seal with the transparent material and such that fluid sprayed from one or more jets in the head is allowed to be sucked up into a vacuum port in the wand head in accordance with some embodiments.
Figure 2G:
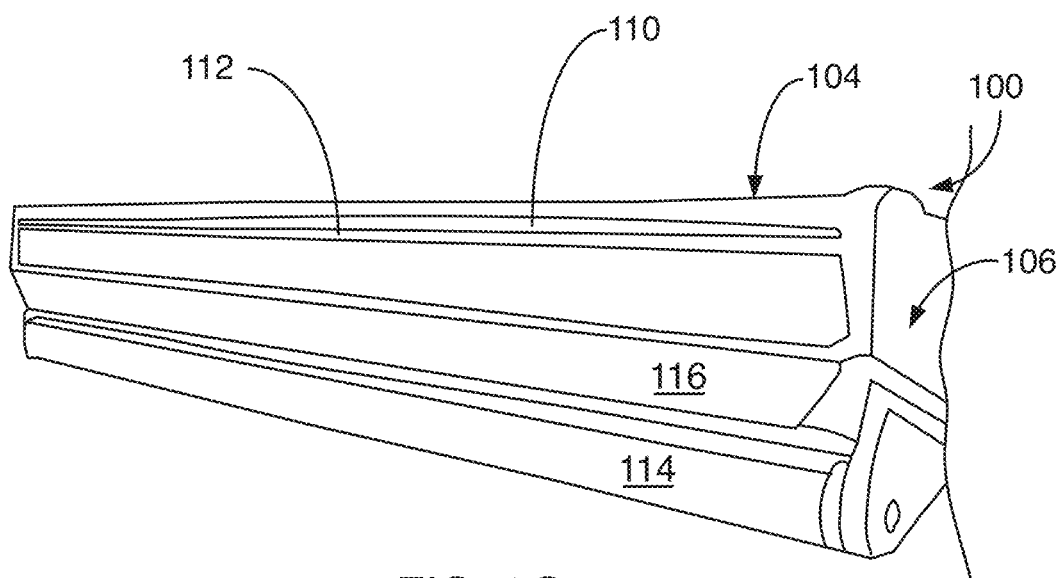
FIG. 2G illustrates a perspective view of a portion of the wand head in accordance with a representative embodiment.
Figure 2H:
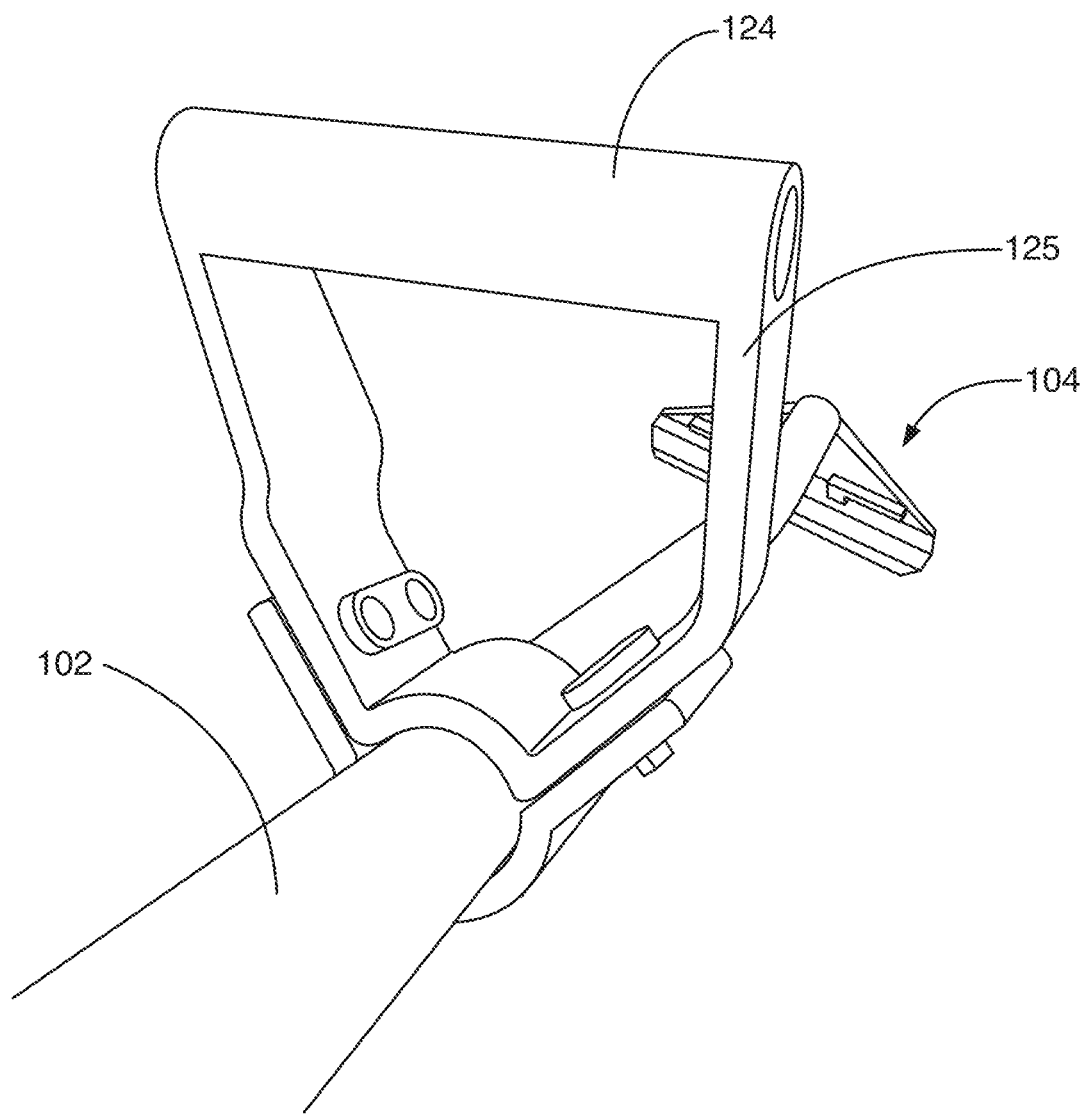
FIGS. 2H-2I illustrate perspective views of a wand handle in accordance with some embodiments.
Figure 2I:
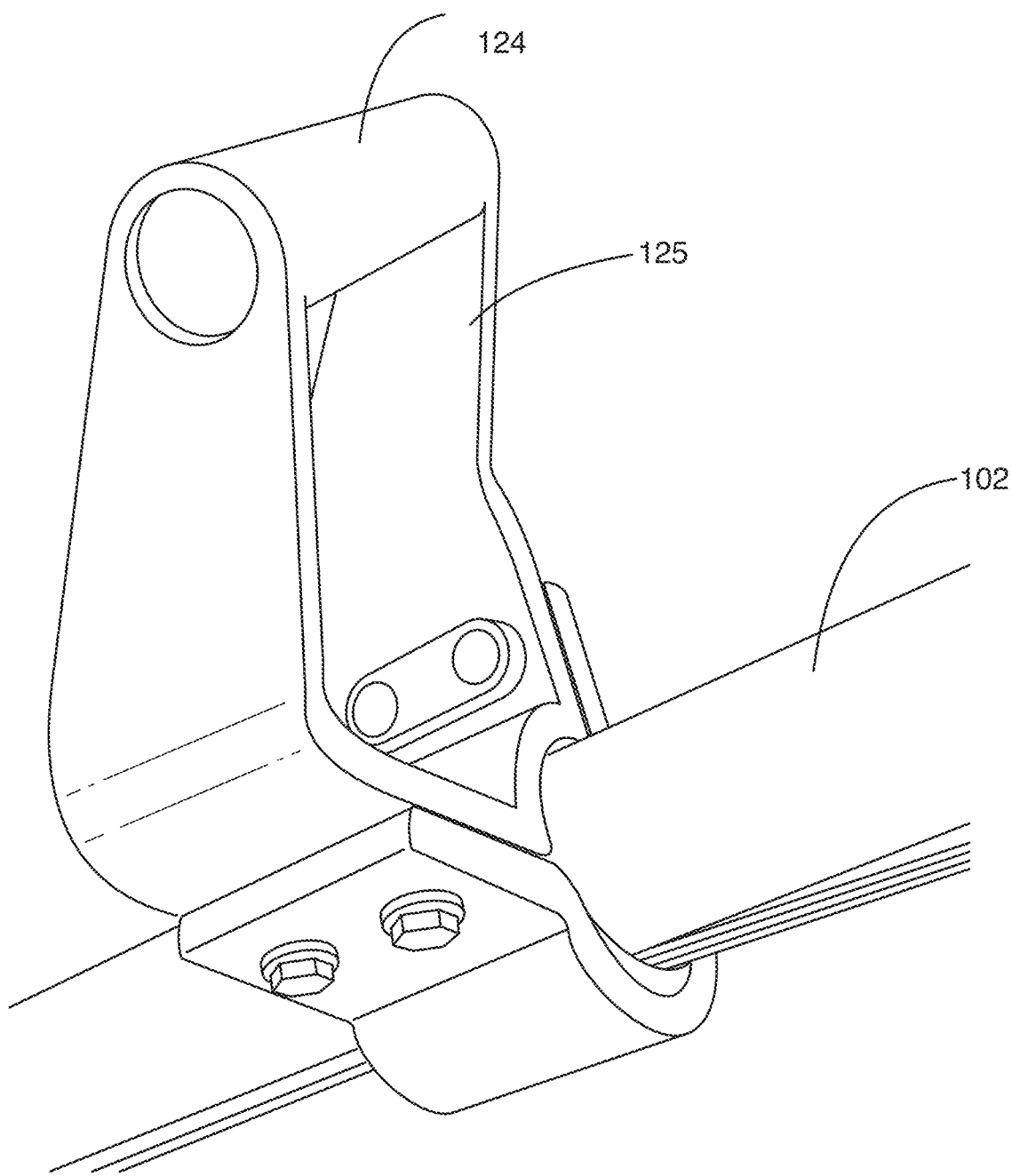
Figure 2J:
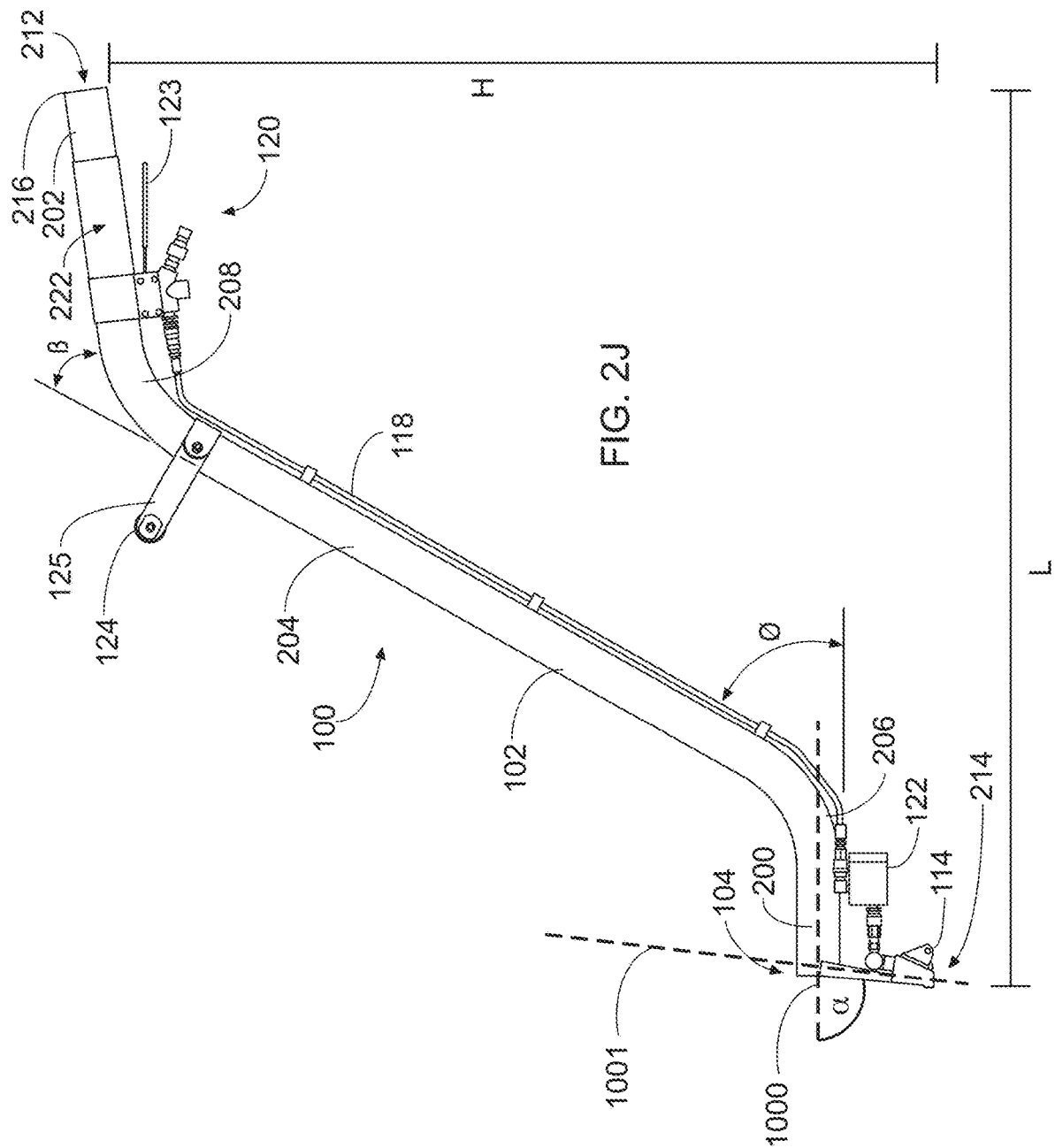
FIG. 2J illustrates a side view of the wand in accordance with some embodiments.
Figure 5:
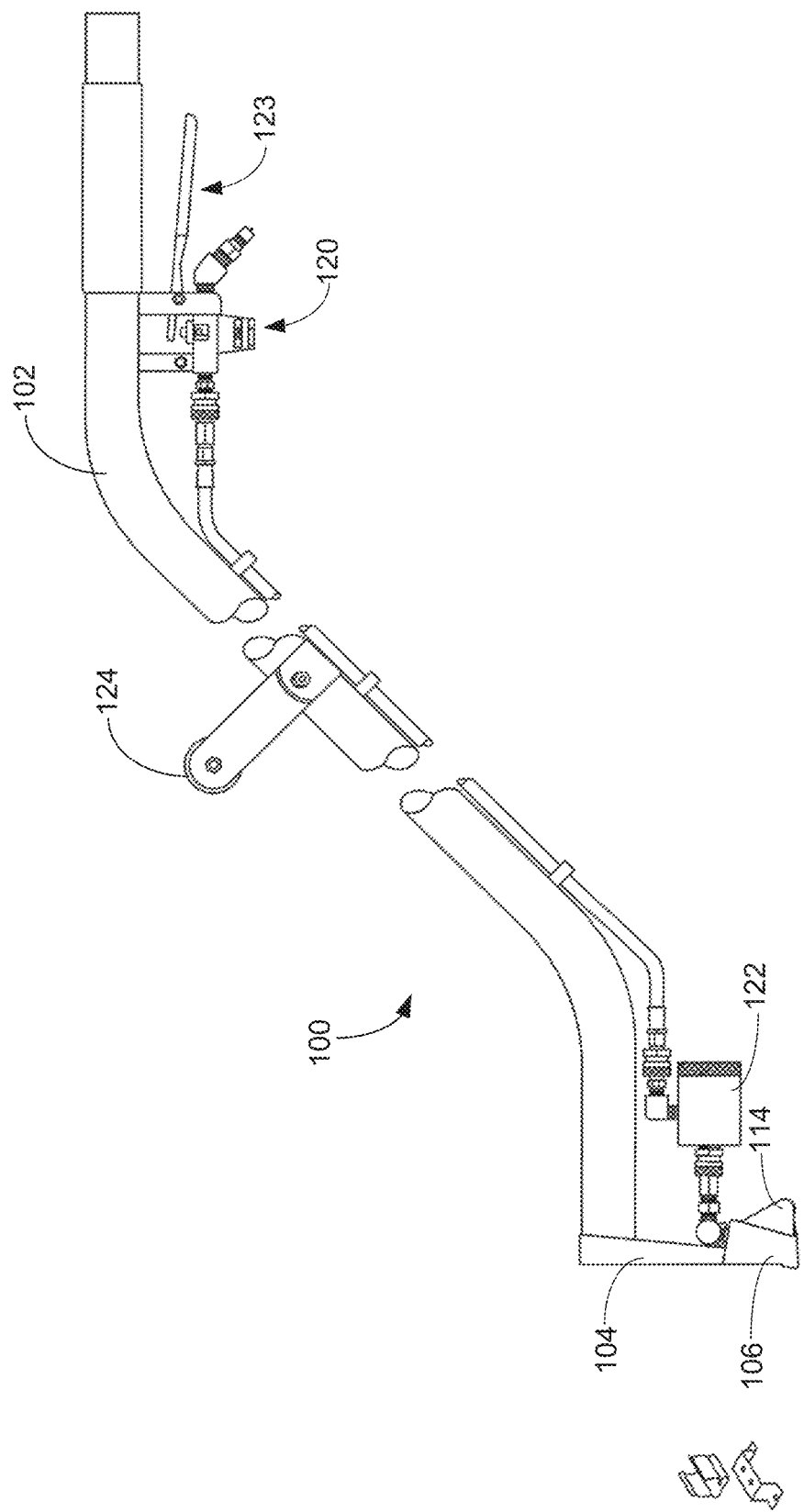
FIG. 5 illustrates a side schematic view of a representative embodiment of the wand.

In some cases, the wand head 104 (or shroud 106) is swept forward with respect to the vacuum tube 102, such that a front face and/or a longitudinal axis 1001 of the wand head runs at an angle that is not perpendicular with respect to a longitudinal axis 1000 of the first section 200. Indeed, in some cases, the front face and/or longitudinal axis of the shroud runs at an angle that is between about 89 degrees and about 60 degrees (or within any subrange thereof) with respect to the longitudinal axis of the first section. By way of non-limiting illustration, FIG. 2J shows an embodiment in which the angle α between the front face of the wand head 104 and the longitudinal axis 1000 of the first section is less 90 degrees (e.g., is about 88 degrees). In this regard, while FIG. 2J shows an embodiment in which the front face and/or the longitudinal axis 1001 of the wand head is swept forward, in some other embodiments, the front face and/or longitudinal axis of the wand head is swept backward so as to run at an non-perpendicular angle with respect to the longitudinal of the first section 200 (so as to have angle that is less than about 90 (when such angle opens towards the user operating the wand).

While the various wand angles can perform any suitable function, in some embodiments, they make it significantly easier to slide the wand head 104 across a flooring surface (e.g., without the wand head 104 digging (or "shoveling") into the flooring surface than is possible with some competing devices). As a result, some embodiments of the described wand are configured to be used relatively easily, while causing less user fatigue than do some competing devices.

Indeed, in some embodiments, by placing the wand head 104 at a suitable distance and/or angle from the user (as described above), the user can move the wand head relatively more easily than could be done if the wand head were too close to, not swept from a perpendicular angle with respect to the first section 200, and/or at too steep of an angle to the user (e.g., thus causing the wand head to dig into and/or to skip across the flooring). Indeed, in accordance with some embodiments, the length of the vacuum tube 102 in combination with the various angles in the tube (as discussed above) have provided surprising and unexpected results. Indeed, while some conventional devices that are shorter and/or that have inappropriate angles cause a user to push the wand into the flooring and can thereby result in rapid user fatigue, some embodiments of the described wand (with its described angles and length) place the wand head in an optimal working position that allows users of different heights to easily push and/or glide the wand head across a flooring surface being cleaned with significantly less user fatigue that is caused by some competing devices.

In some embodiments, the length of one or more sections (e.g., the first 200, second 202, and/or third 204 sections) and/or other portions of the vacuum tube 102 are optionally adjustable to allow the tube to be resized and/or otherwise tailored for individual users and/or uses. Accordingly, in some such embodiments, the distances L and/or H are selectively adjustable. In such embodiments, the length of the vacuum tube and/or any portion or section thereof can be selectively adjustable in any suitable manner, including, without limitation, via a telescoping mechanism that comprises a tube within a tube and that allows one tube to slide with, and to be selectively locked and released (e.g., via a twist-lock telescoping mechanism, a detent mechanism, a mechanical engagement, a frictional engagement, one or more fasteners, and/or in any other suitable manner), with a respect to another tube of the vacuum tube.

In some embodiments, the vacuum tube 102 is optionally configured such that the angle between one or more sections (e.g., sections 200, 202, 204, etc.) is adjustable to allow the tube to be tailored for users of different size and/or different uses. In such embodiments, the various angles of the vacuum tube can be adjusted in any suitable manner. Indeed, in one example, an angle between two sections in the tube is adjusted by switching a bend (e.g., 206 and/or 208) in the tube with another bent section (e.g., an elbow joint or other suitable component) and/or another section having a different desired angle. In this example, the various bent and/or other sections can be coupled to the vacuum tube in any suitable manner, including, without limitation, via one or more detent mechanisms, friction fittings, mechanical connection mechanisms, fasteners, adhesives, welds, and/or any other suitable mechanisms.

In another example of a method for modifying the shape of the vacuum tube 102, some embodiments of the vacuum tube comprise one or more flexible components (e.g., a flexible tube with an adjustable rigid scaffolding that is configured to selectively lock in and be released from a desired orientation, a flexible exhaust-pipe-like tube, and/or any other suitable component) that allows an angle between two or more portions of the vacuum tube to be selectively adjustable and selectively maintained.

With reference now to the wand head 104, the wand head can comprise any suitable feature that allows it to apply a fluid (e.g., via one or more nozzles, orifices, sprayers, and/or other jets 108) to flooring being cleaned and to allow such fluid and/or debris to be drawn from the flooring (e.g., via one or more vacuum ports 110 that are configured to funnel and/or otherwise direct fluid, debris, air, and/or other materials to the vacuum tube 102). In this regard, some embodiments of the wand head comprise 1, 2, 3, 4, 5, 6, 7, 8, 9, 10, or more jets and/or vacuum ports. Indeed, in some embodiments, the head comprises 3-6 jets (e.g., coupled to a jet manifold 109 or otherwise connected to one or more feed lines 118) and one vacuum port.

Where the wand head 104 comprises one or more jets 108 and vacuum ports 110, the jets and vacuum ports can be disposed in and/or on the head with any suitable relation to each other. Indeed, although some embodiments of the head comprise jets in front of the vacuum port (e.g., distal to the vacuum port or the operator), in some other embodiments, the jets 108 (and/or jet manifold 109) are disposed (as shown in FIG. 2E) behind the vacuum port (e.g., proximal to the port or the operator). In some of these latter embodiments, the wand is configured to be a pull wand—allowing fluid that is sprayed from the jets to be rapidly sucked up when the wand is being pulled (e.g., backwards).

In some embodiments, the jets 108 and/or the vacuum port 110 are at least partially disposed in and/or in fluid communication with a shroud 106. In other words, some embodiments of the head 104 comprise a sealed loop (or at least partially sealed loop) system in which fluid sprayed from the jets within the shroud is allowed to contact the flooring being cleaned and to then be sucked up into the vacuum port in a relatively short period of time. By way of non-limiting illustration, FIG. 2E shows an embodiment in which the shroud 106 is configured to extend around a portion of the head 104 so as to extend around a spray, mist, curtain, and/or other effluent 107 of the jets 108 and to form a seal (or at least a partial seal) with a flooring surface (not shown) upon which the head rests.

In some cases, the vacuum port is referred to herein as a first chamber in the wand head (the first chamber being disposed in proximity to the vacuum tube 102), and the portion the shroud 106 to which the jets 108 are coupled is referred to as the second chamber, with the first and second chambers being at least partially separated by a breaker bar 112, as referred to below.

Indeed, in some embodiments, to help fluid flow from the jets 108, across the flooring, and into the vacuum port 110, the wand head 104 comprises a recess, surface, and/or other form of breaker bar 112 that is recessed within the shroud 106 (e.g., between a space of the shroud (the second chamber) and the vacuum port the first chamber) such that one or more surfaces of the shroud extend past (e.g., below) the breaker bar. In some such embodiments, by having the breaker bar be recessed within the shroud, the shroud (and/or head) is able to contact and form at least a partial seal with the flooring surface while the breaker bar is held slightly higher up above the flooring to allow fluid to rapidly pass from the flooring into the vacuum port. Thus, in some embodiments, the recessed breaker bar allows fluid leaving the jets and contacting the flooring to rapidly change direction (e.g., doing a U-turn) and to pass into the vacuum port. As a result of this sealed (or semi-sealed) loop system, some embodiments of the wand are configured to force the fluid across the flooring (e.g., through carpet) and then to suck such fluid up into the vacuum port without allowing the fluid to flood the flooring and/or to settle into flooring (e.g., the carpet backing and/or padding). Thus, some embodiments of the described systems are capable of cleaning flooring with high-pressure fluid and then allowing such flooring to dry significantly faster than do some other conventional methods and devices.

Where the wand head 104 comprises a recessed breaker bar 112, the breaker bar (or a portion thereof) can terminate and/or be disposed at any suitable distance from (e.g., above) the bottom end 214 of the wand head 104 and/or the shroud 106 that allows the wand head to function as described herein. Indeed, in some embodiments, the breaker bar is disposed at a distance (as shown by d in FIG. 2E) between about 2 mm and about 3 cm (or any subrange thereof) above the head's bottom end. Indeed, in some embodiments, the breaker bar is disposed between about 0.5 cm and about 1.5 cm above the head's bottom end.

In some embodiments, to allow the wand head 104 to be adjusted and/or optimized for various types of flooring (e.g., tile, shag carpet, etc.) with various characteristics, the breaker bar 112 is adjustably attached to the wand head such that the breaker bar (or a portion thereof) can be selectively raised and lowered in the head (and/or such that a portion of the shroud and/or head can be raised and lowered with respect to the bar). In such embodiments, the breaker bar (and/or shroud and head) can be adjustable in any suitable manner, including, without limitation, by being coupled to one or more threaded fasteners, detent mechanisms, sliding ratchet mechanisms, grooves into which portions of the head (or an attached object) slidably fit, one or more lever mechanisms that cause the bar (and/or the shroud and/or head) to move when a lever is moved, and/or any other suitable mechanism that allows at least a portion of the breaker bar (and/or the shroud/head) to be raised and/or lowered in the head. Indeed, in some embodiments, the breaker bar is slidably coupled within the head via one or more threaded fasteners that can be loosened to move, and tightened to secure, the bar.

With reference now to the roller 114, some embodiments of the wand 100 optionally comprise 1, 2, 3, 4, 5, 6, 7, 8, 9, 10, or more wheels, bearings, casters, and/or other rollers that are configured to help the wand head 104 be moved across a flooring surface with relatively little effort. While the rollers can be disposed in any suitable location on the wand (e.g., in front, behind, and/or to the side of the vacuum port 110), in some embodiments, the roller is disposed behind the vacuum port, the jets 108, and the shroud 106 (e.g., as shown in FIGS. 2B, 2F, 2G, 3A, 4A, 5, 6, and 10). In some such embodiments, by placing the roller behind the port (e.g., proximal to the operator), the wand can be used to clean right up next to walls and other objects.

Where the wand 100 comprises one or more rollers, the rollers can have any suitable width. In some embodiments, however, the roller (and/or a plurality of rollers coupled side to side) extends across a substantial width of the wand head 104. While such a roller (or rollers) can perform any suitable function, in some cases, they act to lay down a portion of the flooring (e.g., carpet and/or other material) that is being cleaned such that a larger portion of strands of the flooring (e.g., carpet or other material) is exposed to the spray and/or vacuum forces provided through the wand head.

Figure 6:
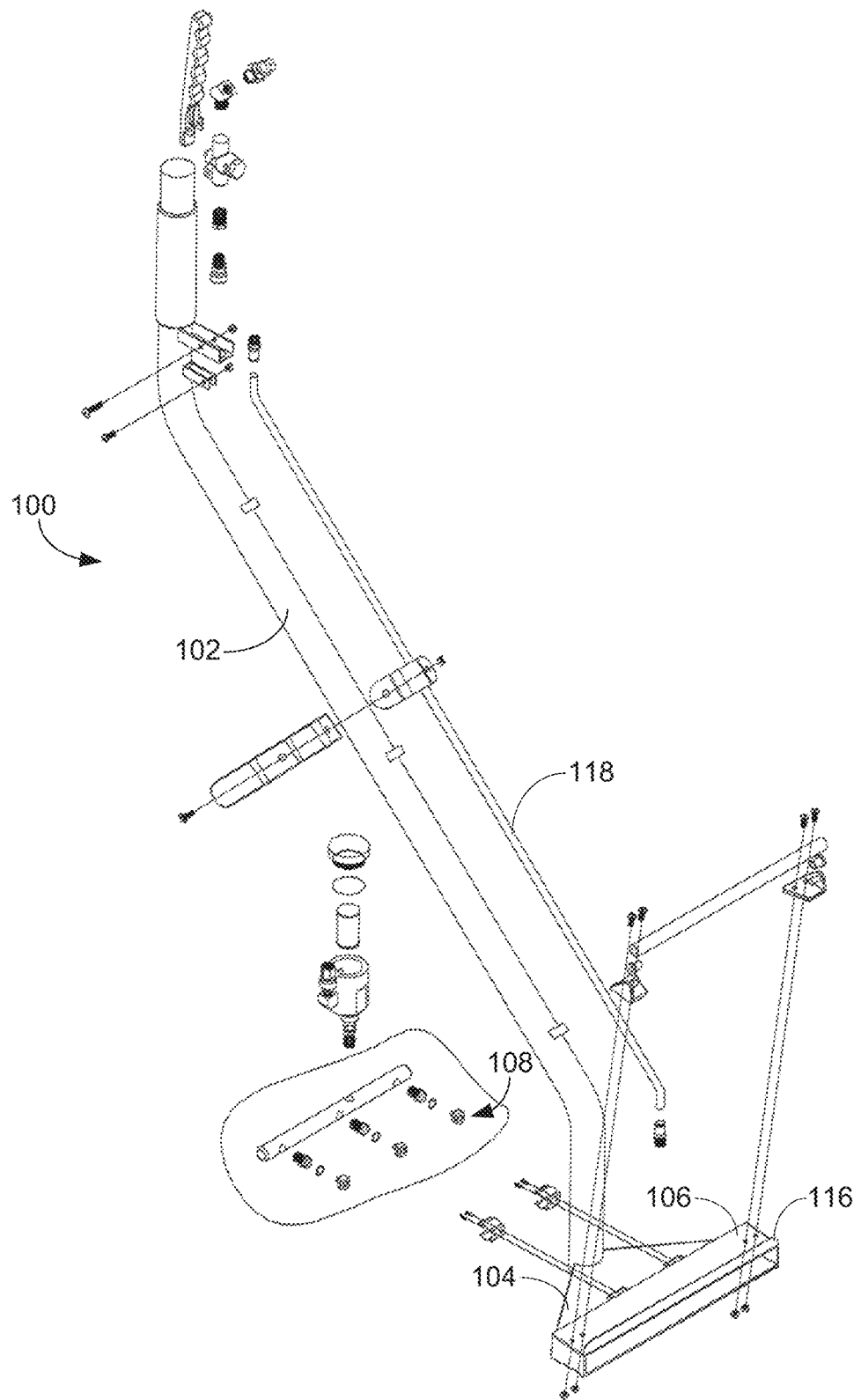
FIG. 6 illustrates a perspective, exploded view of a representative embodiment of the wand.
Figure 10:
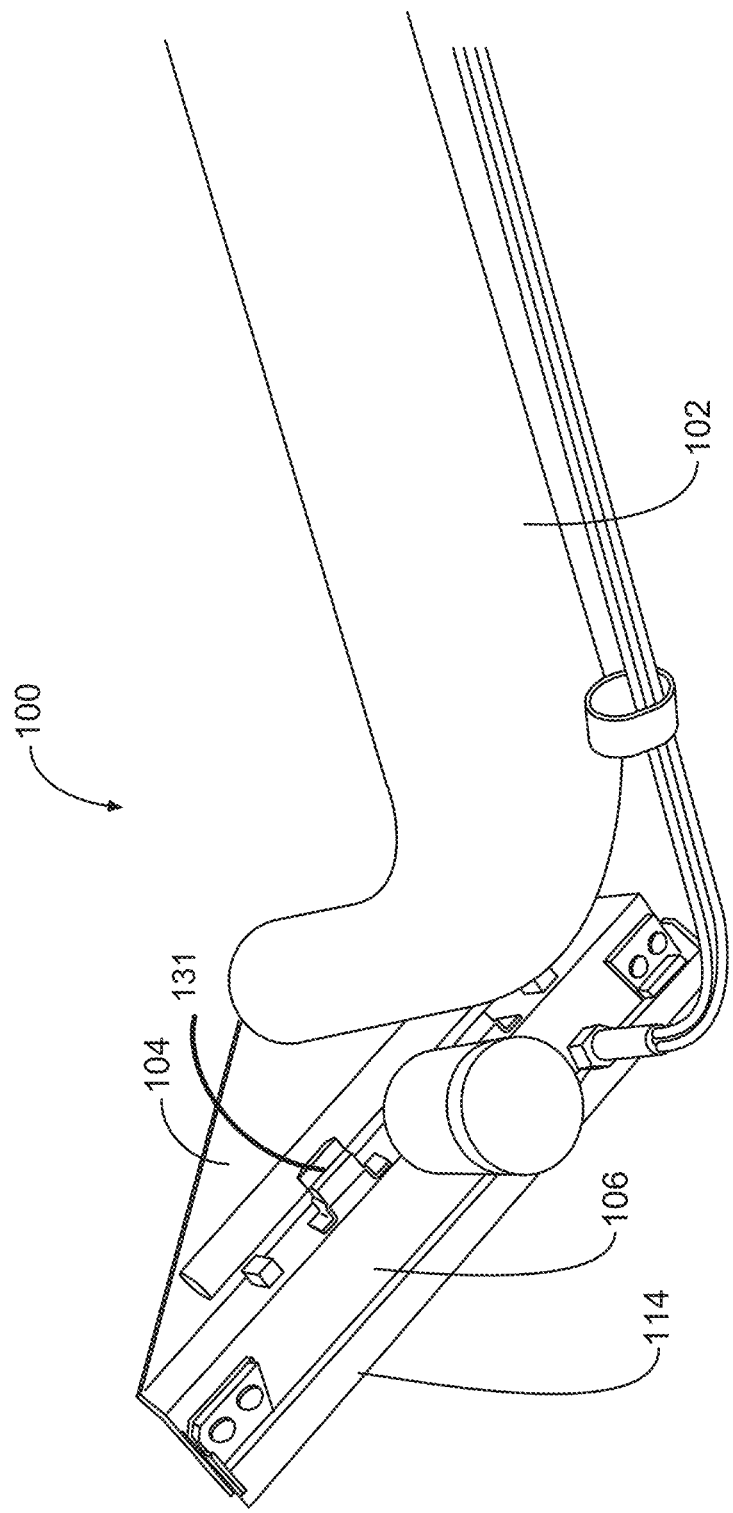

In some embodiments, the roller 114 is optionally adjustable such that it can be moved up or down on the wand head 104. In this manner, the wand 100 can be adjusted to allow operators of various heights to use the wand in a position that is comfortable to the individual operators while allowing such operators to maintain at least a partial seal between the shroud 106 and/or the head and the flooring being cleaned. Indeed, in some embodiments in which the roller's height is fixed, a relatively tall operator may hold the wand at such an angle that the roller does not contact the flooring throughout the operator's full stroke of the wand—thus making it hard for the operator to force the wand head across the flooring. In contrast, in some embodiments in which the roller's height is fixed (e.g., at the same height as it was for the relatively tall operator), an operator that is relatively short may hold the wand at such an angle that the roller contacts the flooring and acts as a fulcrum that lifts the front of the head off the flooring and prevents the shroud from forming a desirable seal with the flooring. Thus, in some embodiments, the adjustable roller can allow an operator to tailor the wand to the operator's size and needs, while allowing the wand to clean flooring surfaces.

Where the roller 114 is selectively adjustable, the roller can be adjusted in any suitable manner, including, without limitation, via one or more detent mechanisms, ratchet mechanisms, level mechanisms, the loosening and tightening of one or more screws, by being able to attach the roller to the head at more than one position (e.g., in a variety of connection points), and/or in any other suitable manner. Indeed, in some embodiments, the roller is coupled to one or more brackets that can be coupled to the rear of the head in multiple positions (e.g., via the tightening and/or loosening of one or more screws, as shown in FIGS. 6 and 10).

In place of, or in addition to, the roller 114, some embodiments of the wand head 104 comprise one or more angled surfaces, rounded surfaces, glides, skis, and/or any other suitable lips 116 that extend from the head and/or the shroud 106 that help the head to easily slide across flooring surfaces (e.g., without skipping across the flooring surface and/or requiring undue amounts of force to move the head). While such lips can extend from any suitable portion of the wand head and/or the shroud, including, without limitation, from a front side, back side, right side, left side, corner, and/or any other suitable portion of the wand head and/or the shroud, FIGS. 2D-2G show some embodiments in which the lip 116 extends from a back side of the shroud 106. Thus, in some embodiments, the wand head is able to slide across flooring relatively easily, due to the lip, while still having a front side of the wand head (and/or sides) be able to clean up to one or more walls, pieces of furniture, and/or any other suitable object. Additionally, as mentioned above, while some embodiments of the wand head comprise a lip but do not include any additional wheels or rollers, in some other implementations, the lower back side of the wand head comprise both a lip and one or more rollers.

With respect now to the trigger assembly 120, the trigger assembly can comprise any suitable mechanism that allows a user to selectively start, stop, increase, decrease, and/or otherwise control the flow of fluid through the feed line 118 and jets 108. Indeed, FIGS. 2B, 2D, 4A, and 5 show some embodiments in which the trigger mechanism 120 comprises a manually controlled valve that is opened when the trigger lever 123 is squeezed and closed when the trigger lever is released. In some other embodiments that are not shown, the trigger mechanism comprises one or more catches, detents, and/or other mechanisms that are configured to selectively catch and/or otherwise retain the trigger lever in a desired position so as to provide a desired flow of fluid through the feed line. Indeed, in some embodiments, the trigger mechanism functions much like a gas pump trigger that is configured to have a lever (e.g., the trigger lever 123 and/or another lever) be selectively captured in one or more catches and then to be released from such catches when the trigger lever is squeezed (and/or as otherwise determined, for instance, when the system determines that a sufficient or exorbitant amount of fluid has been disposed in the flooring, as discussed below).

In still other embodiments, the trigger mechanism 120 comprises one or more electronically controlled valves, pneumatically actuated values, solenoids, and/or other valve mechanisms that are that are configured to allow a user to easy control fluid flow through the feed line 118. Thus, in some such embodiments, the described systems and methods reduce user fatigue (e.g., fatigue associated with gripping the trigger lever 123 for long periods of time).

In accordance with some embodiments, the wand 100 is configured to provide fluid through one or more of the jets 108 in a pulsed, pulsated, sonicated, choppy, shockwave, turbulent, vibrated, and/or other pulsated manner that does not provide the spray to the surface that is being cleaned in a steady flow. In this regard, the wand (and/or system 10) can comprise any suitable pump, valve, sonicator, pulsing device, solenoid, actuator, oscillating valve, and/or other device that is configured to provide fluid to the surface being cleaned in a pulsated or sonicated manner. Indeed, in some embodiments, the valve comprises a spring loaded ball valve that is configured to have the ball move back and forth in the valve to oscillate pressure of the liquid passing through the valve. In any case, a mechanism for pulsating fluid through the wand and/or jets can be powered and/or actuated in any suitable manner, including, without limitation, hydraulically (e.g., by flow of fluid from the cell), electrically (e.g., powered by the mains, a battery, and/or in any other suitable manner), pneumatically, and/or in any other suitable manner.

While any suitable mechanism can be used to pulse fluids through wand 100 (e.g., the jets 108), in some embodiments, the trigger assembly 120 is used with one or more pulsing valves (e.g., pulse valve, pulse jet valve, pulse solenoid valve, and/or other valves) and/or other mechanisms that are configured to pulse the spray that is applied to flooring (and/or any other surface being cleaned). In some such embodiments, such pulsing can allow the wand to apply fluid to the flooring at relatively high, pulsated pressures, and to thereby help dislodge debris and to otherwise clean such flooring.

With reference now to the filter 122, some embodiments of the described wand 100 comprise one or more filters that are configured to perform any suitable purpose, including, without limitation, preventing debris in the feed line 118 from clogging a jet 108. In such embodiments, the wand can comprise any suitable number of filters (e.g., 1, 2, 3, 4, 5, 6, or more) that are disposed in any suitable location. Indeed, in accordance with some embodiments, FIG. 2B shows the wand 100 comprises a single filter 122 that is disposed adjacent to the wand head 104 (e.g., coupled to the first section 200). In accordance with some other embodiments, however, FIG. 2D shows an embodiment in which the filter 122 is disposed at or between the first bend 206 and the end 212 of the vacuum tube 102. Indeed, while the filter can be disposed in any suitable location (e.g., between a midpoint of a length of the third section 204 and the tube's end 212), FIG. 2D shows an embodiment in which the filter 122 is coupled to the second section 202 (e.g., at and/or near the second bend 208). In this regard, while there may be several reasons to place the filter adjacent to the wand head, in some cases, placing the filter near the second section 202 can make the wand head lighter and easier to move and may result in less fatigue to the user (especially, where the second and/or third sections of vacuum tube are strapped (e.g., via a shoulder strap, a belt loop strap, etc.) and/or otherwise connected to the user to reduce user fatigue).

With reference now to the handle 124, the wand 100 can comprise any suitable gripping surface and/or handle that allow a user to grab and maneuver the wand as desired. By way of non-limiting illustration, FIG. 2B shows an embodiment in which the wand 100 comprises a gripping surface 222 disposed on the second section 202 and a handle 124 that is coupled to the third section 204 of the vacuum tube 102.

Where the handle 124 is coupled to the third section 204 of the vacuum tube 102, the handle can be coupled to the tube in any suitable manner and in any suitable orientation. Indeed, FIG. 2B shows that, in some embodiments, the handle 124 is coupled to the tube 102 via a handle support 125 that extends substantially perpendicularly from the tube. In accordance with some other embodiments, however, FIG. 2D shows the handle support 125 extends from the tube 102 at an acute angle, towards the back end 212 of the vacuum tube 102. Additionally, FIGS. 2H and 2I show that, in some embodiments, the handle support 125 is shaped so that the handle 124 is disposed along a length of the tube closer to the tube's back end 212 (not shown in FIGS. 2H and 2I) than is the point at which the handle support is coupled to the tube 102. In still other embodiments (not shown) the handle support is angled towards the front end of the vacuum tube (e.g., at an acute angle) and/or is shaped such that the handle is disposed closer to the wand head 104 (along a length of the tube) than is the point at which the handle support couples to the tube.

In addition to the aforementioned components, the described wand 100 can comprise any other suitable component or characteristic that allows it to function as described herein. Some examples of such components include, but are not limited to, one or more jet manifolds 109 that are configured to direct fluid from the feed lines to the jets 108; plastic, metal, and/or any other suitable clips 131; ties; belts; straps; fasteners; mechanical engagements; frictional engagements; and/or other mechanisms that are configured to selectively and/or permanently couple the jet manifold to the wand head 104, caps, manifold covers, fittings, connectors, valve connectors, disconnects (e.g., quick disconnects or otherwise), check valves, filter housings, bushings (e.g., for the roller 114), bearings, jet housings, pressure valves (e.g., to allow air into the shroud when pressure drops below a set level and/or for any other suitable purpose), shells, lights, pressure gauges (e.g., to determine vacuum pressure in the vacuum tube 102 or for any other suitable purpose), agitators, and/or other suitable components.

As another example of a suitable component, some embodiments of the described wand 100 (and/or a system comprising the wand) include one or more sensors that determine how much fluid has been applied to (and/or remains at) a flooring surface. Indeed, in some embodiments, the wand comprises one or more moisture sensors that determine the moisture level of the flooring over which the wand passes. In some such embodiments, the wand and/or a system comprising the wand is configured to provide an indication of the moisture level of the flooring (e.g., via one or more lights, sounds, displays, and/or other signals) and/or to automatically increase, decrease, start, stop, and/or otherwise control the amount of fluid that is sprayed from the wand head based on such moisture level.

In some other embodiments, the wand 100 (and/or a system comprising the wand) is configured to determine how much fluid the wand lets out and how much fluid the wand sucks up (e.g., to determine how much fluid is left in the flooring and/or for any other suitable purpose). In such embodiments, the wand and/or its system can make such determinations in any suitable manner. Indeed, in some embodiments, the wand comprises one or more sensors that determine how much fluid is dispensed through the head (e.g., one or more flow meters, fluid level sensors, electric eyes, mass sensors, scales, moisture sensors, fluid sensors, and/or any other suitable sensors that are capable of determining how much fluid is dispensed from the jets) and one or more sensors that determine how much fluid has been sucked up through the vacuum tube 102 (e.g., one or more flow meters, fluid level sensors, electric eyes, mass sensors, scales, moisture sensors, fluid sensors, and/or any other suitable sensors that are capable of determining how much fluid has been sucked up through the vacuum tube).

Figure 9:
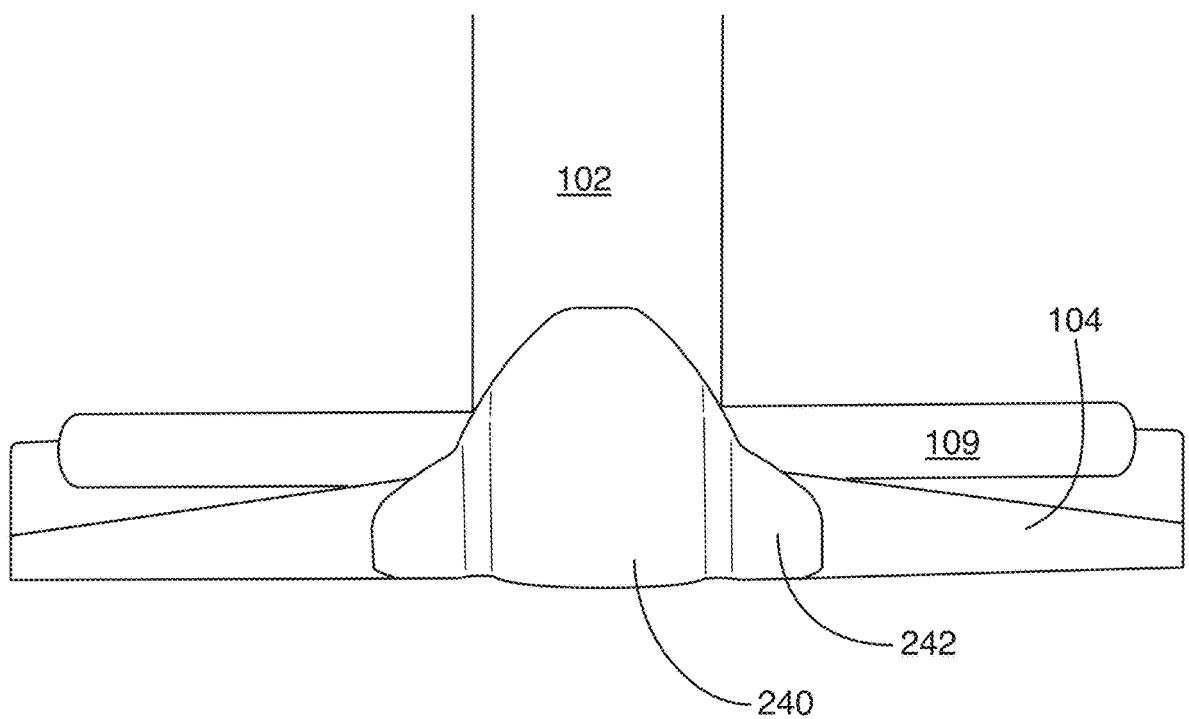

As still another example, some embodiments of the wand 100 are configured to provide additional strength to the connection between the vacuum tube 102 and the wand head 104. While this can be accomplished in any suitable manner, FIG. 9 shows that, in some embodiments, a collar 240 with one or more gussets 242 and/or other supports is welded, adhered, riveted, and/or otherwise coupled between the wand head 104 and the vacuum tube 102.

As another example, some embodiments of the wand head 104 and/or the shroud comprise a lower section that is adjustably coupled to the wand head (e.g., via one or more mechanical fasteners, mechanical mechanisms, frictional engagements, detents, clamps, and/or other suitable mechanisms) such that an angle of such lower section can be adjusted with respect to an upper portion of the head and/or the vacuum tube. In some such embodiments, the head can be adjusted such that the back end 212 of the vacuum tube can be raised or lowered while the head is able to keep a seal (or at least a partial seal) with the flooring being cleaned.

Figure 7:
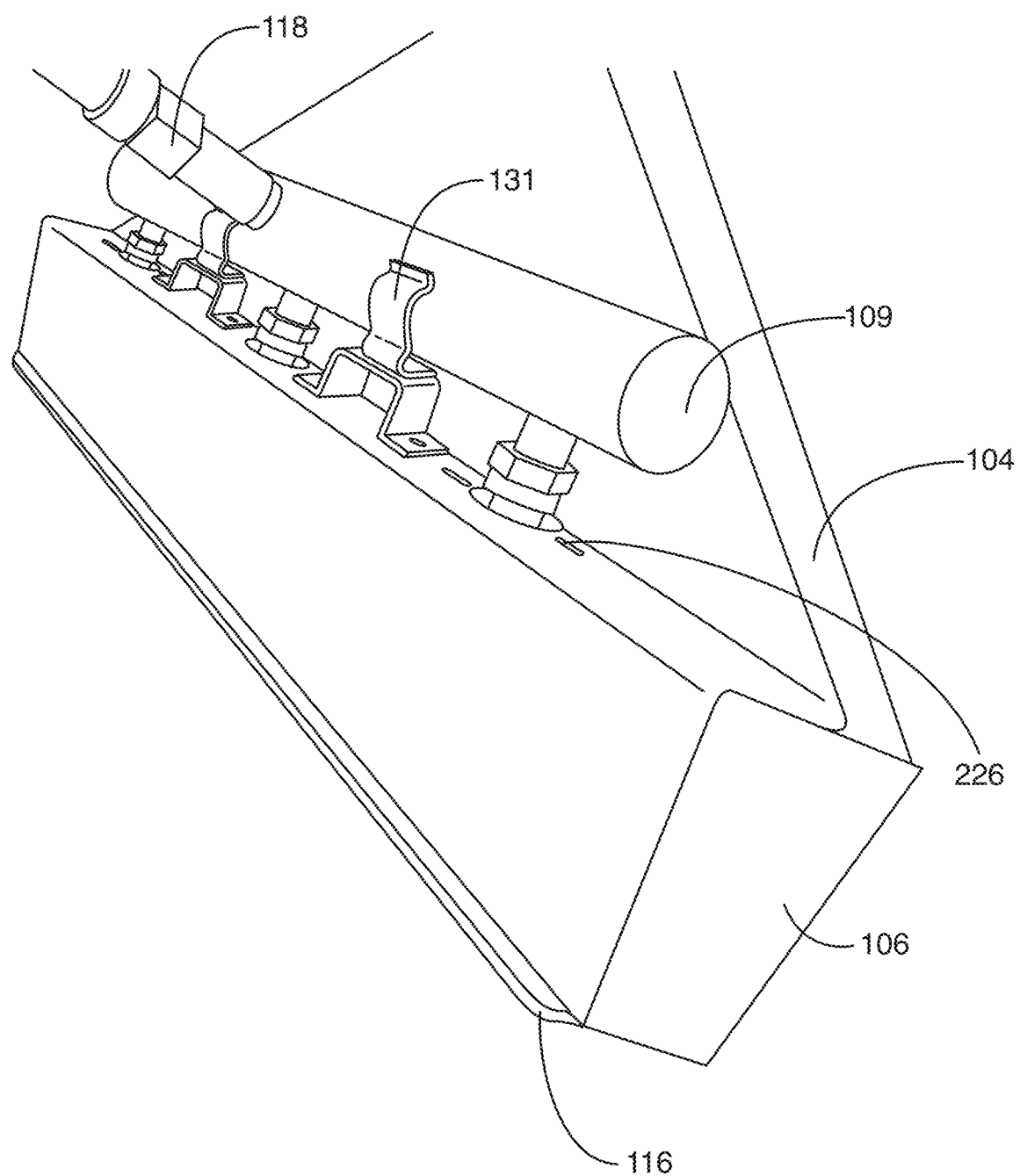
FIGS. 7-10 each depict a perspective view of a portion of the wand head in accordance with some representative embodiments.
Figure 8:
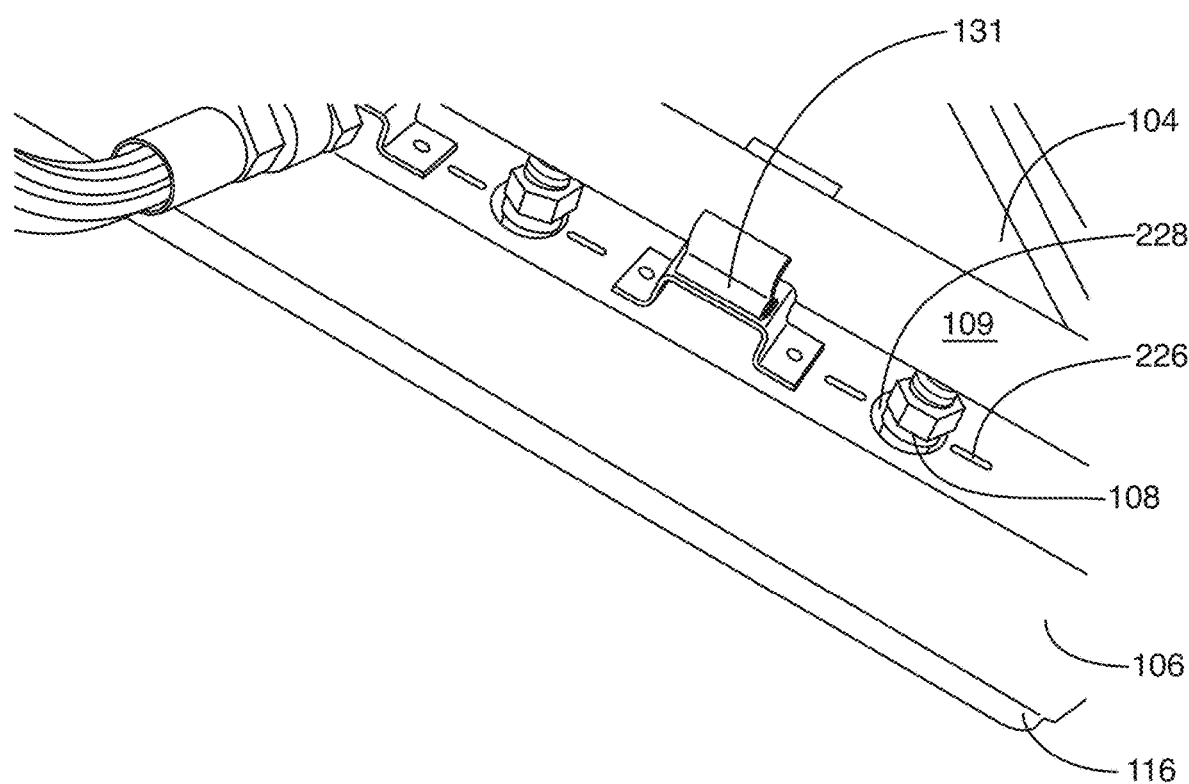

As an additional example of another suitable component, some embodiments of the described wand head 104 and/or the shroud 106 comprise one or more air inlets that allow air to enter into the head and/or the shroud when the head is forming (or substantially forming) a seal with a flooring surface. Accordingly, in some such embodiments, the head is able to form a seal with the flooring while still having enough air flow to suck fluid and/or debris up into the vacuum tube 102. Additionally, in some embodiments, such inlets allow the head to form a relatively tight seal with a surface (e.g., flooring) without placing undue strain on a vacuum's motor. Indeed, while such inlets can perform any suitable function, in some embodiments, the inlets are sized, shaped, and placed to allow air to flow into the inlets to improve a spray pattern of the jets 108. Additionally, in some cases, the air inlets allow air to flow through the air inlets, across a surface being cleaned, then up into the vacuum tube 102 while the shroud head 104 is forming a seal with a surface that is being cleaned. As a result, in some such embodiments, the inlets allow the wand to provide high level of suction when the bottom surface of the shroud is in contact with a surface that is being cleaned. In any case, while such vents can be disposed in any suitable location, FIGS. 7-8 show that, in some embodiments, the shroud 106 defines one or more apertures 226 and/or openings 228 around the jets 108 (e.g., at a top side, back side, right side, left side, upper portion, lower portion, and/or at any other suitable portion of the shroud) that are configured to allow a desired amount of air to flow into the shroud 106 while allowing the shroud to form a seal (or partial seal) with a flooring surface (not shown). Indeed, as shown in FIGS. 7-8, in some embodiments, the air inlets or apertures 226 are disposed between the jets 108 at an upper back side of the shroud.

As an additional example of a suitable characteristic, in addition to, or in place of, the lip 116, any other suitable portion of the wand head 104 and/or the shroud 106 (e.g., a portion that is configured to contact a flooring surface when the head is in use and/or any other suitable portion of the wand head, such as the breaker bar 112) may be rounded. While such rounding can perform any suitable function, in some embodiments, such rounding helps reduce friction between the wand head and a flooring surface.

In addition to the aforementioned characteristics, the described wand 100 can have any other suitable characteristic that allows it to operate as intended. Indeed, in some embodiments, the vacuum tube 102 is (as described here) ergonomically shaped to be more comfortable and easy to use than some conventional cleaning attachments.

Additionally, in some embodiments, the described head is configured to deliver a high-pressure controlled spray that loosens dirt and allows the dirt to be removed through a relatively powerful extraction wand. Moreover, in some embodiments, the described wand is configured to prevent flooring surfaces from being flooded with excess fluid. As a result, some embodiments of the described wand are configured to leave flooring surfaces cleaner (e.g., by removing more water, soap, detergent, debris, etc.) than some conventional cleaning devices. Furthermore, as some embodiments of the described wand leave less fluid in flooring than do some conventional devices; such embodiments are able to allow flooring to dry faster than do some conventional devices.

Additionally, in some embodiments, the wand 100 (and/or any other suitable portion of the system 10) comprises or is otherwise associated with one or more sonic valves. While such valves can function in any suitable manner, in some embodiments, they are configured to stop and allow fluid flow in such a manner so as to cause mechanical abrasion as fluid is sprayed through the wand (e.g., the jets) to further loosen dirt and debris in the surface being cleaned.

As another example of a suitable modification, in some embodiments, the wand comprise one or more brushes, agitators, carpet beaters, and/or other objects that are configured to manipulate the flooring surface and to help remove debris therefrom. Indeed, in some embodiments, the roller comprises one or more processes, members, brushes, and/or other objects that extend from the roller and the roller is powered (e.g., via a vacuum powered mechanism, motor, and/or any other suitable mechanism) to rotate.

As another example of a suitable modification, some embodiments of the wand 100 comprise one or more vibrating mechanisms that are configured to vibrate the wand head 104 (e.g., to help agitate the surface being cleaned). In this regard, such a vibrating mechanism can include any suitable vibrating mechanism, including, without limitation, one or more offset spinning weights, weights that translate back in forth in any suitable direction, and/or any other suitable vibrating mechanism. In this regard, the vibrating mechanism can cause the wand head to vibrate in any suitable manner, including, without limitation, in a plane that runs substantially parallel to the surface that is being cleaned.

Thus, as discussed herein, the embodiments of the present invention relate to systems and methods for cleaning objects. In particular, the present invention relates to systems and methods for providing a wand that is configured to clean flooring, such as carpets, rugs, tiles, stone, wood, and/or any other flooring surface.

Magnets

In accordance with some embodiments, the described systems and methods (e.g., the described system 10, the wand 100, and/or any other component described herein, and/or any other conventional or novel systems and methods) comprise one or more magnets that are configured to improve the effectiveness of the cell 12, electrolyzed alkaline water and/or electrolyzed oxidizing water (e.g., by affecting minerals and/or their charge to help prevent the minerals in the water from plating out and/or precipitating and leaving residue on the electrolytic cell's electrodes 17 and/or ion permeable membrane 18, which can damage the electrodes and membrane and/or reduce their effectiveness; by affecting minerals and/or their charge to help prevent the minerals leaving residue on the surface being cleaned; by improving the ability of water to penetrate cleaning surfaces and/or to dissolve dirt and/or other debris; and/or otherwise improving the effectiveness of the system).

In this regard, the system 10 (and/or any other suitable system or device) can comprise any suitable type of magnet that allows electrolyzed alkaline and/or electrolyzed oxidizing water to pass by, to pass through, and/or to otherwise be in proximity to one or more magnets. In this regard, some examples of suitable magnets include, but are not limited to, one or more neodymium magnets; neodymium iron boron magnets; aluminum nickel cobalt alloy magnets; samarium cobalt magnets; electromagnets; ceramic magnets; ferrite magnets; barium ferrite magnets; sintered composite magnets comprising powdered iron oxide and barium or strontium carbonate; magnetite magnets; lodestone magnets; magnets comprising gadolinium and/or dysprosium; iron alloy magnets; steel magnets; rare earth metal magnets; sintered magnets, cast magnets; plastic bonded magnets; isotropic magnets; anisotropic magnets; electronic de-scalers; magnets having a variable magnetic pole; and/or any other suitable type of materials or devices that have (or that are configured to have) magnetic properties. Indeed, in some cases, the described systems and methods comprise one or more rare-earth magnets.

Where the described system 10 (or any other electrolytic and/or cleaning system) comprises one or more magnets, the magnets can be used in any suitable location that allows them to improve: cell 12 operation and/or the shelf life, the cleaning properties, the emulsifying properties, the reactivity, the binding properties of, the effectiveness, and/or that are otherwise configured to condition the electrolyzed alkaline water and/or electrolyzed oxidizing water produced by the system (and/or any other suitable electrolytic system or device).

In some embodiments, the described system 10 (and/or any other suitable system that uses electrolyzed water) comprises one or more magnets that are coupled to or that are otherwise associated with one or more: fluid inlets 20 into an electrolytic cell (e.g., the described cell 12 and/or any other suitable cell), compartments of the electrolytic cell (e.g., the anode compartment 52, the cathode compartment 54, the anolyte recirculation tank 64), fluid outlets 36 from the electrolytic cell, hoses 230 to the wand 100 (and/or a sprayer or other cleaning tool) and/or storage tank 40, the filter 122, feedlines 118, wands 100 (and/or any other suitable wand, sprayer, and/or other dispersal device), wand heads 104, storage containers 40, valves 26, pumps 28, filters 122, shrouds 106, jets 108, jet manifolds 109, vacuum ports 110, breaker bars 112, rollers 114, lips 116, and/or any other suitable component of the described system. Indeed, in some embodiments, the described systems comprise one or more magnets disposed in the roller 114. In some other embodiments, one or more magnets are disposed at and/or prior to the cell's fluid inlet (or inlets). In some additional cases, the described system 10 includes multiple magnets that are disposed at different places along (and/or prior to) the inlet line.

In one non-limiting illustration, FIG. 1A shows some embodiments in which the system 10 comprises magnets 232 on the hosing 230 from the storage tank 40 to the wand 100. Thus, some embodiments include a floor cleaning device (e.g., a wand connected to a vacuum 44) that runs electrolyzed alkaline water (and/or electrolyzed oxidizing water) past one or more magnets before the electrolyzed water is applied to flooring, cloth, and/or any other suitable material or object (e.g., for cleaning and/or sanitation purposes).

Where the system 10 (and/or any other cleaning system that uses electrolyzed alkaline and/or oxidizing water) comprises one or more magnets 232 that are configured to condition the electrolyzed alkaline (and/or oxidizing) water, the magnets can be coupled to the system (or any portion thereof) in any suitable manner. In some embodiments, the magnets are: clamped, glued, adhered, integrally formed with or otherwise connected to, set in pockets of, belted to, tied to, impregnated into, extends around, disposed near, and/or are otherwise coupled to the system.

Figure 11A:
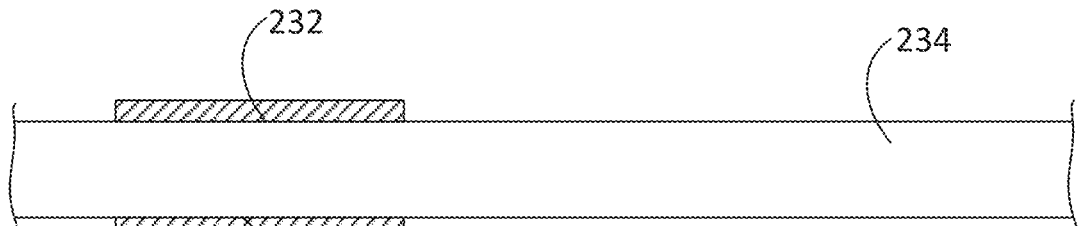
FIGS. 11A-11E each illustrate a section of hosing associated with one or more magnets for conditioning electrolyzed water.
Figure 11B:
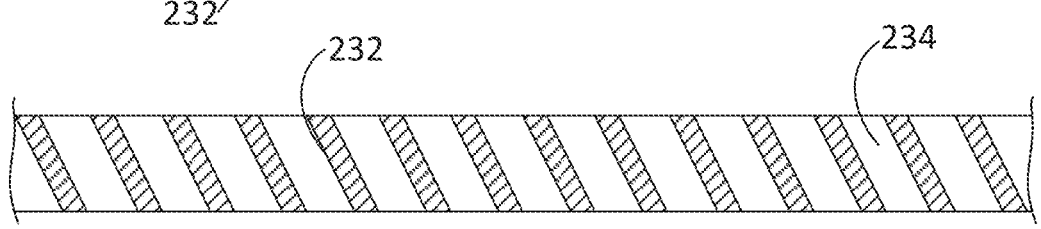
Figure 11C:
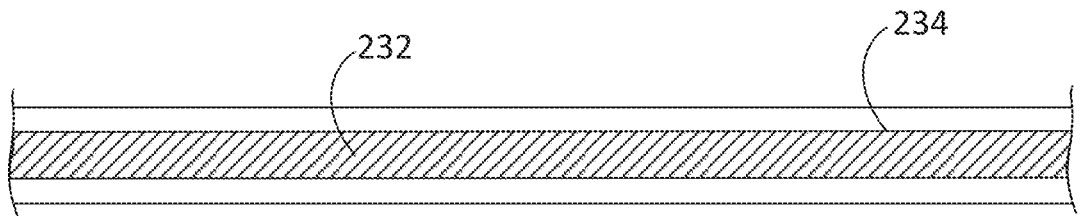
Figure 11D:
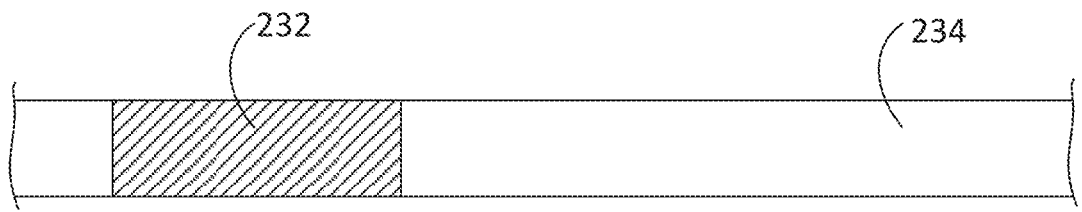
Figure 11E:
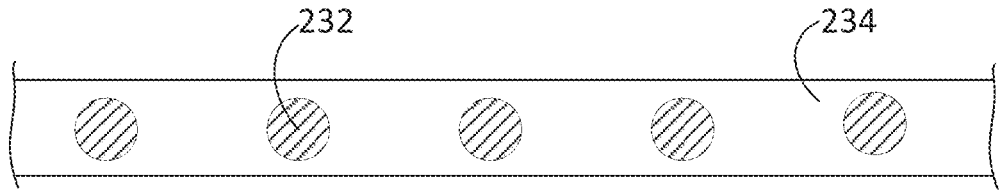

By way of non-limiting example, FIG. 11A shows an embodiment in which two magnets 232 are placed on an outer surface of a tube 234 (e.g., a tube that provides fluid from the container 40 to the cleaning wand 100). FIG. 11B shows an embodiment in which a magnet 232 is wrapped around and/or impregnated into tubing 234 (e.g., a feedline 118, a fluid outlet 36 of the cell 12, and/or at any other suitable portion of the system 10). FIG. 11C illustrates an embodiment in which the magnet 232 runs along at least a length of tube 234 in the system 10. FIG. 11D shows an embodiment in which the magnet 232 is impregnated in a tube 234 of the system 10. Additionally, FIG. 11E shows an embodiment in which one or more magnets 232 are disposed at various places along a length of the tube 234.

Where one or more magnets 232 are used to condition the alkaline and/or oxidizing water, the magnets can have any suitable characteristic that allows them to improve the cleaning power, the shelf life, and/or to otherwise condition the alkaline and/or oxidizing water. Indeed, in some cases, the magnets have a strength between about 0.1 and about 10,000 gaussmeters (or any subrange thereof). Indeed, in some embodiments, the magnets each have a strength of between about 1 and about 300 guassmeters.

The magnets 232 can also be any suitable size (e.g., length, width, thickness, and/or diameter), including, without limitation, having one or more such measurements that are between about 0.001 cm and about 1 m (or any subrange thereof). Indeed, in some implementations, the magnets are between about 4 cm and about 40 cm (or any subrange thereof) in diameter and between about 2 mm and about 10 cm thick.

Thus some embodiments of the present invention relate to improving the properties of electrolyzed alkaline and/or oxidizing water by running such water past one or more magnets.

Electrolyzed Water Conditioning

In accordance with some embodiments, the described systems and methods (and/or any other suitable system and/or methods) are configured to allow one or more fluids (e.g., electrolyzed alkaline water and/or electrolyzed oxidizing water) to flow past each other (and/or themselves) to improve the shelf life, cleaning effectiveness, binding strength, chemical reactivity, the emulsifying characteristics, and/or any other suitable characteristic of the electrolyzed alkaline water and/or electrolyzed oxidizing water. Indeed, in some embodiments, the described systems and methods are configured to modify the surface tension of the electrolyzed water that is produced to help such water better break down, emulsify, capture, dissolve, and/or otherwise treat oil, dirt, and/or other debris in flooring (and/or any other suitable material).

Figure 12A:
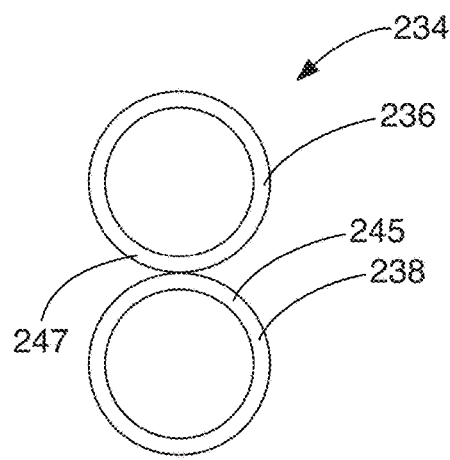
Figure 12B:
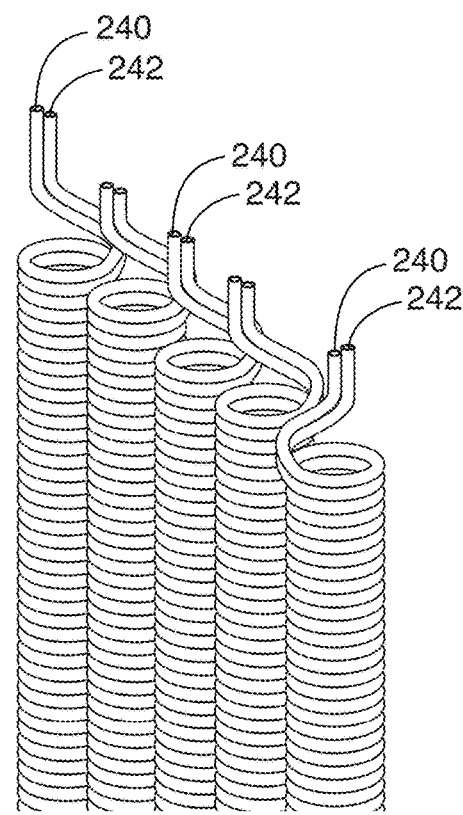
Figure 12C:
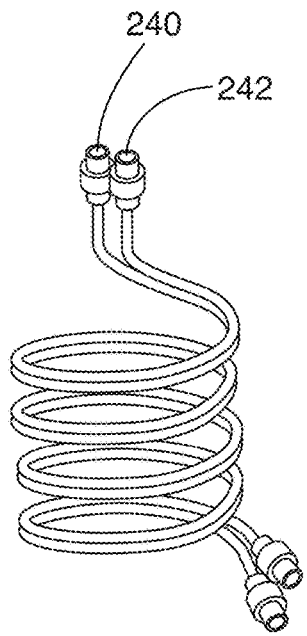
Figure 12D:
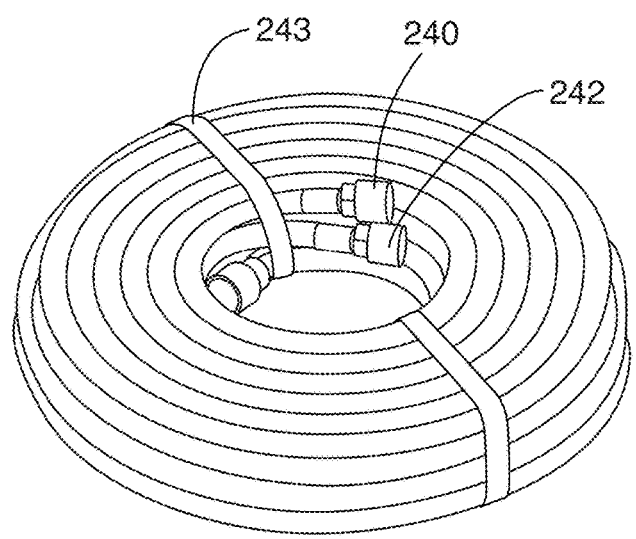
Figure 12I:
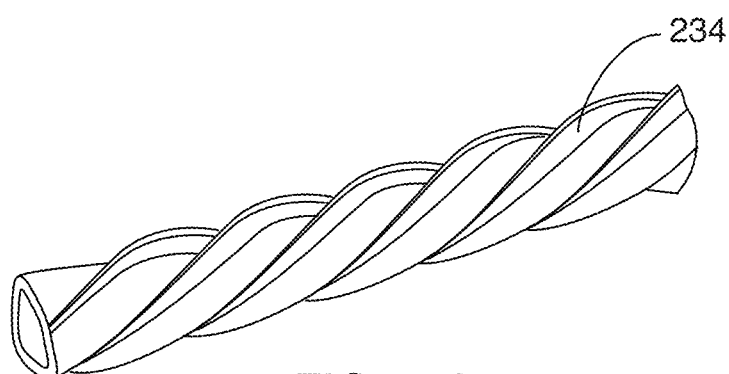
FIG. 12I illustrates a section of conduit having an internal surface that is configured to cause mixing and/or a vortex in fluids that flow through it in accordance with some embodiments.
Figure 12J:
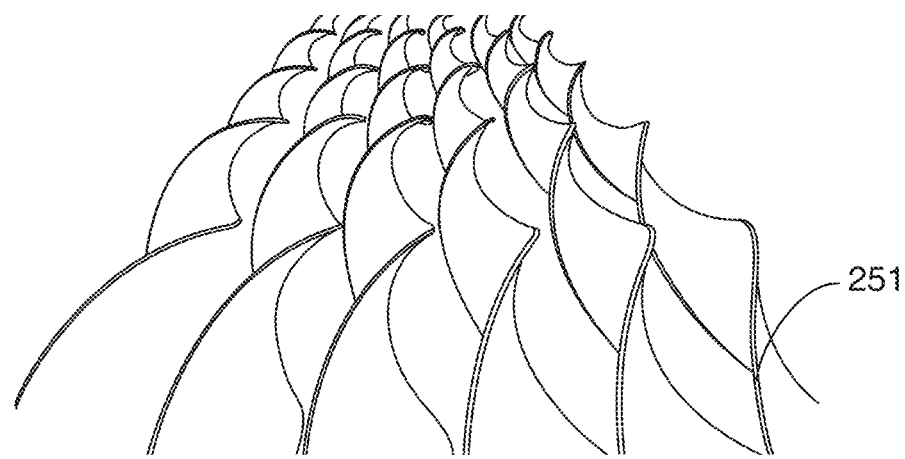
FIGS. 12J-12K show that in some embodiments, an insert can be placed in tubing to help condition fluids that flow through the tubing.
Figure 12K:
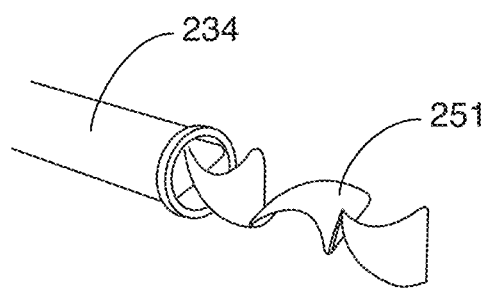
Figure 12L:
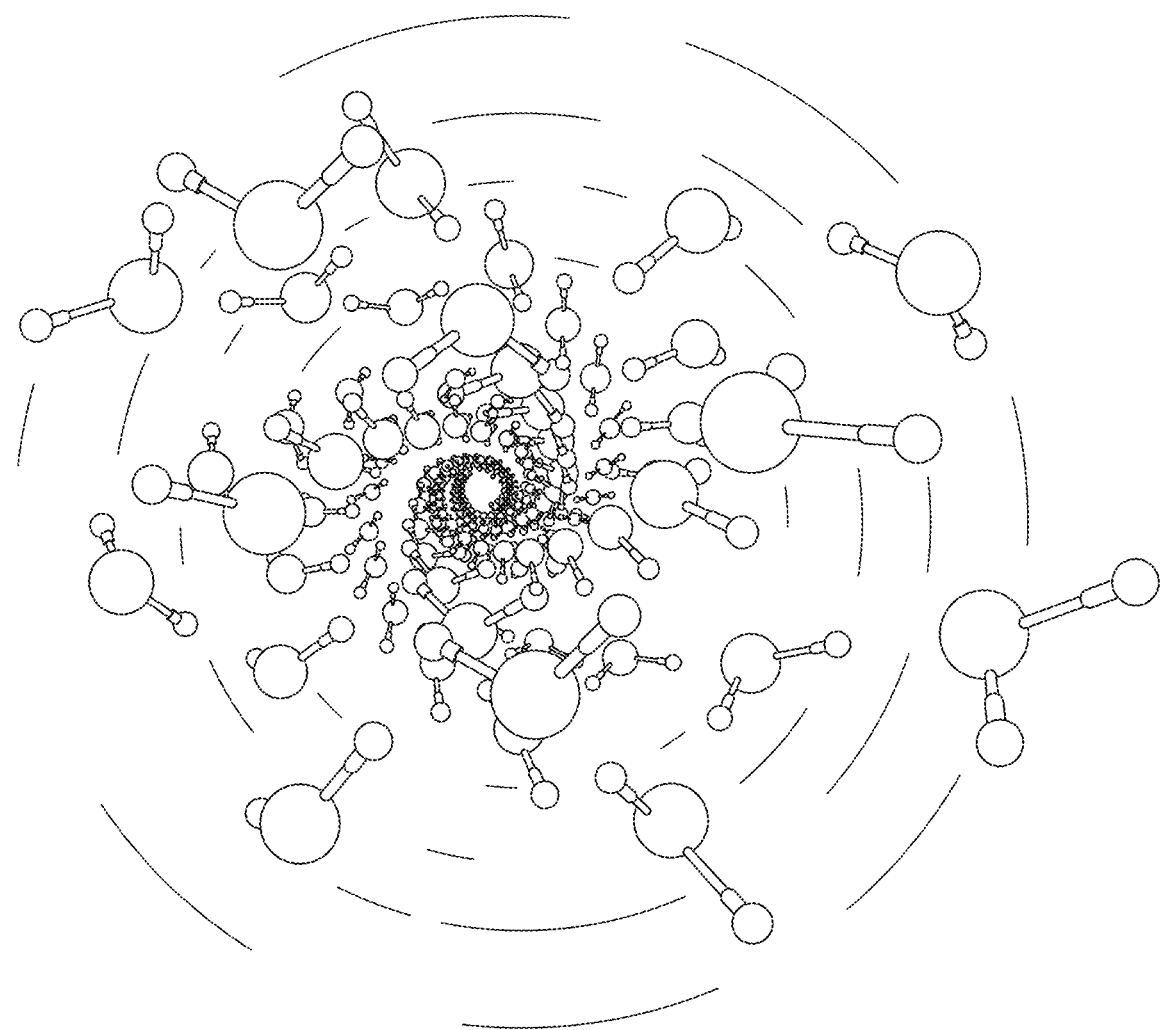
FIG. 12L illustrates a molecular water vortex in accordance with some embodiments.
Figure 12M:
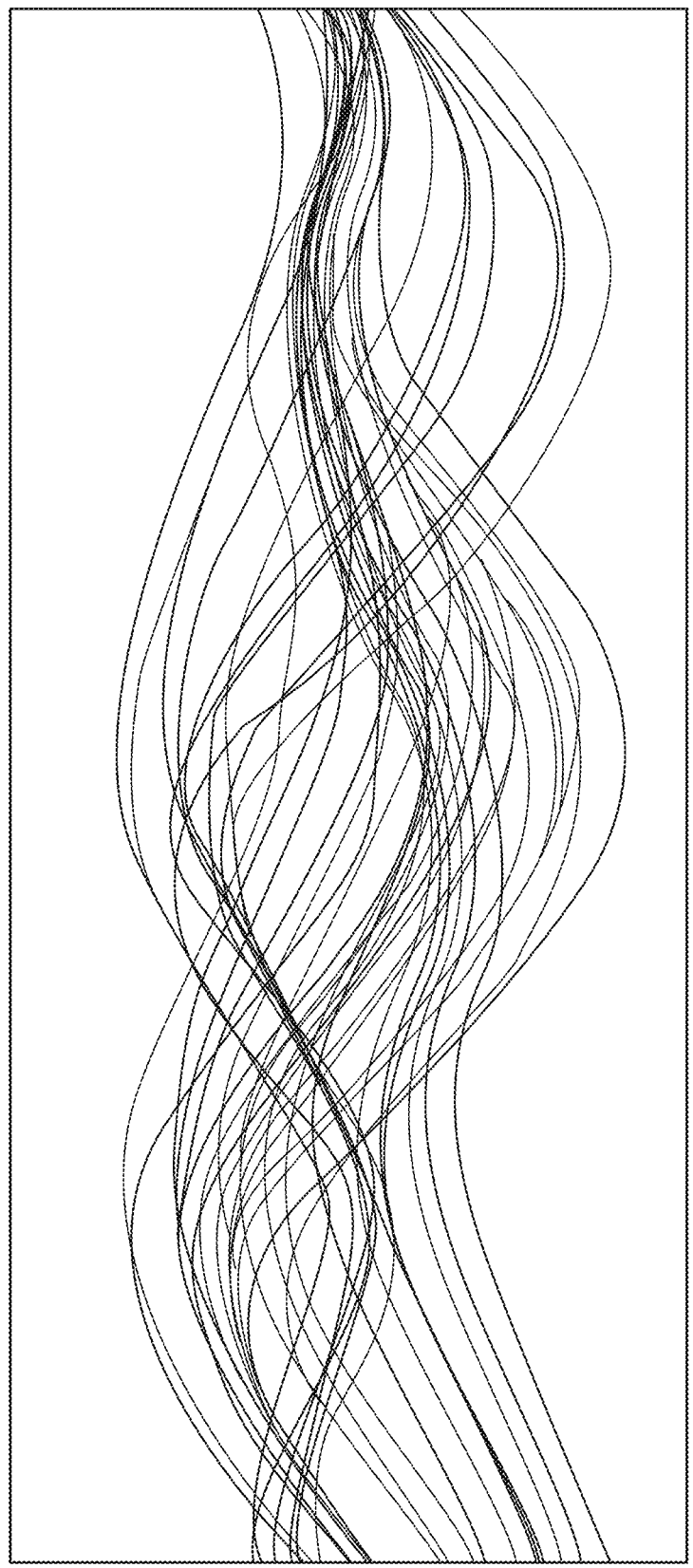
FIG. 12M illustrates a somewhat helical flow that can be achieved in accordance with some embodiments.

In accordance with some embodiments, it is desirable to condition fluid by changing the flow (e.g., prior to the cell 12, within the recirculation line 31, from the cell, from the container 40, and/or any other suitable portion of the system) of the fluid (e.g., electrolyzed alkaline and/or oxidizing water) from a laminar and/or turbulent flow into a vortex flow. In this regard, this vortex flow can be obtained in any suitable manner, including, without limitation, with or without using one or more obstacles, baffles, and/or other physical impediments to flow. Indeed, in some embodiments, such a vortex flow is achieved without one or more obstacles, baffles, or physical impediments. As a result, in some such embodiments, as fluids obtain a vortex flow, the resultant flow has a relatively low amount of friction and a relatively high mixing capability. In some cases, such a flow can also help water molecules form hexamer nano-structured water (or nano clusters, e.g., as shown in FIG. 12S). As a result, in some cases, such fluids with the vortex flow can impart disjoining pressure capability to ordinary water or brine without the addition of particles, micelles, surfactants, and/or other stimulation additives.

Where one or more fluids (e.g., electrolyzed waters) flow past each other and/or themselves (e.g., in the described system 10, in a conventional or novel electrolytic system, in a floor cleaning system, and/or in any other suitable location), the fluids can flow past each other (and/or themselves) in any suitable manner, including, without limitation, by flowing through tubing and/or any other suitable conduit and/or conduits that: are twisted, are wrapped in a helix, are wrapped in a double helix, are wrapped in a triple helix, are coiled upon themselves, are twisted up, include multiple channels, includes where a portion of a fluid is separated from another portion of the fluid by a single wall or membrane of the conduit, comprises internal features that cause the fluids to swirl and/or mix, comprises one or more inserts, and/or by otherwise running one portion of a conduit in proximity to another portion of the conduit (and/or another conduit) that comprises a fluid (e.g., either the same fluid or a different fluid). Similarly, where fluids are forced through tubing to gain a vortex flow, such a flow can be achieved in any suitable manner, including, without limitation, via any of the methods discussed in this paragraph (even if such twisting, coiling, etc. does not cause two or more tubes or portions of the tubes to be in proximity to each other).

In some embodiments, the electrolyzed water (e.g., alkaline water and/or oxidizing water) is conditioned by running the water through a single conduit that is coiled on itself, twisted up, cork screwed, shaped as a helix, and/or that otherwise allow the electrolyzed water to flow past itself (and/or to gain vortex flow). By way of non-limiting illustration, FIG. 12A shows a cross-sectional view of a single tube 234 having a first portion 236 that runs along a second portion 238 (e.g., by being coiled, twisted, and/or otherwise being shaped in such a manner).

In some embodiments, the electrolyzed water (e.g., electrolyzed alkaline water and/or oxidizing water) is configured to be conditioned (e.g., to gain vortex flow) by running the water through a length of two or more conduits that are in close proximity to each other. By way of non-limiting illustration, FIGS. 12B-12D show some embodiments in which a first tube 240 carrying fluid (e.g., alkaline water) runs in proximity to a second tube 242 carrying fluid (e.g., the same fluid as is found in the first tube or, in accordance with some other embodiments, a different fluid).

Figure 12N:
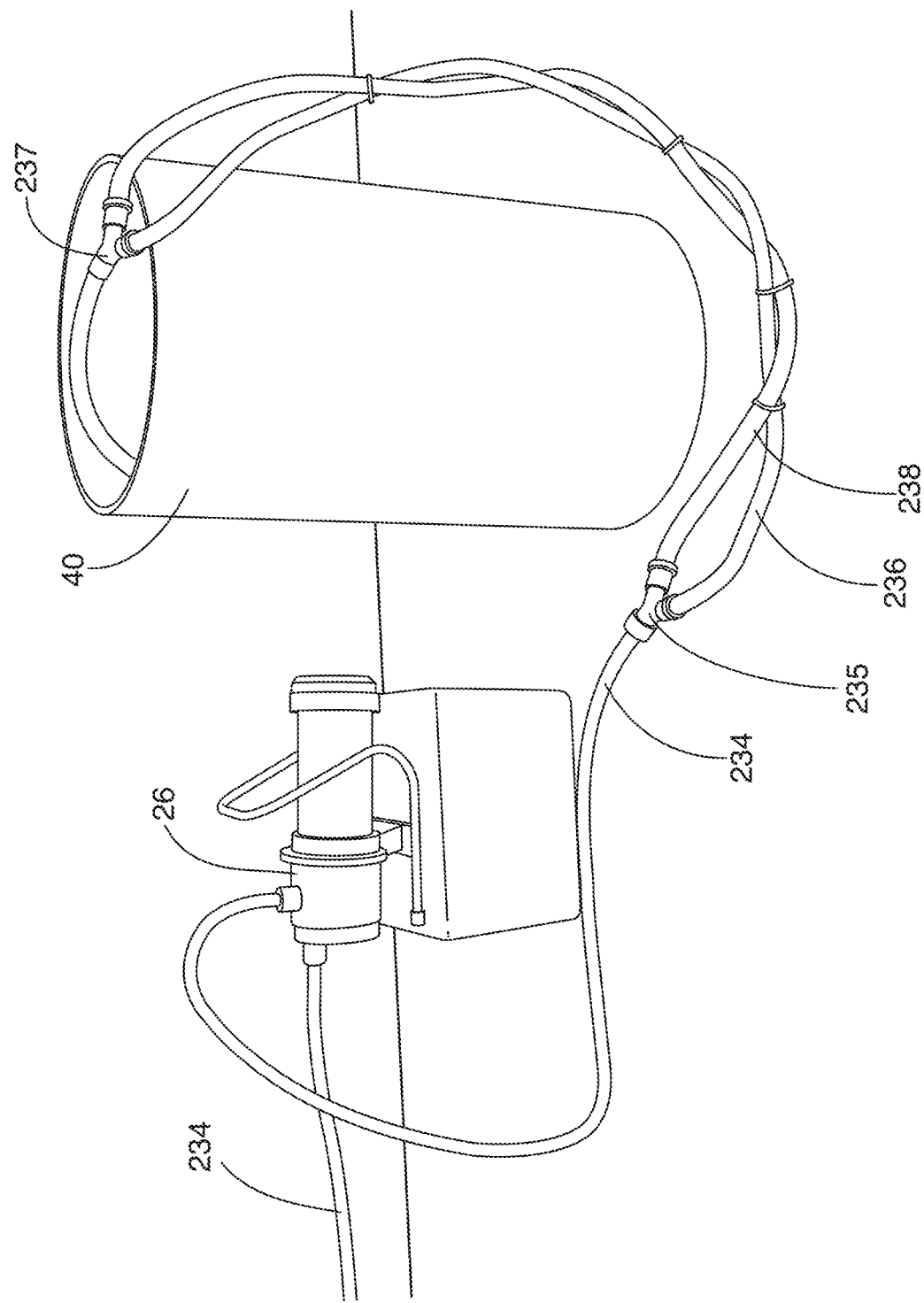
FIG. 12N illustrates some embodiments of a system for conditioning electrolyzed water.

In some embodiments, the described systems and methods include conditioning electrolyzed water (e.g., electrolyzed alkaline water, electrolyzed oxidizing water, and/or mixtures thereof) by splitting (e.g., as shown in FIG. 12N) the electrolyzed water solution into two (or any other suitable number of) streams; running a first stream of the electrolyzed water solution through a first conduit; running a second stream of the electrolyzed water solution through a second conduit (wherein a length of the first conduit and a length of the second conduit run in close proximity to each other); optionally mixing the first and second streams of the electrolyzed water together to form a mixture; then applying the mixture (or the various streams separately) to a material that is to be cleaned; and/or vacuuming up the mixture and debris from the material that is being cleaned. In some such implementations, the first and second conduits are twisted together. Additionally, although in some embodiments, the streams are separated and/or combined only once (e.g., as shown with the splitter 237 and combiner 235 in FIG. 12N), in some other embodiments, the streams are separated and/or combined multiple times (e.g., with any suitable number of splitters and/or combiners).

Where electrolyzed water (e.g., alkaline and/or oxidizing water) is conditioned by running the water through two or more conduits (e.g., tubes 240 and 242), the two or more conduits can be coupled together (or otherwise be held in proximity to each other) in any suitable manner that allows fluid in a first conduit to have an effect on fluid in one or more other conduits (e.g., to have a charge from fluid in one conduit interact with a charge from fluid in one or more other conduits). By way of non-limiting example, the two or more conduits can be coupled together via one or more bands 243 (see e.g., FIG. 12D), straps, ties, cords, ropes, laces, eternal wraps, cases, etc.; by being integrally formed together; by being welded together; by being twisted together; by being coiled together; and/or in any other suitable manner.

While FIG. 12A shows some embodiments in which fluids (not shown) running past each other are separated by two walls of tubing (e.g., walls 245 and 247), in some embodiments, fluids running past each other are separated by a single wall or membrane. As a result, in some such embodiments, charges of the fluids that are running past each other can be easily react and/or affect each other. By way of non-limiting illustration, FIGS. 12E-12H illustrate some embodiments in which a first conduit 244 and a second conduit 246 in a single tube 234 are separated by a single wall or membrane 249.

Where fluid flowing through a first conduit 244 (or portion of a conduit) flows past fluid in a second conduit 246 (and/or a second portion of the conduit (and/or any other suitable number of conduits)) with one or more walls or membranes 249 separating the two flows, the walls or membranes can be any suitable thickness that allow charges from chemicals in a first flow to have any effect on charges from chemicals in the second flow, and vice versa. Indeed, in some embodiments, a distance separating the two flows along a length of the conduits (e.g., the total thickness of the wall, walls, membrane, or membranes separating fluids) is between about 3 µm and about 1 cm (or any subrange thereof). In some cases, however, the distance separating the two flows is between about 12 µm and about 0.33 cm (or simply less than about 0.33 mm).

Where two or more streams of fluid are conditioned by running past each other (e.g., in opposite directions, and/or the same direction, as shown in FIG. 12N), the various streams and/or conduits can be separated from each other by any suitable material. In this regard, some examples of such materials include, one or more types of bi-axially-oriented polyethylene terephthalate, cellophane, polyester, plastic, polyethylene, polyurethane, polyvinyl chloride, polymer, wax paper, rubber, latex, natural material, synthetic material, glass, crystal, metal, and/or any other suitable material that allows the streams to be physically separated while allowing one stream to at least partially condition the other and vice versa. Indeed, in some embodiments, to or more streams or conduits are separated from each other by a polymer membrane.

Although in some embodiments, two tubes 234 (or portions of tubes) having fluids that flow past each other (or themselves) have relatively little contact with each other (see e.g., FIGS. 12A and 12E), in some other embodiments, however, it can be beneficial to have as much surface area contact (or to have a relatively large amount of surface area in proximity to each other) between the two or more tubes (or the two or more portions of the tube). By way of example, FIGS. 12F and 12G show that in some embodiments, a tube 234 is internally split (or two or more tubes are coupled together) to have as much surface area contact between the two or more conduits 244 and 246 as possible. Thus, instead of having two round tubes 234 (or portions of a tube) touch each other at rounded edges, FIGS. 12F and 12G show that, in some embodiments, two or more conduits 244 and 246 contact each other (or are separated from each other) by a relatively flat membrane 249.

Where one or more fluids flow past each other (or themselves) the fluids can flow in any suitable direction with respect to each other. Indeed, in some embodiments, fluids flow past each other (and/or themselves) in the same direction (see e.g., FIG. 12N). In some other embodiments, fluids are configured to flow past each other (and/or themselves) in different directions (see e.g., FIG. 12H). In still some other embodiments, fluids are configured to flow past each other and/or themselves in the same direction at one or more lengths and to then flow past each other and/or themselves in different directions at one or more lengths.

In accordance with some embodiments, two or more different fluids flow past each other to condition one or more of the fluids. Indeed, in some embodiments, an amount of electrolyzed alkaline water, electrolyzed oxidizing water, stabilized alkaline water, stabilized oxidizing water, or any other suitable fluid flow past each other. In some embodiments, alkaline water flows past oxidizing water (e.g., in the same and/or in different directions). In some other embodiments, one type of fluid flows past the same type of fluid (e.g., alkaline water flows past alkaline water and/or oxidizing water flows past oxidizing water). By way of non-limiting illustration, FIG. 12N shows an embodiment in which a single tube 234 is split into two tubes 236 and 238 that are twisted together and through which a single fluid (e.g., electrolyzed alkaline water from the system 10 and/or any other suitable electrolytic setup) flows.

In addition to and/or in place of having one or more fluids flow past each other and/or themselves (and/or to obtain vortex flow), some embodiments of the described systems and methods are configured to have fluids twist, mix, vortex, pass through one or more venturis, pass through one or more screens, pass through one or more orifices, and/or otherwise obtain a desired flow as they pass through tubing 234 and/or other conduits (e.g., the inlet line 118, the outlets 36, etc.). By way of non-limiting illustration, FIG. 12I shows an embodiment in which a section of tubing has internal surfaces and/or features that are configured to cause fluids flowing through it to swirl, vortex, and/or otherwise obtain a desired flow. Similarly, FIGS. 12J-12K show that, in some embodiments, an insert 251 that is configured to cause fluids to swirl, vortex, twist, and/or otherwise obtain a desired flow is inserted into one or more tubes 234 to help condition fluid that flows through the tubes. In this regard, such an insert can be used where a tube is not in proximity to another tube (and/or portion of the tube) or when the tube is in proximity to another tube (and/or another portion of the tube). In any case, FIGS. 12L and 12N illustrate some possible fluid flow patterns to help condition such fluids in accordance with some embodiments.

Where two or more conduits are twisted together (e.g., as shown in FIG. 12N), the conduits can be twisted, 1, 2, 3, 4, 5, 6, 7, 8, 9, 10, or more times (i.e., many more times). Indeed, in some embodiments, it is beneficial to twist the conduits together multiple times. By way of non-limiting illustration, FIG. 12N shows that in some embodiments, the two conduits 236 and 238 are twisted around each other at least two times.

Where two or more conduits are twisted together, the conduits can be twisted together over any suitable length of the conduits, including, without limitation, between about 0.1 m and about 100 meters (or within any subrange thereof). Indeed, in some embodiments, two or more conduits are twisted together (e.g., as shown in FIG. 12N) over a length that is greater than 1 m (e.g., between about 1 m and about 10 m).

In some cases, fluid conditioning includes passing fluid through coiled, helix shaped, overlapping, twisted conduits, and/or other suitable tubing one time. In some other embodiments, however, fluids are recycled through such tubing (or conduits) 2, 3, 4, 5, 6, 7, 8 or more times before they are used.

Where the described systems and methods (and/or any other suitable system and/or methods) are configured to allow one or more fluids (e.g., electrolyzed alkaline water and/or electrolyzed oxidizing water) to flow past each other (and/or themselves) (and/or to obtain vortex flow), the overlapping tubing (and/or twisted or otherwise specially shaped tubing) can be disposed in any suitable location. Indeed, in some cases, the overlapping tubing (e.g., the double helix tubing, the coiled tubing having a single membrane separating portions of the tubing to allow fluids to flow past themselves, etc.) and/or the twisted tubing is disposed prior to and/or in association with one or more: fluid inlets into an electrolytic cell (e.g., the described cell 12 and/or any other suitable cell), compartments of the electrolytic cell (e.g., the anode compartment 52, the cathode compartment 54, the anolyte recirculation tank 64, and/or any other suitable portion of the cell), fluid outlets 36 from the electrolytic cell, hoses 230 to the wand 100 (and/or a sprayer or other cleaning tool) and/or the storage tank 40, the wand (and/or any other suitable wand), the wand head 104, the storage tank 40, and/or any other suitable component of the described system. Indeed, in some embodiments, the overlapping tubing (and/or tubing that comprises one or more internal features and/or inserts) is disposed between the wand head and the storage tank and/or electrolytic cell.

The following examples are given to illustrate some embodiments within the scope of the present disclosure. These are given by way of example only, and it is understood that the following examples are not comprehensive or exhaustive of the many types of embodiments of the present invention in accordance with the present invention.

EXAMPLES

Figure 12O:
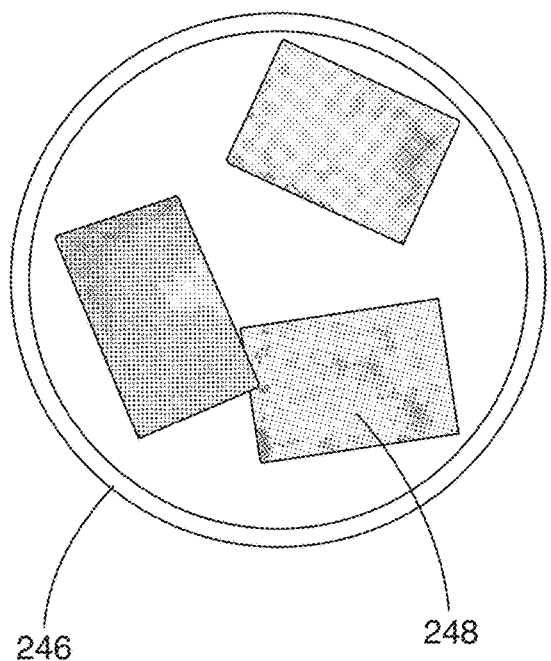
FIGS. 12O-12P depict some experimental results showing some differences in effect between standard electrolyzed water and conditioned electrolyzed water.
Figure 12P:
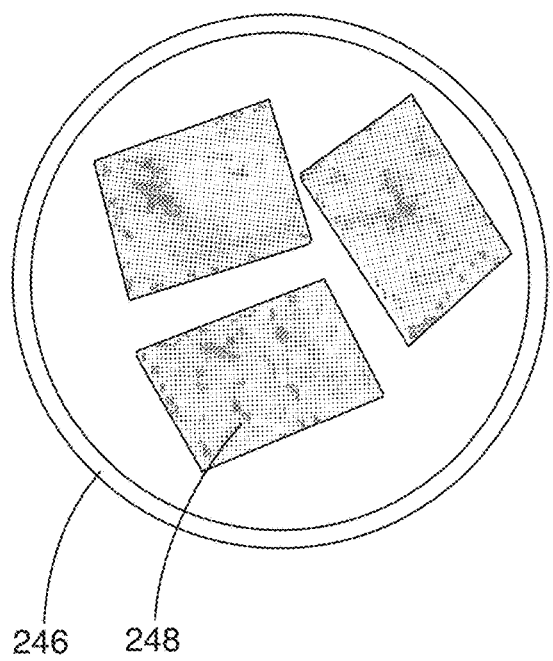
Figure 12Q:
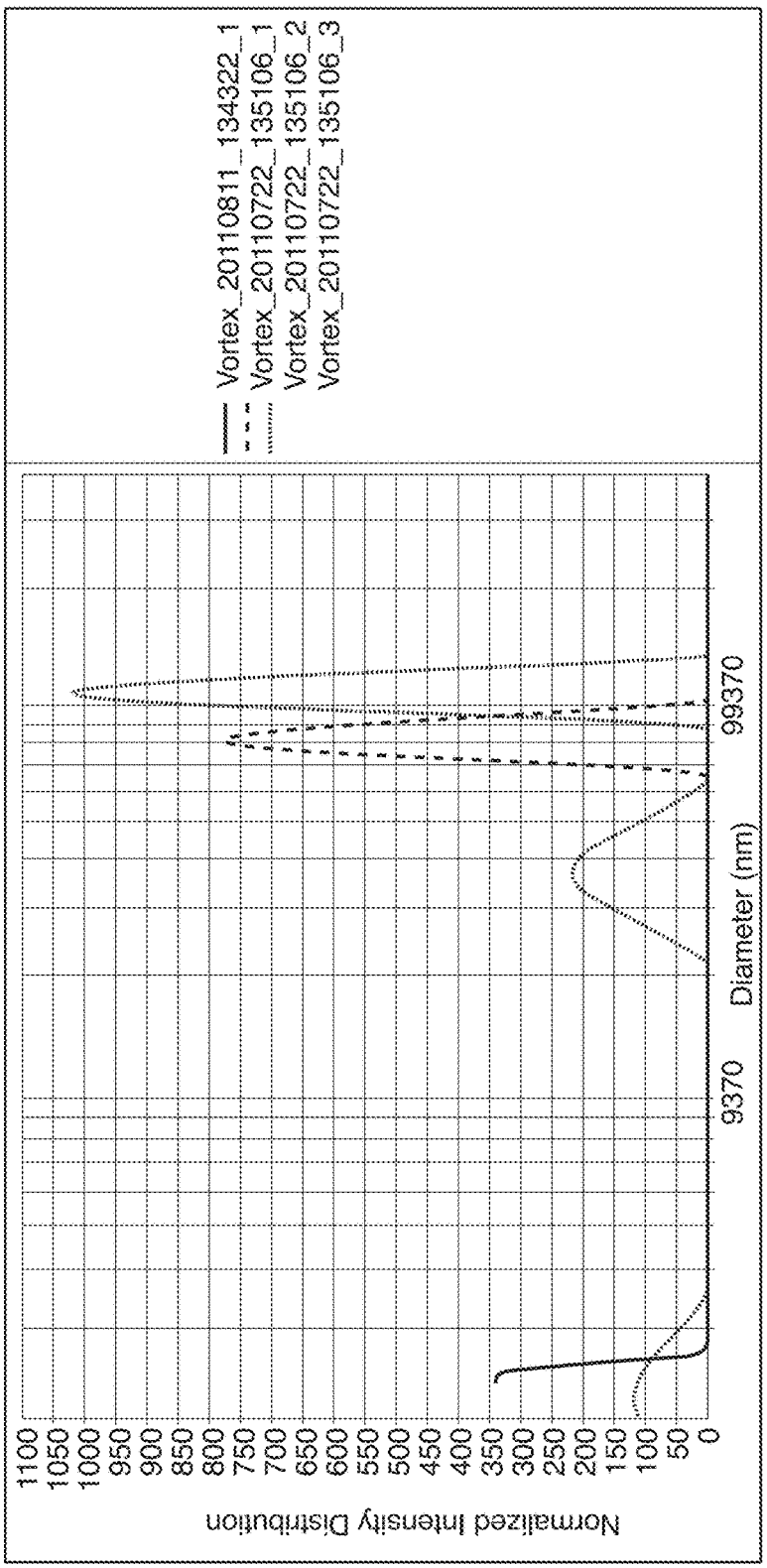
Figure 12S:
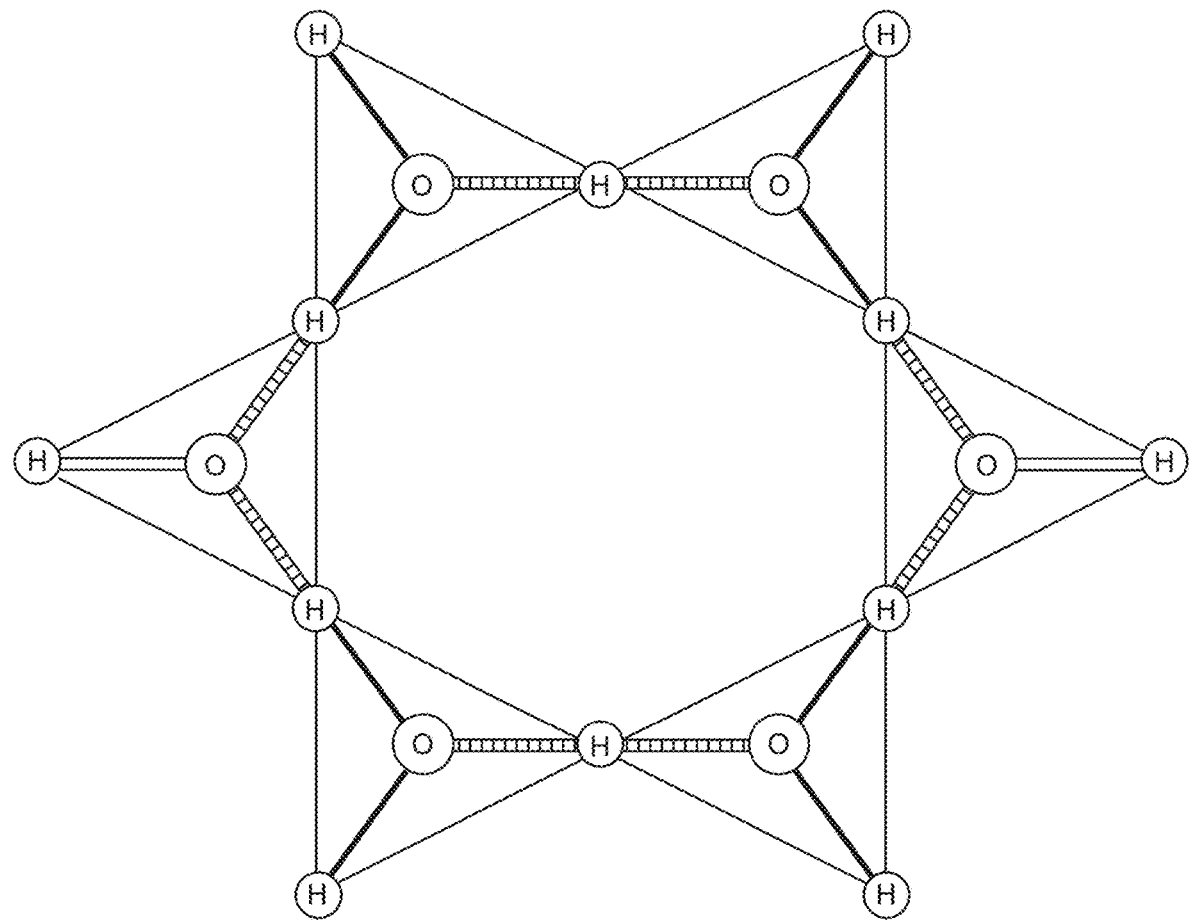
FIG. 12S depicts some embodiments of a water nano cluster.

In one example of conditioning fluid, two samples of electrolyzed alkaline water were prepared (e.g., using the system 10). While the alkaline water in the petri dish 246 of FIG. 12O was otherwise untreated, the alkaline water in the petri dish 246 of FIG. 12P was conditioned by being run through the hoses 236 and 238 of FIG. 12N one time. The two different fluids were then placed in the petri dishes along with three hydrocarbon stained substrates 248. After twenty hours of sitting in their respective solutions, the hydrocarbon stained substrates 248 had varying appearances. In particular, hydrocarbons in the substrates 248 of FIG. 12P had congregated into more concentrated locations (e.g., resembling micelles). As a result, it is apparent that alkaline water treated in the double helix system of FIG. 12N can be better at capturing oils (e.g., for pulling then from carpets and/or other materials). Moreover, additional test results of conditioned alkaline water are set forth in FIGS. 12Q-12R.

Thus, some embodiments of the described systems and methods relate to conditioning of electrolyzed alkaline and/or oxidizing water. In particular, some of the described systems and methods are configured to give fluids a vortex flow (e.g., to create nano-clusters) and/or to have fluids flow past in proximity to other fluids and/or themselves.

Cleaning Agent

In accordance with some embodiments, the described systems and methods relate to one or more cleaning agents that are configured to help improve cleaning processes (e.g., for cleaning flooring, and/or any other suitable object, material, and/or surface). While the cleaning agent can comprise any suitable ingredient, in some cases, it includes sodium carbonate, sodium percarbonate, orange oil, orange peel terpene, water, alkaline water, oxidizing water, citrus terpene, one or more soy proteins, EXCEL™ soy products, limonene, D-limonene, one or more essential oils, and/or one or more: natural oil extracts (including, without limitation, lemon oil, tea tree oil, rosemary oil, lavender oil, eucalyptus oil, peppermint oil, cinnamon leaf oil, pine oil, thyme oil, and/or any other suitable natural oil extract), any suitable petroleum additives, any suitable bio organic materials, enzymes (including, without limitation, one or more cellulases, pepsins, proteases, amylases, lipase, mannanases, pectinases, and/or any other suitable enzyme), any suitable synthetic cleaning materials, vinegar, peroxide, trichloroethane, trichloroethylene, mineral spirits, Stoddard solvent, petroleum naptha, benzene, xylene, dish soap, soap, detergent, dipolylene glycol n-butyl ether, lauramine oxide, sodium lauryl sulfate, sodium laurethsulfate, c12-14-16 dimethyl amine oxide, alcohol, fragrance, and/or any other suitable ingredient. Indeed, in some embodiments, the cleaning agent comprises water, sodium carbonate, sodium percarbonate, and/or a citrus terpene.

The various ingredients in the cleaning agent can be present in the cleaning agent at any suitable concentration that allows the cleaning agent to be used to clean, pre-treat, and/or otherwise help remove stains, residue, and/or debris from any suitable surface or object. Indeed, in some cases, the various active ingredients in the cleaning agent (e.g., sodium carbonate, sodium percarbonate, orange peel terpene, etc.) are each present in the cleaning agent at concentration between about 0.1 and about 99% by molecular weight. In some embodiments, each active ingredients in the cleaning agent is present at between about 0.1% and about 60% by molecular weight (or within any subrange thereof). Indeed, in some implementations, an active ingredient is included in the cleaning agent at a concentration of between about 5% and about 30% by weight (e.g., at a concentration of about 20%±5%).

The cleaning agent can be used in any suitable manner, including, without limitation, by being sprayed on a surface (e.g., as a pre-spray for application of the electrolyzed water, being sprayed with the electrolyzed water, being applied to a surface after application of the electrolyzed water, and/or at any other suitable time), misted on a surface, wiped on a surface, painted on a surface, dusted on a surface (where the ingredients are dried), and/or otherwise applied to a surface or material. Indeed, in some embodiments, the described cleaning agent is applied to a surface (e.g., flooring and/or any other suitable material) as a pre-spray (e.g., via a motorized sprayer, a hand pump sprayer, hose sprayer, tank sprayer, trombone sprayer, aerosol, squeeze sprayer, knap sap sprayer, duster, hydraulic sprayer, manual pneumatic sprayer, motorized pneumatic sprayer, pedal pump sprayer, traction pneumatic sprayer, fogger, mister, broadcast spreader, and/or any other suitable mechanism for applying the cleaning agent to a desired location). In some cases, after the cleaning agent has been applied (e.g., as a pre-spray), electrolyzed water, water, and/or a vacuum is used to rinse and/or otherwise remove the cleaning agent from the material that is being cleaned. Indeed, in some embodiments, electrolyzed alkaline water and a vacuum are used to wash out and remove the pre-spray.

In addition to comprising electrolyzed alkaline water (and/or electrolyzed oxidizing water), the described cleaning agent can comprise any other suitable ingredient that allows it to be used for any suitable purpose (e.g., cleaning, disinfecting, etc.). Some non-limiting examples of such ingredients include one or more diluents, carriers, moisturizing agents, lotions, aloe, fragrances, surfactants (e.g., sodium diamphoacetate, coco phosphatidyl PG-dimonium chloride, and/or any other suitable surfactants), humectants (e.g., propylene glycol, glycerine, and/or any other suitable humectants), and/or any other suitable ingredients. Indeed, in some embodiments, in addition to sodium carbonate, sodium percarbonate, and/or orange peel terpene, the cleaning agent comprises one or more soy proteins.

Thus, in accordance with some embodiments, the described systems and methods relate to a cleaning agent comprising sodium carbonate, sodium percarbonate, and/or one or more citrus terpenes.

Modified Electrolyzed Water

Some embodiments of the described systems and methods relate to the addition of one or more chemicals to the electrolyzed alkaline water, the electrolyzed oxidizing water, and/or mixtures thereof. Indeed, in some cases, a natural agent is added to electrolyzed alkaline and/or electrolyzed oxidizing water to form a modified electrolyzed water (e.g., produced by the system 10 or otherwise). In this regard, some examples of suitable natural agents include, but are not limited to, one or essential oils, plant extracts, sodium carbonate, sodium percarbonate, orange oil, orange peel terpene, water, alkaline water, oxidizing water, citrus terpene, one or more soy proteins, EXCEL™ soy products, limonene, D-limonene, one or more essential oils, and/or one or more: natural oil extracts (including, without limitation, lemon oil, tea tree oil, rosemary oil, lavender oil, eucalyptus oil, peppermint oil, cinnamon leaf oil, pine oil, thyme oil, and/or any other suitable natural oil extract, bio organic materials, enzymes (including, without limitation, one or more cellulases, pepsins, proteases, amylases, lipase, mannanases, pectinases, and/or any other suitable enzyme), vinegar, peroxide, alcohol, and/or any other suitable ingredient.

The various ingredients in the modified electrolyzed water can be present in the electrolyzed water (e.g., alkaline water and/or oxidizing water (and/or stabilized oxidizing and/or stabilized alkaline water)) at any suitable concentration that allows the modified electrolyzed water to be used to clean, pre-treat, emulsify, and/or otherwise help remove stains, residue, and/or debris from any suitable surface or object. Indeed, in some cases, the various active ingredients in the modified electrolyzed water are each present in the modified water at concentration between about 0.1 and about 99% by weight. In some embodiments, each of the active ingredients in the electrolyzed water is present at between about 0.1% and about 60% by molecular weight (or within any subrange thereof). Indeed, in some implementations, an active ingredient is present in the modified electrolyzed water at a concentration of between about 5% and about 30% by weight (e.g., at a concentration of about 20%±5%).

The modified electrolyzed water can be used in any suitable manner, including, without limitation, by being: used with the wand 100, sprayed on a surface, being misted on a surface, wiped on a surface, painted on a surface, and/or otherwise applied to a surface or material. Indeed, in some embodiments, the described modified electrolyzed water is applied to a surface (e.g., flooring and/or any other suitable material) as part of a cleaning procedure (e.g., via the wand 100 and a pump 28). In some such embodiments, the modified electrolyzed water is then removed from the surface via a vacuum and/or in any other suitable manner.

In addition to comprising electrolyzed alkaline water (and/or electrolyzed oxidizing water), the described modified electrolyzed water can comprise any other suitable ingredient that allows it to be used for any suitable purpose (e.g., cleaning, disinfecting, etc.). Some non-limiting examples of such ingredients include one or more diluents, carriers, moisturizing agents, lotions, aloe, fragrances, surfactants (e.g., sodium diamphoacetate, coco phosphatidyl PG-dimonium chloride, and/or any other suitable surfactants), humectants (e.g., propylene glycol, glycerine, and/or any other suitable humectants), and/or any other suitable ingredients.

Thus, in accordance with some embodiments, the described systems and methods relate to modified electrolyzed water (e.g., alkaline water).

Wipes and Cleaning Implements

In accordance with some embodiments, the described systems and methods include one or more disposable and/or reusable cloths, towels, towelettes, rags, swabs, mops, sponges, scrubbers, cotton swabs, brushes, and/or other forms of wipes or cleaning implements that comprise electrolyzed alkaline water, electrolyzed oxidizing water, stabilized oxidizing water, stabilized alkaline water, the described cleaning agent, the described modified electrolyzed water, and/or any other suitable ingredient.

In some embodiments, the described systems and methods include a package of cleaning implements, the package comprising multiple cleaning implements that each comprise an absorptive material; and an electrolyzed water solution, wherein the electrolyzed water solution is disposed within the absorptive material. In some such embodiments, the cleaning implements are selected from wet wipes, sponges, cloths, brushes, towelettes, rags, swabs, mops, micro-fiber materials, sponges, scrubbers, microfiber cloths, scouring pads, cellulose, cellulosic materials, band aids, bandages, pieces of gauze, pieces of steel wool, and combinations thereof.

In some embodiments, such cleaning implement comprises a mop having an absorptive material and a spray device that is configured to spray the electrolyzed water (e.g., on demand and/or in any other suitable manner). In some such embodiments, the electrolyzed water can be replaced, refilled, and/or the mop can be discarded, as appropriate.

In some embodiments, such wipes (or other cleaning implements) comprise cloth, a foldable wipe, and/or any other suitable object that is saturated with and/or that otherwise comprises electrolyzed alkaline water, electrolyzed oxidizing water, and/or any other ingredient discussed in this disclosure. In some embodiments, however, such implements comprise one or more towels, towelettes, rags, cotton balls, swabs, and/or other suitable wipes that include an electrolyzed alkaline water (e.g., produced from the system 10 and/or from any other suitable electrolytic device). As a result, such wipes can be used to clean virtually any suitable surface, object, and/or material. For instance, such wipes can be used to: spot scrub carpets or upholstery, wash walls, wipe clothing, and/or can be used for any other suitable purpose.

Figure 13:
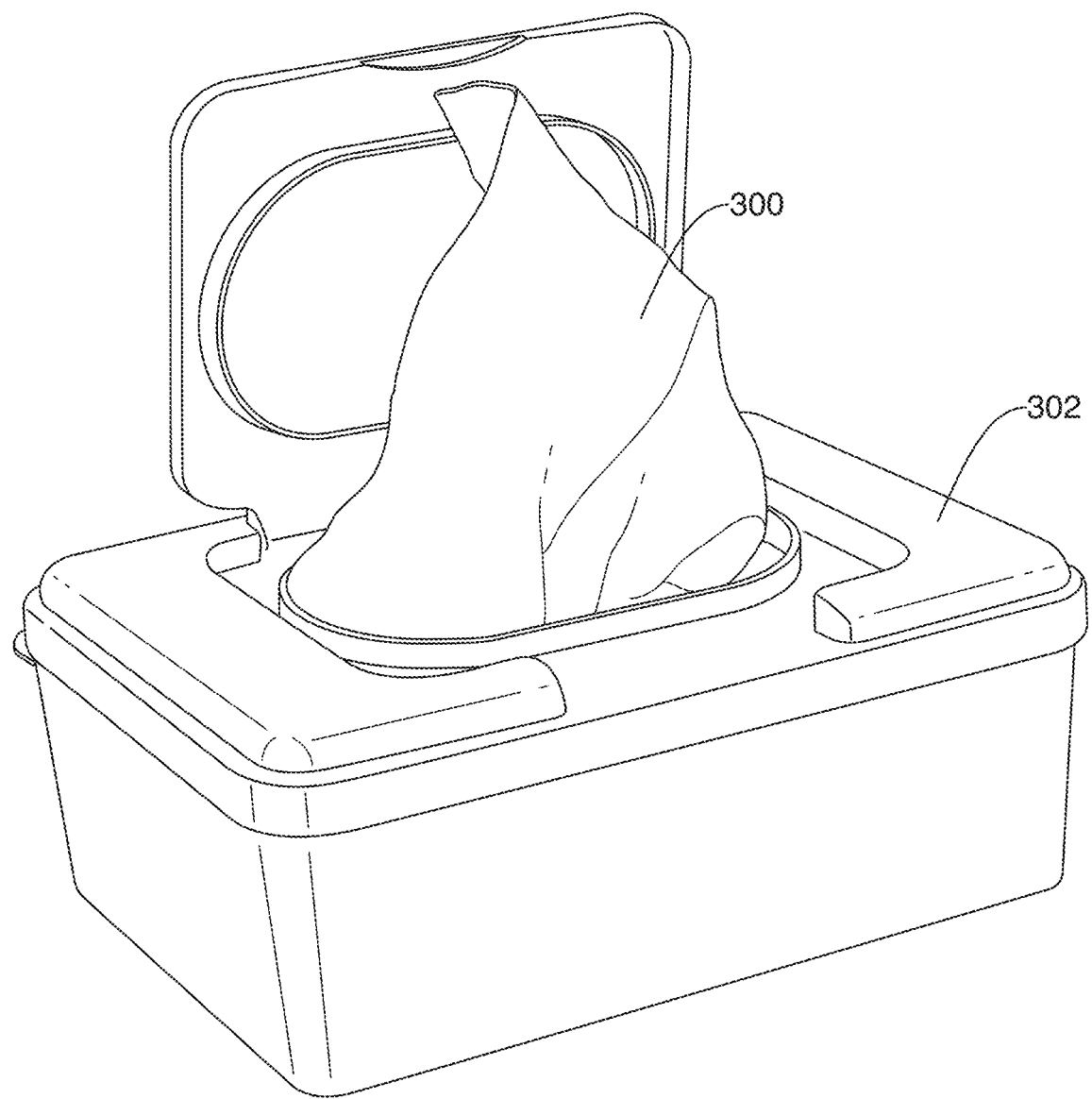
FIG. 13 illustrates a representative embodiment of a cleaning implement comprising electrolyzed water (e.g., electrolyzed alkaline water)

While such wipes can comprise any suitable material, in some embodiments, they comprise silk, cotton, polyester, wool, rayon, cloth, linen, gauze, resin, polyethylene, polypropylene, paper, paper towels, toilet paper, fiberglass, micro-fiber material, textile, foam, sponge, felt, bamboo, wood pulp, cellulose, and/or any other suitable material. By way of non-limiting illustration, FIG. 13 illustrates a representative embodiment of a wipe 300 that comprises electrolyzed alkaline water and that is disposed in a container 302.

The wipes can have any suitable characteristic that allows them to be used to wipe electrolyzed alkaline, electrolyzed oxidizing water, and/or any other suitable ingredient on to a surface or object. In this regard, some embodiments of the wipes comprise one or more woven materials, non-woven materials, embossed materials, single-ply materials, double-ply materials, poly-ply materials, quilted materials, printed materials, hydrophilic materials, air-through materials, and/or other suitable characteristics that allow them to be used to clean surfaces, objects, and/or materials.

Where the wipes 300 comprise electrolyzed alkaline water (and/or electrolyzed oxidizing water), the wipes can comprise any suitable amount of such fluid (and/or fluids). Indeed, in some embodiments, the wipes are saturated with electrolyzed alkaline water (and/or electrolyzed oxidizing water) such that the alkaline water (and/or oxidizing water) comprises between about 0.5% and about 99% (or any subrange thereof) of a wipe's total weight. Indeed, in some embodiments, the alkaline water (and/or oxidizing water) comprise between about 0.005% and about 50% of a wipe's total weight.

Where the wipes comprise electrolyzed alkaline water (and/or electrolyzed oxidizing water), the electrolyzed alkaline (and/or electrolyzed oxidizing) water can be produced in any suitable manner, including, without limitation, via the system 10 and/or any other suitable electrolytic cell. Similarly, the electrolyzed alkaline (and/or electrolyzed oxidizing) water can be produced using any suitable electrolyte, including, without limitation, one or more of the electrolytes discussed above. Thus, while the electrolyzed alkaline (and/or oxidizing) water in the wipes can have any suitable characteristic (e.g., pH, salt content, lack of salt content, and/or other characteristic), in some embodiments, the electrolyzed alkaline water (and/or the oxidizing water, the cleaning agent, the modified electrolyzed water, and/or any other suitable ingredient) in the wipes has the same characteristics of the electrolyzed alkaline water (and/or the oxidizing water, the cleaning agent, the modified electrolyzed water, and/or any other suitable ingredient) discussed herein (e.g., produced by the system 10 and/or otherwise). By way of non-limiting example, in some cases, the wipes comprise electrolyzed alkaline water that was produced with the system 10 (or any other suitable device), using sodium carbonate as the electrolyte, such that the alkaline water has a pH between about 7.5 and about 13.5.

In addition to comprising electrolyzed alkaline water (and/or the oxidizing water, the cleaning agent, the modified electrolyzed water, and/or any other suitable ingredient), the described wipes (and/or other cleaning implements) can comprise any other suitable ingredient that allows them to be used for any suitable purpose (e.g., cleaning, disinfecting, etc.). Some non-limiting examples of such ingredients include one or more diluents, carriers, moisturizing agents, lotions, aloe, fragrances, surfactants (e.g., sodium diamphoacetate, coco phosphatidyl PG-dimonium chloride, and/or any other suitable surfactants), humectants (e.g., propylene glycol, glycerine, and/or any other suitable humectants that are capable of helping to prevent the wipes from drying out too quickly), and/or any other suitable ingredient.

Thus, in accordance with some embodiments, the described systems and methods relate to one or more disposable and/or reusable cloths, towels, towelettes, rags, swabs, mops, microfiber materials, sponges, scrubbers, cotton swabs, brushes, and/or other forms of wipes or cleaning implements that comprise electrolyzed alkaline water, electrolyzed oxidizing water, stabilized oxidizing water, stabilized alkaline water, the described cleaning agent, the described modified electrolyzed water, and/or any other suitable ingredient.

Counter Rotating Device

Some embodiments of the described systems and methods further relate to an agitator comprising a motor (and/or other power device) and 2, 3, 4, 5, 6, 6, 7, 8, 9, 10, or more rug beaters, brushes, and/or other agitation devices that are configured to pull and/or otherwise collect hair, fur, dust, mites, dirt, and/or other debris from surfaces being cleaned. Indeed, in some cases, the agitator comprises at least two brushes having relatively soft and/or stiff bristles, where the two brushes are substantially cylindrically shaped, and are configured to spin (e.g., via the power source) about an axis that runs substantially horizontally to a surface (e.g., flooring surface) being cleaned.

Figure 14A:
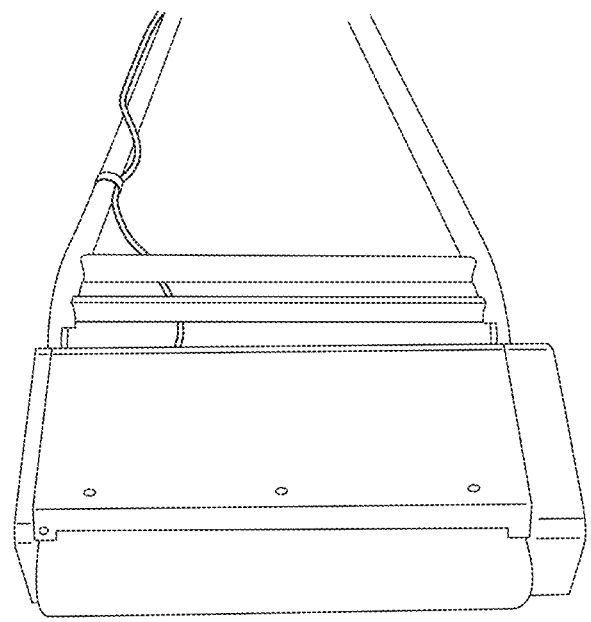
FIG. 14A illustrates a representative embodiment of an agitator.
Figure 14B:
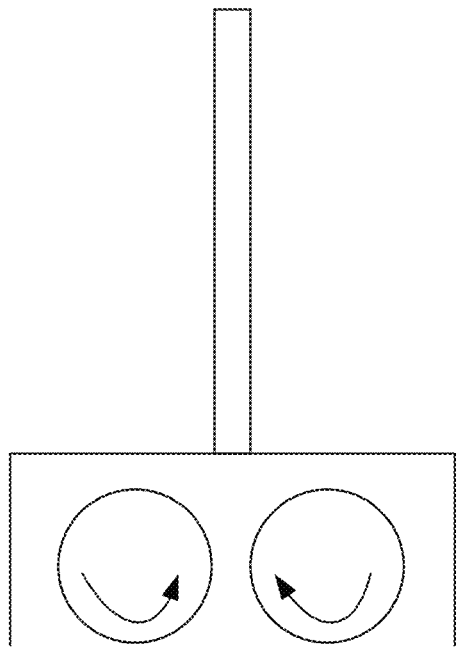
FIGS. 14B-14C each illustrate a schematic side view of the agitator, showing different embodiments in which brushes in the agitator counter rotate in different directions.
Figure 14C:
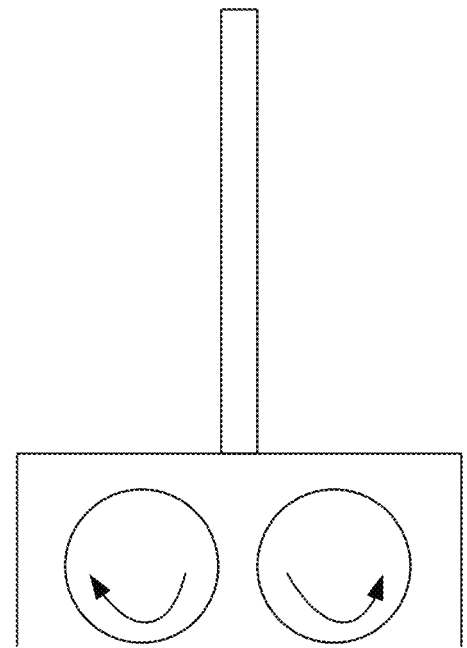

In some such embodiments, at least two of the brushes counter rotate. By way of illustration, FIGS. 14A-14B show that, in some embodiments, while a first brush 308 of the agitator 306 rotates counterclockwise, the second brush 308 moves clockwise. In contrast, FIG. 14C shows that, in some cases, when the first brush 306 moves clockwise, the second brush 308 rotates counterclockwise. In this regard, some embodiments of the described agitator are configured to selectively cause the directions of the brushes to be switched so that the opposing brushes continue to counter rotate with respect to each other. As a result, in some such embodiments, brush life can be extended.

The brushes can rotate at any suitable speed that allows them to function as described herein. Indeed, in some embodiments, the brushes are configured to rotate at between about 10 and about 10,000 rpm (or in any subrange thereof). In some cases, for instance, the brushes each rotate at between about 100 rpm and about 2,000 rpm (e.g., between about 200 rpm and about 800 rpm.

In some cases, the weight of the agitator 306 can help it pull debris from deep in flooring (e.g., carpeting). In this regard, the agitator can weigh any suitable amount, including, without limitation, between about 1 kg and about 1,000 kg (or any subrange thereof). Indeed, in some embodiments, the agitator weighs between about 10 kg and about 30 kg. In fact, in some cases, in order to help the agitator weigh enough to properly remove debris, one or more additional weights are added to the agitator.

Thus, in accordance with some embodiments, the described systems and methods relate to an agitator comprising at least two counter rotating brushes that are configured to pull debris from the surface to which the agitator is applied.

While the disclosure herein is separated into a variety of headings and sections, the various systems and methods from each of the sections and throughout this disclosure (including the figures) can be combined and mixed and matched in any and all suitable manners. Indeed, in some cases, to avoid repetitiveness, various characteristics and combinations of the described systems are not repeated between the various sections.

The various portions of the described systems (e.g., the system 10, the wand 100, the magnets, the tubing, and/or any other element disclosed herein) can be made in any suitable manner. In this regard, some non-limiting examples of methods for making the described wand (e.g., the vacuum tube 102, the wand head 104, and/or other components of the wand) include extruding; molding; machining; bending; straightening; cutting; grinding; filing; smoothing; buffing; polishing; connecting various pieces with one or more mechanical fasteners (e.g., nails, clamps, rivets, staples, clips, pegs, crimps, pins, brads, threads, brackets, quick-connect couplers, nuts, bolts, threaded engagements, screws, etc.); welds; by melting pieces together, adhesives, etc.); and/or any other suitable method that allows the described wand to be formed and perform its intended functions.

Additionally, the various fluids discussed herein can be used in any suitable manner. Indeed, the various fluids can be mixed together in any suitable manner. Moreover, the fluids can be dispersed in any suitable manner, including, without limitation, via one or more manual and/or motorized sprayers, misters, hoses, wands, and/or in any other suitable manner. In some other embodiments, one or more of the fluids discussed herein are injected and/or ingested into a living animal. Indeed, in some embodiments, electrolyzed oxidizing water and/or electrolyzed alkaline water is injected into an infected portion of an animal (e.g., an infected udder of a cow) to fight the infection. In another embodiment, one or more of the described fluids are applied externally to an animal. For instance, any of the fluids discussed herein (e.g., electrolyzed alkaline water, electrolyzed oxidizing water, etc.) can be applied (e.g., via soaking, wiping, spraying, etc.) to any suitable body part having fungus on it. Indeed, in some embodiments a toenail comprising fungus is soaked in electrolyzed oxidizing water (and/or alkaline water) on a regular basis to rid the toenail of the fungus.

Representative Methods and Operating Environment

The described system 10 and methods can be implemented in any suitable manner. Indeed, in some embodiments, one or more portions of the system 10 are disposed on a vehicle 99 (e.g., a truck, van, trailer, car, bus, tractor, forklift, and/or any other suitable vehicle). For instance, in some embodiments, the vehicle comprises one or more cells 12 (e.g., cells comprising a soda ash and/or any other suitable non-NaCl electrolyte, cells that recirculate anolyte, cell that lack a membrane separating their electrode compartments (e.g., as shown in FIG. 1G), cells that monitor and adjust one or more of their operating parameters based on sensor readings, and/or any other suitable cells), vacuums, wands 100, pumps (e.g., to pump product from the cell to a wand and/or other delivery and/or extraction device), tanks 40 and/or 46, power supplies 51, water softeners 24, and/or any other suitable components (e.g., as illustrated in FIGS. 1L-1O). Thus, in some embodiments, electrolyzed water (e.g., alkaline water and/or any other suitable product) is produced on the vehicle for delivery to a surface to be cleaned (e.g., via the wand 100 and/or in any other suitable manner). In some such cases, such water is delivered from the vehicle to a surface to be cleaned (e.g., via one or more pumps, hoses, wands 100, and/or other suitable components). In some such cases, such electrolyzed water is then sucked up and returned to the vehicle (e.g., tank 46), to a drain, and/or to any other suitable location. Accordingly, in some cases, the described system is substantially contained in and/or on the vehicle and/or is otherwise portable. In this regard, while the vehicle can carry its own water, in some embodiments, it receives some water at its point of use (e.g., from a municipal water supply and/or from any other suitable source). Additionally, as some embodiments of the system recirculate anolyte and/or use a non-NaCl electrolyte, some such embodiments, can produce relatively little waste and leave little to no NaCl residue in the material being cleaned.

In some cases, the systems and methods further comprise using a counter rotating brush device (e.g., as described herein) to pull up hair and other debris from the surface being cleaning. In this regard, the counter rotating brush can be used at any suitable time, including, without limitation, before or after the application of the electrolyzed water to such surface.

In some cases, the systems and methods further comprise applying the cleaning agent (e.g., as described above) to the surface being cleaned. In this regard, such cleaning agent can be applied at any suitable time (e.g., prior, during, and/or after: use of the counter rotating device on the material, application of the electrolyzed water to the material, removal of the electrolyzed water to the mater, and/or at any other suitable time). Indeed, in some embodiments, such cleaning agent is applied to the material being cleaned (e.g., flooring) before such material is cleaned with the electrolyzed water.

While the described system 10 (e.g., cell 12) can function in any suitable manner, an example of a suitable method is described herein. In this regard, it is noted that all of the methods described herein (and each and every portion thereof) can be changed, repeated, omitted, performed partially, mixed with another portion, substituted, replaced, reordered, reconfigured, and/or can otherwise be modified in any suitable manner. In this regard, in some embodiments, the cell is turned on as part of the method (e.g., via one or more switches, by being plugged into a power source, via the control system 38, by a user, and/or in any other suitable manner).

In some embodiments, once the cell is turned on, the cell is in an idle position. In some cases, the system checks to determine (e.g., via one or more sensors and/or other suitable mechanisms) that the product storage tank (e.g., tank 40 and/or any other suitable tank, such as discharge tank 46) is not above a high shutoff level. Additionally, in some embodiments, the system does not produce product (e.g., electrolyzed water) when an emergency stop or reset is engaged. Accordingly, in some cases, the system checks to ensure that an emergency stop or reset is not engaged.

In some cases, when the system starts up, it either receives supply water pressure through the cell's fluid inlet 20 (e.g., via a municipal water supply, a pump, and/or in any other suitable manner). In some cases, as the system is set up to produce product (e.g., electrolyzed alkaline water and/or any other suitable product), an operator and/or the control system 38 verifies that an amperage limit of the cell 12 is set to value to produce NaOH (and/or any other suitable product) at a desired levels.

In some cases, the operator and/or control system 38 verifies (e.g., by looking and/or via one or more sensors and/or measurement mechanisms) that an electrolyte storage take (e.g., a storage tank 62 comprising sodium carbonate and/or any other suitable electrolyte) has an adequate amount (e.g., level) of electrolyte and/or electrolyte solution. In some cases, the method also includes having an operator and/or the control system verify (e.g., by looking and/or via one or more sensors and/or measurement mechanisms) that a level of fluid (e.g., anolyte) in the acid recirculation tank 64 is at or above a minimum level.

In some cases, when the user activates the cell 12, the system 10 (e.g., the control device 38) is configured to reset any active alarms in the system (e.g., indicating that product pH is outside of a set range, indicating that electrolyte conductivity is outside of a set range, etc.). Additionally, in some cases, when the cell is activated, the system allows one or more fluids to flow through the cell. In this regard, the system can allow fluid to flow into one or more compartments of the cell in any suitable manner, including, without limitation, by opening one or more valves on the inlet 20, actuating one or more pumps 28, and/or in any other suitable manner. Moreover, in some cases, as the cell begins to function one or more recirculation pumps 29 start and/or valves 26 open to recirculate electrolyte (e.g., anolyte, as shown in FIGS. 1A-1F) through the cell. In some cases, the system 10 also checks anolyte and catholyte flows to ensure they are at a set level and/or to modify the flows to meet a desired rate.

In some cases, the power supply 51 (e.g., a variable power supply and/or any other power supply) also provides electricity to the electrodes 17 to cause electrolysis within the cell. In some such cases, the system is then configured to automatically provide additional electrolyte and/or electrolyte solution to the cell (e.g., the anolyte flow) via one or more pumps 28, feeders 34, valves 26, and/or in any other suitable manner. Indeed, in some embodiments, the system is configured to add additional electrolyte into the cell until the power supply's amps reach a set limit and/or voltage in the cell begins to drop. In some such cases, the system is configured to tailor (e.g., in near real time, intermittently, constantly, and/or in any other suitable manner) the amount of electrolyte that is added to the cell to help the cell maintain a desired voltage within the cell. Indeed, in accordance with some embodiments, product quality (e.g., the quality of the produced electrolyzed alkaline water and/or any other product) is determined by keeping catholyte inlet flow, and/or anolyte flow within expected limits and/or the power supply voltage at a desired set point.

In some embodiments, the system 10 is configured to keep the amperage supplied by the power supply 51 substantially constant and to vary the electrolyte concentration in the cell so as to compensate for fluctuations in fluid conductivity in one or more portions of the cell. In still some other embodiments, the system is configured to automatically modify the amperage provided to the cell 12, to modify the flowrate of one or more fluids through the cell, to change the concentration of electrolyte within a portion of the cell, and/or to otherwise modify the cell's operation to allow the cell to function optimally and/or to produce one or more desired products.

In some cases, after the system 10 has operated, the system can be shut down in any suitable manner and for any suitable reason. Indeed, in some embodiments, when the system is shut down, the power supply 51 stops providing electricity to the electrodes 17, the recirculation pump 29 stops, the feeder 34 stops, the inlet solenoid valve closes (and/or any other suitable mechanism is actuated to deactivated to stop fluid from flowing into the inlet, in some cases, after a short time delay), and/or the cell otherwise stops producing new product.

In this regard, the system 10 can be shut down when: a user switches the system off or into a rest mode that limits or stops electricity from flowing between the electrodes 17; the system determines that product (e.g., electrolyzed alkaline water) has not been used for an extended period of time; the amount of product in a storage tank has hit a set level; an emergency stop function has been initiated (e.g., by a user, by the control system 38, and/or in any other suitable manner); the system determines that a recirculation flowrate (e.g., through the recirculation loop 31) is too low (e.g., as indicated by one or more sensors and/or alarms); the system determines that a recirculation flowrate is too high (e.g., as indicated by one or more sensors and/or alarms); the system determines that a power supply amperage has dropped too low and/or has gone too high (e.g., as indicated by one or more sensors and/or alarms), the system determines that a cleaner (e.g., product) flow has dropped too low and/or gone too high (e.g., as indicated by one or more sensors and/or alarms); the system determines that an external interlock is not met (e.g., that the inlet water quality has fallen outside of a set level, for instance, the inlet water is too hard, as indicated by one or more sensors and/or alarms); the system determines that the power supply 51 fails to start (e.g., as determined by one or more sensors and/or alarms); the system determines that the storage tank level is too high (e.g., as indicated by one or more sensors and/or alarms); and/or the system otherwise determines that it should be (or the system is otherwise) shut down.

Once the system 10 has been shut down, it (e.g., the cell 12) can started back up at any suitable time. Indeed, in some embodiments, the system starts up again once the system determines that: the product storage tank 40 level is too low (e.g., one or more sensors in the tank or otherwise); a user's has turned the system back on, product is being used (e.g., through a wand), and/or that the cell should otherwise be operating.

In accordance with some embodiments, the system 10 comprises one or more touchscreens; control panels; switchboards; keyboards; displays; lights; indicators; wireless communication devices that are configured to provide information to a phone, laptop, server, handheld device, and/or any other suitable device; and/or any other suitable feature that is configured to provide information to a user regarding the system and its function. Indeed, in some non-limiting embodiments, the system comprises a touchscreen user interface (and/or any other suitable communications center) that provides information on the amperage, voltage, recirculation flowrate, injection pump set point and/or status, cleaner (e.g., electrolyzed water) flowrate, feeder 34 and/or injection pump set point and/or status, system run hours, electrolyte storage tank 62 level and/or status, electrolyte storage tank agitator status, running status of the cell, alarm conditions, and/or any other suitable information relating to the system, its operation, its products, and/or any other suitable feature.

In some embodiments, prior to and/or as the system 10 operates, the system is configured to receive input from a user and to use that input to adjust the functioning of the system (e.g., by (i) having the system automatically, continuously, and/or dynamically make adjustments to its operation to produce products with specific characteristics and/or (ii) allowing the user to set and lock in one or more particular operating parameters (e.g., set and constant amperages, flowrates, electrolyte injection rates, and/or any other suitable parameter) from which the system will not vary).

Indeed, in some embodiments, system 10 is configured to allow a user to modify one or more operating parameters such that the system is able to gather information from one or more sensors and then to modify the system's operating parameters (e.g., dynamically, in near real time, and/or in any other suitable manner) to meet such parameters. In some such embodiments, the system is configured to allow a user to adjust one or more: current limits; voltage limits; operation modes to switch electrolyte injection between an automatic injection setting based on measured conductivity levels and/or any other suitable feature, to a manually controlled electrolyte injection mode; flow alarm set points; electrolyte storage tank agitator controls and status; alarms (e.g., to turn them off, reset the alarms, etc.); sensors (e.g., to recalibrate the sensors); programs that control one or more aspects of the system's operation, and/or other features of the system.

The described systems and methods (e.g., electrolytic system 10, cell 12, wand 100, etc.) can be used with or in any suitable operating environment and/or software. In this regard, FIG. 15 and the corresponding discussion are intended to provide a general description of a suitable operating environment (e.g., control system 38) in accordance with some embodiments of the described systems and methods. As will be further discussed below, some embodiments embrace the use of one or more processing (including, without limitation, micro-processing) units in a variety of customizable enterprise configurations, including in a networked configuration, which may also include any suitable cloud-based service, such as a platform as a service or software as a service.

Some embodiments of the described systems and methods embrace one or more computer readable media, wherein each medium may be configured to include or includes thereon data or computer executable instructions for manipulating data. The computer executable instructions include data structures, objects, programs, routines, or other program modules that may be accessed by one or more processors, such as one associated with a general-purpose processing unit capable of performing various different functions or one associated with a special-purpose processing unit capable of performing a limited number of functions. In this regard, in some embodiments, the processing unit 75 (e.g., the control device 38) comprises a specialized processing unit that is configured for use with the described system 10.

Computer executable instructions cause the one or more processors of the enterprise to perform a particular function or group of functions and are examples of program code means for implementing steps for methods of processing. Furthermore, a particular sequence of the executable instructions provides an example of corresponding acts that may be used to implement such steps.

Examples of computer readable media (including non-transitory computer readable media) include random-access memory ("RAM"), read-only memory ("ROM"), programmable read-only memory ("PROM"), erasable programmable read-only memory ("EPROM"), electrically erasable programmable read-only memory ("EEPROM"), compact disk read-only memory ("CD-ROM"), or any other device or component that is capable of providing data or executable instructions that may be accessed by a processing unit.

Figure 15:
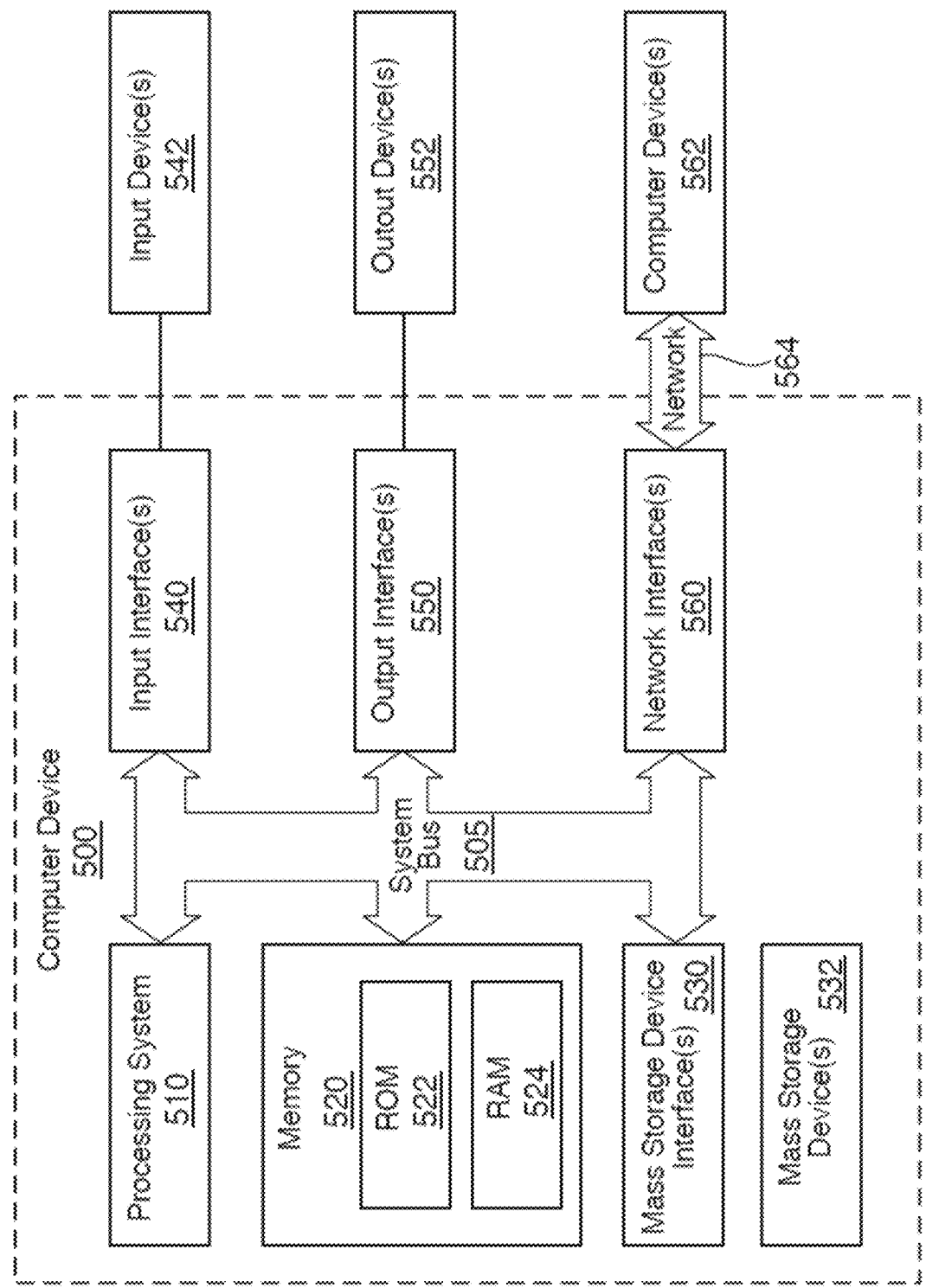
FIG. 15 illustrates a representative system that provides a suitable operating environment for use with some embodiments of the described electrolytic cell and/or cleaning system.

With reference to FIG. 15, a representative system includes computer device 400 (e.g., control system 38 device or other unit), which may be a general-purpose or special-purpose computer (e.g., control unit 38 in communication with the cell 12). For example, computer device 400 may be a personal computer, a notebook computer, a PDA or other hand-held device, a workstation, a minicomputer, a mainframe, a supercomputer, a multi-processor system, a network computer, a processor-based consumer device, a cellular phone, a tablet computer, a smart phone, a feature phone, a smart appliance or device, a control system, or the like.

Computer device 400 includes system bus 405, which may be configured to connect various components thereof and enables data to be exchanged between two or more components. System bus 405 may include one of a variety of bus structures including a memory bus or memory controller, a peripheral bus, or a local bus that uses any of a variety of bus architectures. Typical components connected by system bus 405 include processing system 410 and memory 420. Other components may include one or more mass storage device interfaces 430, input interfaces 440, output interfaces 450, and/or network interfaces 460, each of which will be discussed below.

Processing system 410 includes one or more processors, such as a central processor and optionally one or more other processors designed to perform a particular function or task. It is typically processing system 410 that executes the instructions provided on computer readable media, such as on the memory 420, a magnetic hard disk, a removable magnetic disk, a magnetic cassette, an optical disk, or from a communication connection, which may also be viewed as a computer readable medium.

Memory 420 includes one or more computer readable media (including, without limitation, non-transitory computer readable media) that may be configured to include or includes thereon data or instructions for manipulating data, and may be accessed by processing system 410 through system bus 405. Memory 420 may include, for example, ROM 422, used to permanently store information, and/or RAM 424, used to temporarily store information. ROM 422 may include a basic input/output system ("BIOS") having one or more routines that are used to establish communication, such as during start-up of computer device 400. RAM 424 may include one or more program modules, such as one or more operating systems, application programs, and/or program data.

One or more mass storage device interfaces 430 may be used to connect one or more mass storage devices 432 to the system bus 405. The mass storage devices 432 may be incorporated into or may be peripheral to the computer device 400 and allow the computer device 400 to retain large amounts of data. Optionally, one or more of the mass storage devices 432 may be removable from computer device 400. Examples of mass storage devices include hard disk drives, magnetic disk drives, tape drives, solid state mass storage, and optical disk drives.

Examples of solid state mass storage include flash cards and memory sticks. A mass storage device 432 may read from and/or write to a magnetic hard disk, a removable magnetic disk, a magnetic cassette, an optical disk, or another computer readable medium. Mass storage devices 432 and their corresponding computer readable media provide nonvolatile storage of data and/or executable instructions that may include one or more program modules, such as an operating system, one or more application programs, other program modules, or program data. Such executable instructions are examples of program code means for implementing steps for methods disclosed herein.

One or more input interfaces 440 may be employed to enable a user to enter data (e.g., initial information) and/or instructions to computer device 400 through one or more corresponding input devices 442. Examples of such input devices include a keyboard and/or alternate input devices, such as a digital camera, a sensor, bar code scanner, debit/credit card reader, signature and/or writing capture device, pin pad, touch screen, mouse, trackball, light pen, stylus, or other pointing device, a microphone, a joystick, a game pad, a scanner, a camcorder, and/or other input devices. Similarly, examples of input interfaces 440 that may be used to connect the input devices 442 to the system bus 405 include a serial port, a parallel port, a game port, a universal serial bus ("USB"), a firewire (IEEE 1394), a wireless receiver, a video adapter, an audio adapter, a parallel port, a wireless transmitter, or another interface.

One or more output interfaces 450 may be employed to connect one or more corresponding output devices 452 to system bus 405. Examples of output devices include a monitor or display screen, a speaker, a wireless transmitter, a printer, and the like. A particular output device 452 may be integrated with or peripheral to computer device 400. Examples of output interfaces include a video adapter, an audio adapter, a parallel port, and the like.

One or more network interfaces 460 enable computer device 400 to exchange information with one or more local or remote computer devices, illustrated as computer devices 462, via a network 464 that may include one or more hardwired and/or wireless links. Examples of the network interfaces include a network adapter for connection to a local area network ("LAN") or a modem, a wireless link, or another adapter for connection to a wide area network ("WAN"), such as the Internet. The network interface 460 may be incorporated with or be peripheral to computer device 400.

Figure 16:
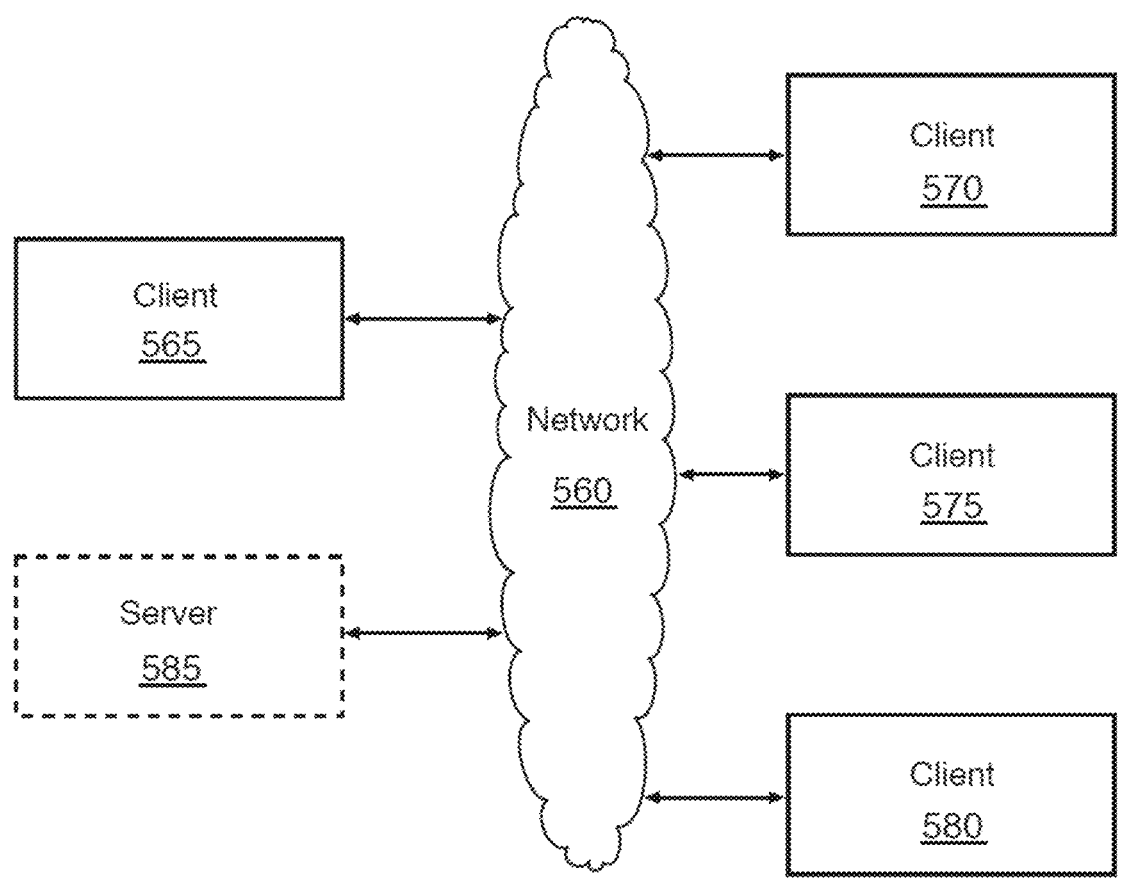
FIG. 16 illustrates a representative embodiment of a networked system that provides a suitable operating environment for use with some embodiments of the described electrolytic cell and/or cleaning system.

In a networked system, accessible program modules or portions thereof may be stored in a remote memory storage device. Furthermore, in a networked system computer device 400 may participate in a distributed computing environment, where functions or tasks are performed by a plurality networked computer devices. While those skilled in the art will appreciate that the described systems and methods may be practiced in networked computing environments with many types of computer system configurations, FIG. 16 represents an embodiment of a portion of the described systems in a networked environment that includes clients (465, 470, 475, etc.) connected to a server 485 via a network 460. While FIG. 16 illustrates an embodiment that includes 3 clients (e.g., electrolytic systems 10, etc.) connected to the network, alternative embodiments include at least one client connected to a network or many clients connected to a network. Moreover, embodiments in accordance with the described systems and methods also include a multitude of clients throughout the world connected to a network, where the network is a wide area network, such as the Internet. Accordingly, in some embodiments, the described systems and methods can allow for remote monitoring, observation, adjusting, trouble shooting, data collecting, system optimizing, donation aggregation, monitoring, user interaction monitoring, and/or other controlling of the systems 10 from many places throughout the world.

The present invention may be embodied in other specific forms without departing from its spirit or essential characteristics. The described systems, methods, embodiments, examples, and illustrations are to be considered in all respects only as illustrative and not restrictive. Any portion of any system, method, embodiment, component, characteristic, and/or other feature of the described systems and methods can be combined, mixed, and/or otherwise used with any other suitable portion of any other feature and in any suitable manner For instance, the described magnets, water conditioning, recirculating anolyte feature, real-time monitoring and/or adjusting, and/or any other feature or method described herein can be used with any feature or method described herein, and in any suitable manner. The scope of the described systems and methods is, therefore, indicated by the appended claims rather than by the foregoing description. All changes that come within the meaning and range of equivalency of the claims are to be embraced within their scope. In addition, as the terms on, disposed on, attached to, connected to, coupled to, etc. are used herein, one object (e.g., a material, element, structure, member, etc.) can be on, disposed on, attached to, connected to, or coupled to another object—regardless of whether the one object is directly on, attached, connected, or coupled to the other object, or whether there are one or more intervening objects between the one object and the other object. Also, directions (e.g., front, back, on top of, below, above, top, bottom, side, up, down, under, over, upper, lower, etc.), if provided, are relative and provided solely by way of example and for ease of illustration and discussion and not by way of limitation. Where reference is made to a list of elements (e.g., elements a, b, c), such reference is intended to include any one of the listed elements by itself, any combination of less than all of the listed elements, and/or a combination of all of the listed elements. Furthermore, as used herein, the terms a, an, and one may each be interchangeable with the terms at least one and one or more.

What is claimed is:

1. An electrolytic cell comprising:
an anode compartment comprising an anode electrode;

a cathode compartment comprising a cathode electrode; and at least one of:
  a first fluid conditioning system comprising:
    a first conduit that is in fluid communication with the electrolytic cell so as to receive an electrolyzed water that is produced by the electrolytic cell; and
    a second conduit that is in fluid communication with the electrolytic cell so as to receive the electrolyzed water that is produced by the electrolytic cell, wherein the first conduit is twisted around the second conduit, and wherein the first fluid conditioning system is configured to mix a first flow of the electrolyzed water from the first conduit with a second flow of the electrolyzed water from the second conduit;
  a second fluid conditioning system comprising:
    a third conduit that is in fluid communication with the electrolytic cell so as to feed a fluid into the electrolytic cell, and
    a fourth conduit that is in fluid communication with the electrolytic cell so as to feed the fluid into the electrolytic cell, wherein the third conduit is twisted around the fourth conduit, and wherein the second fluid conditioning system is configured to combine contents of the third conduit with contents of the fourth conduit; and
  a third fluid conditioning system comprising:
    a fifth conduit that is configured to receive an anolyte from the anode compartment; and
    a sixth conduit that is configured to receive the anolyte from the anode compartment, wherein a length of the fifth conduit is twisted around a length of the sixth conduit, and wherein the fifth conduit and the sixth conduit are configured to recirculate the anolyte from the anode compartment, through the fifth conduit and the sixth conduit, and back into the anolyte compartment.

2. The cell of claim 1, wherein the electrolytic cell comprises the first fluid conditioning system.

3. The cell of claim 2, further comprising a magnet that is configured to apply a magnetic field to the electrolyzed water that passes through the first fluid conditioning system.

4. The cell of claim 1, wherein the electrolytic cell comprises the second fluid conditioning system.

5. The cell of claim 4, further comprising a magnet that is configured to apply a magnetic field to the fluid as it passes through the second fluid conditioning system.

6. The cell of claim 1, wherein the electrolytic cell comprises the third fluid conditioning system.

7. The cell of claim 6, further comprising a magnet that is configured to apply a magnetic field to the anolyte that passes through the third fluid conditioning system.

8. The cell of claim 1, wherein the electrolytic cell further comprises:
  a sensor that is configured to measure a conductivity of a liquid within the electrolytic cell, and
  a processor that is configured to automatically and dynamically modify an amperage that is applied between the anode electrode and the cathode electrode, based on the measured conductivity of the liquid in the electrolytic cell.

9. The cell of claim 1, wherein the cathode electrode is disposed between a first spacer and a second spacer, and wherein first and second spacers each comprise multiple fluid channels that are configured to mix an electrolyte solution as it flows past the cathode electrode.

10. An electrolytic cell comprising:
an anode compartment comprising an anode electrode;
a cathode compartment comprising a cathode electrode;
an ion selective permeable membrane that is disposed between, and that separates, the anode compartment from the cathode compartment; and
at least one of:
  a first fluid conditioning system comprising:
    a first conduit that is in fluid communication with the electrolytic cell so as to receive an electrolyzed water produced by the electrolytic cell; and
    a second conduit that is in fluid communication with the electrolytic cell so as to receive the electrolyzed water produced by the electrolytic cell, wherein the first conduit is twisted around the second conduit, wherein the first conduit and second conduit are coupled together along a portion of their lengths, and wherein the first fluid conditioning system is configured to mix a first flow of the electrolyzed water from the first conduit with a second flow of the electrolyzed water from the second conduit;
  a second fluid conditioning system comprising:
    a third conduit that is in fluid communication with the electrolytic cell so as to feed a fluid into the electrolytic cell, and
    a fourth conduit that is in fluid communication with the electrolytic cell so as to feed the fluid into the electrolytic cell, wherein the third conduit is twisted around the fourth conduit, wherein the third conduit and the fourth conduit are coupled together along a portion of their lengths, and wherein the second fluid conditioning system is configured to combine contents of the third conduit with contents of the fourth conduit; and
  a third fluid conditioning system comprising:
    a fifth conduit that is configured to receive a first portion of an anolyte from the anode compartment; and
    a sixth conduit that is configured to receive a second portion of the anolyte from the anode compartment, wherein a length of the fifth conduit is twisted around, and is coupled together along, a length of the sixth conduit, and wherein the fifth conduit and the sixth conduit are configured to recirculate the anolyte from the anolyte compartment, through the fifth conduit and the sixth conduit, and back into the anolyte compartment.

11. The electrolytic cell of claim 10, wherein the electrolytic cell comprises the first fluid conditioning system, wherein the first fluid conditioning system is coupled to the cathode compartment, and wherein the electrolyzed water comprises electrolyzed alkaline water.

12. The electrolytic cell of claim 11, further comprising a magnet that is configured to provide a magnetic field to the electrolyzed alkaline water that is released from the cathode compartment and that passes through the first fluid conditioning system.

13. The electrolytic cell of claim 11, further comprising:
  a fluid splitter that is configured to split a stream of the electrolyzed alkaline water that is produced by the electrolytic cell into the first flow and the second flow of the electrolyzed alkaline water; and
  a fluid combiner that is configured to combine together the first flow and the second flow of the electrolyzed alkaline water after the first flow and the second flow of the electrolyzed alkaline water have respectively passed through the first conduit and the second conduit.

14. The electrolytic cell of claim 11, further comprising a first container comprising a first electrolyte and a second container comprising a second electrolyte, wherein the electrolytic cell is configured to switch between providing the first electrolyte and the second electrolyte to the electrolytic cell.

15. A system for cleaning, comprising:
a container comprising an electrolyzed water;
a first conduit that is in fluid communication with the container to receive the electrolyzed water from the container; and
a second conduit that is in fluid communication with the container to receive the electrolyzed water from the container, wherein the first conduit and the second conduit are coupled together along a portion of their lengths, and wherein the system for cleaning is configured to mix a first flow of the electrolyzed water from the first conduit and a second flow the electrolyzed water from the second conduit to form a mixture.

16. The system of claim 15, wherein the electrolyzed water comprises electrolyzed alkaline water.

17. The system of claim 15, wherein the system for cleaning further comprises a fluid splitter that is configured to split a stream of the electrolyzed water from the container into the first flow and the second flow of the electrolyzed water.

18. The system of claim 15, wherein the system for cleaning further comprises a combiner that is configured to combine together the first flow and the second flow of the electrolyzed water after the first flow and the second flow of the electrolyzed water have respectively passed through the first conduit and the second conduit.

19. The system of claim 15, wherein the system for cleaning further comprises a magnet that is configured to provide a magnetic field to the electrolyzed water after the electrolyzed water has exited the container, and at least one of: (i) before the electrolyzed water flows into, and (ii) while the electrolyzed water is flowing through, at least one of the first conduit and the second conduit.

20. The system of claim 15,
wherein the electrolyzed water comprises electrolyzed alkaline water, and
wherein the system for cleaning further comprises:
a fluid splitter that is configured to split a stream of the electrolyzed alkaline water from the container into the first flow and the second flow of the electrolyzed alkaline water;
a fluid combiner that is configured to combine together the first flow and the second flow of the electrolyzed alkaline water after the first flow and the second flow of the electrolyzed alkaline water have respectively passed through the first conduit and the second conduit;
a wand that is in fluid communication with the first conduit and the second conduit and that is configured to deliver the electrolyzed alkaline water to a surface that is to be cleaned; and
a pump that is configured to drive the electrolyzed alkaline water from the container to the wand.

* * * * *